US011779647B2

(12) United States Patent
Jeffries et al.

(10) Patent No.: US 11,779,647 B2
(45) Date of Patent: Oct. 10, 2023

(54) COMPLEX COACERVATE FOR CONTROLLED RELEASE AND RELATED METHODS

(71) Applicant: University of Pittsburgh—Of the Commonwealth System of Higher Education, Pittsburgh, PA (US)

(72) Inventors: Eric M. Jeffries, West New York, NJ (US); Yadong Wang, Bradford Woods, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 142 days.

(21) Appl. No.: 17/339,373

(22) Filed: Jun. 4, 2021

(65) Prior Publication Data
US 2021/0290770 A1    Sep. 23, 2021

Related U.S. Application Data

(62) Division of application No. 16/060,075, filed as application No. PCT/US2016/066640 on Dec. 14, 2016, now Pat. No. 11,065,337.

(60) Provisional application No. 62/266,896, filed on Dec. 14, 2015.

(51) Int. Cl.
| | |
|---|---|
| *A61K 38/00* | (2006.01) |
| *A61K 47/58* | (2017.01) |
| *A61K 38/18* | (2006.01) |
| *A61K 38/20* | (2006.01) |
| *A61K 9/06* | (2006.01) |
| *A61K 38/21* | (2006.01) |
| *A61K 47/36* | (2006.01) |
| *A61K 9/10* | (2006.01) |
| *A61K 47/34* | (2017.01) |
| *A61K 9/08* | (2006.01) |
| *A61K 47/61* | (2017.01) |
| *A61P 9/10* | (2006.01) |
| *A61P 35/00* | (2006.01) |
| *A61K 9/00* | (2006.01) |
| *A61K 31/727* | (2006.01) |

(52) U.S. Cl.
CPC ............ *A61K 47/58* (2017.08); *A61K 9/0019* (2013.01); *A61K 9/06* (2013.01); *A61K 9/08* (2013.01); *A61K 9/10* (2013.01); *A61K 31/727* (2013.01); *A61K 38/18* (2013.01); *A61K 38/1825* (2013.01); *A61K 38/20* (2013.01); *A61K 38/208* (2013.01); *A61K 38/2066* (2013.01); *A61K 38/21* (2013.01); *A61K 47/34* (2013.01); *A61K 47/36* (2013.01); *A61K 47/61* (2017.08); *A61P 9/10* (2018.01); *A61P 35/00* (2018.01)

(58) Field of Classification Search
CPC ........ A61K 47/00; A61K 47/58; A61K 47/36; A61K 47/54; A61P 9/10; A61P 9/0019
See application file for complete search history.

(56) References Cited

U.S. PATENT DOCUMENTS

| | | | |
|---|---|---|---|
| 9,023,972 B2 * | 5/2015 | Chu | C08F 8/32 |
| | | | 528/84 |
| 9,095,619 B2 | 8/2015 | Kleiner et al. | |
| 2007/0110813 A1 | 5/2007 | Ingenito et al. | |
| 2013/0071930 A1 | 3/2013 | Chu et al. | |
| 2014/0148395 A1 | 5/2014 | Burdick et al. | |
| 2014/0287061 A1 | 9/2014 | Andolina | |

OTHER PUBLICATIONS

Weiss et al. Expert Opin Biol Ther. Nov. 2007; 7(11): 1705-1721.*
Abbott et al., "Stromal Cell Derived Factor-1alpha Plays a Critical Role in Stem Cell Recruitment to the Heart After Myocardial Infarction but Is Not Sufficient to Induce Homing in the Absence of Injury," 2004, Circulation, vol. 110, pp. 3300-3305.
Aplin et al., "The Aortic Ring Model of Angiogenesis," 2008, Methods in Enzymology, vol. 44, pp. 119-136.
Ashikari-Hada et al., "Characterization of Growth Factor-binding Structures in Heparin/Heparan Sulfate Using an Octasaccharide Library," 2004, J Biol Chem., vol. 279, issue 13, pp. 12346-12354.
Awada et al., "Dual Delivery of Vascular Endothelial Growth Factor and Hepatocyte Growth Factor Coacervate Displays Strong Angiogenic Effects," 2014, Macromol Biosci., vol. 14, issue 5, pp. 679-686.
Awada et al., "Sequential delivery of angiogenic growth factors improves revascularization and heart function after myocardial infarction," 2015, J. Controlled Release, vol. 207, pp. 7-17.
Awada et al., "Factorial Design of Experiments to Optimize Multiple Protein Delivery for Cardiac Repair," 2016, ACS Biomater Sci Eng., vol. 2, pp. 879-885.
Awada et al., "A single injection of protein-loaded coacervate-gel significantly improves cardiac function post infarction," 2017, Biomaterials, vol. 125, pp. 65-80.
Balasubramanian et al., "b3 Integrin in Cardiac Fibroblast Is Critical for Extracellular Matrix Accumulation during Pressure Overload Hypertrophy in Mouse," 2012, PLoS One, vol. 7, issue 9, p. e45076.
Banquet et al., "Arteriogenic Therapy by Intramyocardial Sustained Delivery of a Novel Growth Factor Combination Prevents Chronic Heart Failure," 2011, Circulation, vol. 124, issue 9, pp. 1059-1069.
Bergmann et al., "Evidence for Cardiomyocyte Renewal in Humans," 2009, Science, vol. 324, issue 5923, pp. 98-102.
Bersell et al., "Neuregulin1/ErbB4 Signaling Induces Cardiomyocyte Proliferation and Repair of Heart Injury," 2009, Cell, vol. 138, pp. 257-270.

(Continued)

Primary Examiner — Jeanette M Lieb
(74) Attorney, Agent, or Firm — The Webb Law Firm

(57) ABSTRACT

Provided herein are coacervate compositions including cytokines, and methods of making and using the same. The coacervate can be formed by the mixing of an active agent, such as a drug or protein with the polyanion, such as heparin or heparan sulfate, and a custom-made polycation (e.g., PEAD or PELD). The coacervates can be used in the treatment of diseases and disorders where targeted treatment is desired, for example in treatment of cancers.

14 Claims, 20 Drawing Sheets

Specification includes a Sequence Listing.

(56) References Cited

OTHER PUBLICATIONS

Betsholtz, "Insight into the physiological functions of PDGF through genetic studies in mice," 2004, Cytokine & Growth Factor Reviews, vol. 15, pp. 215-228.

Bhan et al., "High-frequency speckle tracking echocardiography in the assessment of left ventricular function and remodeling after murine myocardial infarction," 2014, Am J Physiol Heart Circ Physiol., vol. 306, pp. H1371-H1383.

Bing et al., "Randomized, multicenter, double-blind, and placebo-controlled trial using topical recombinant human acidic fibroblast growth factor for deep partial-thickness burns and skin graft donor site," 2007, Wound Rep Reg., vol. 15, pp. 795-799.

Black et al., "Protein Encapsulation via Polypeptide Complex Coacervation," 2014, ACS Macro Letters, vol. 3, pp. 1088-1091.

Braun et al., "Breaking the Silence: Stimulating Proliferation of Adult Cardiomyocytes," 2009, Developmental Cell, vol. 17, pp. 151-153.

Brett, "A Review of Collagen and Collagen-based Wound Dressings," 2008, Wounds, vol. 20, issue 12, pp. 347-356.

Brudno et al., "Enhancing microvascular formation and vessel maturation through temporal control over multiple pro-angiogenic and pro-maturation factors," 2013, Biomaterials, vol. 34, pp. 9201-9209.

Capila et al., "Heparin-Protein Interactions", Angewandte Chemie International Edition English, vol. 41, pp. 390-412.

Carmeliet et al., "Molecular mechanisms and clinical applications of angiogenesis", Nature, 2011, pp. 298-307, vol. 473(7347).

Chen et al., "Release characteristics and bioactivity of gelatin-tricalcium phosphate membranes covalently Immobilized with nerve growth factors," 2005, Biomaterials, vol. 26, pp. 6579-6587.

Chen et al., "Spatio-temporal VEGF and PDGF Delivery Patterns Blood Vessel Formation and Maturation," 2007, Pharmaceutical Research, vol. 24, issue 2, pp. 258-264.

Chen et al., "Toward delivery of multiple growth factors in tissue engineering," 2010, Biomaterials, vol. 31, pp. 6279-6308.

Chen et al., "Human pericytes for ischemic heart repair," 2013, Stem Cells., vol. 31, issue 2, pp. 305-316.

Chen et al., "Controlled dual delivery of fibroblast growth factor-2 and Interleukin-10 by heparin-based coacervate synergistically enhances ischemic heart repair," 2015, Biomaterial, vol. 72, pp. 138-151.

Chen et al., "Human myocardial pericytes: multipotent mesodermal precursors exhibiting cardiac specificity," 2015, Stem Cells., vol. 33, issue 2, pp. 557-573.

Choi et al., "Dual Growth Factor Delivery Using Biocompatible Core-Shell Microcapsules for Angiogenesis", Small, 2013, pp. 1-9.

Chu et al., "A [polycation: Heparin] complex releases growth factors with enhanced bioactivity," 2010, Journal of Controlled Release, vol. 150, issue 2, pp. 157-163.

Chu et al., "Injectable fibroblast growth factor-2 coacervate for persistent angiogenesis," 2011, Proceedings of the National Academy of Science, vol. 108, issue 33, pp. 13444-13449.

Chu et al., "Design, synthesis, and biocompatibility of an arginine-based polyester," 2012, Biotechnology Progress, vol. 28, issue 1, pp. 257-264.

Chu et al., "Therapeutic angiogenesis: controlled delivery of angiogenic factors," 2012, Therapeutic Delivery, vol. 3, issue 6, pp. 693-714.

Chu et al., "The effect of a heparin-based coacervate of fibroblast growth factor-2 on scarring in the infarcted myocardium," 2013, Biomaterials, vol. 34, issue 6, pp. 1747-1756.

Cochain et al., "Angiogenesis in the Infarcted Myocardium," 2013, Antioxidants and Redox Signaling, vol. 18, issue 9, pp. 1100-1113.

Cooke et al., "Nitric Oxide and Angiogenesis," 2002, Circulation, vol. 105, pp. 2133-2135.

Crawley et al., "The Coagulation Cascade and Its Regulation," 2011, Textbook of Pulmonary Vascular Disease, editors Yuan et al., chap. 23, pp. 357-370.

Czarkowska-Paczek et al., "The serum levels of growth factors: PDGF, TGF-beta and VEGF are increased after strenuous physical exercise," 2006, J Physiol Pharmacol., vol. 57, issue 2, pp. 189-197.

Davies et al., "Sustaining Neovascularization of a Scaffold Through Staged Release of Vascular Endothelial Growth Factor-A and Platelet-Derived Growth Factor-BB," 2012, Tissue Engineering Part A, vol. 18, pp. 26-34.

De Jong et al., "Dimethylmethylene blue-based spectrophotometry of glycosaminoglycans in untreated urine: a rapid screening procedure for mucopolysaccharidoses," 1989, Clinical Chemistry, vol. 35, issue 7, pp. 1472-1477.

Deblois et al., "Heparin-fibroblast growth factorfibrin complex: in vitro and in vivo applications to collagen-based materials," 1994, Biomaterials, vol. 15, issue 9, pp. 665-672.

Deveza et al., "Therapeutic Angiogenesis for Treating Cardiovascular Diseases," 2012, Theranostics, vol. 2, issue 8, pp. 801-814.

Dhingra et al., "IL-10 attenuates TNF α-induced NF B pathway activation and cardiomyocyte apoptosis," 2009, Cardiovascular Research, vol. 82, pp. 59-66.

Dhurat et al., "Principles and Methods of Preparation of Platelet-Rich Plasma: A Review and Author's Perspective," 2014, J Cutaneous Aesthetic Surg , vol. 7, issue 4, pp. 189-197.

Dobner et al., "A Synthetic Non-degradable Polyethylene Glycol Hydrogel Retards Adverse Post-infarct Left Ventricular Remodeling," 2009, Journal of Cardiac Failure, vol. 15, issue 7, pp. 629-636.

Drinnan et al., "Multimodal release of transforming growth factor-beta1 and the BB isoform of platelet derived growth factor from PEGylated fibrin gels," 2010, Journal of Controlled Release, vol. 147, pp. 180-186.

Driver et al., "A Prospective, Randomized, Controlled Trial of Autologous Platelet-Rich Plasma Gel for the Treatment of Diabetic Foot Ulcers," 2006, Ostomy/Wound Management, vol. 52, issue 6, pp. 68-87.

Eckhouse et al., "Local Hydrogel Release of Recombinant TIMP-3 Attenuates Adverse Left Ventricular Remodeling After Experimental Myocardial Infarction," 2014, Biomaterials, vol. 6, issue 223, p. 223ra21.

Eklund et al., "Tie receptors and their angiopoietin ligands are context-dependent regulators of vascular remodeling," 2006, Experimental Cell Research, vol. 312, pp. 630-641.

Eming et al., "Wound repair and regeneration: Mechanisms, signaling, and translation," 2014, Wound Healing, vol. 6, issue 265, p. 265sr6.

Ensembl: ENSG00000102265, Zerbino, D. R., et al. Ensembl 2018, Nucleic Acids Research, vol. 46, Issue D1, Jan. 4, 2018, pp. D754-D761.

Ensembl: ENSG00000107562, Zerbino, D. R., et al. Ensembl 2018, Nucleic Acids Research, vol. 46, Issue D1, Jan. 4, 2018, pp. D754-D761.

Ensembl: ENSG00000138685, Zerbino, D. R., et al. Ensembl 2018, Nucleic Acids Research, vol. 46, Issue D1, Jan. 4, 2018, pp. D754-D761.

Entrez Gene: 2247, National Center for Biotechnology Information (NCBI)[Internet]. Bethesda (MD): National Library of Medicine (US), National Center for Biotechnology Information; [1988]- [Oct. 5, 2018]. Available from: https://www.ncbi.hlm.nih.gov/.

Entrez Gene: 6387, National Center for Biotechnology Information (NCBI)[Internet]. Bethesda (MD): National Library of Medicine (US), National Center for Biotechnology Information; [1988]-[Oct. 5, 2018]. Available from: https://www.ncbi.nlm.nih.gov/.

Entrez Gene: 7076, National Center for Biotechnology Information (NCBI)[Internet]. Bethesda (MD): National Library of Medicine (US), National Center for Biotechnology Information; [1988]-[Oct. 5, 2018]. Available from: https://www.ncbi.nlm.nih.gov/.

Epstein et al., "Angiogenesis Therapy: Amidst the Hype, the Neglected Potential for Serious Side Effects," 2001, Circulation, vol. 104, pp. 115-119.

Etoh et al., "Myocardial and interstitial matrix metalloproteinase activity after acute myocardial infarction in pigs," 2001, Am J Physiol Circ Physiol., vol. 281, pp. H987-H994.

Ferguson et al., "Prophylactic administration of avotermin for improvement of skin scarring: three double-blind, placebo-controlled, phase I/II studies," 2009, Lancet, vol. 373, pp. 1264-1274.

Ferrara et al., "The biology of VEGF and its receptors," 2003, Nature Medicine, vol. 9, issue 6, pp. 669-676.

(56) References Cited

OTHER PUBLICATIONS

Forbes et al., "Preparing the ground for tissue regeneration: From mechanism to therapy," 2014, Nat Med., vol. 20, issue 8, pp. 857-869.
Formiga et al., "Angiogenic therapy for cardiac repair based on protein delivery systems," 2012, Heart Fail Rev., vol. 17, pp. 449-473.
Frangogiannis, "Regulation of the Inflammatory Response in Cardiac Repair," 2012, Circulation Research, vol. 110, issue 1, pp. 159-173.
Freeman et al., "The effect of sulfation of alginate hydrogels on the specific binding and controlled release of heparin-binding proteins," 2008, Biomaterials, vol. 29, pp. 3260-3268.
Go et al., "The Rat Aortic Ring Assay for In Vitro Study of Angiogenesis," 2003, Methods in Molecular Medicine, vol. 85, pp. 59-64.
Go et al., "Executive Summary: Heart Disease and Stroke Statistics—2014 Update: A Report From the American Heart Association," 2014, Circulation, vol. 129, issue 3, pp. 399-410.
Go et al., "Heart Disease and Stroke Statistics—2014 Update: A Report From the American Heart Association," 2014, Circulation, vol. 128, pp. 1-267.
Greenberg et al., "A role for VEGF as a negative regulator of pericyte function and vessel maturation," 2008, Nature, vol. 456, pp. 809-813.
Grey et al., "Wound assessment," 2006, BMJ, vol. 332, pp. 285-288.
Gullestad et al., "Immunomodulating Therapy With Intravenous Immunoglobulin in Patients With Chronic Heart Failure," 2001, Circulation, vol. 103, issue 2, pp. 220-225.
Ianft et al., "Phase I trial on the safety of topical rhVEGF on chronic neuropathic diabetic foot ulcers," 2008, Journal of Wound Care, vol. 17, issue 1, pp. 30-37.
Hao et al., "Angiogenic and cardiac functional effects of dual gene transfer of VEGF-A(sub)165 and PDGF-BB after myocardial infarction," 2004, Biochemical and Biophysical Research Communications, vol. 322, pp. 292-296.
Hao et al., "Angiogenic effects of sequential release of VEGF-A165 and PDGF-BB with alginate hydrogels after myocardial infarction," 2007, Cardiovascular Research, vol. 75, pp. 178-185.
Hastings et al., "Drug and cell delivery for cardiac regeneration," 2015, Advanced Drug Delivery Reviews, vol. 84, pp. 85-106.
Henry et al., "Intracoronary administration of recombinant human vascular endothelial growth factor to patients with coronary artery disease," 2001, American Heart Journal, vol. 142, issue 5, pp. 872-880.
HGNC: 10672, HGNC Database, HUGO Gene Nomenclature Committee (HGNC), European Molecular Biology aboratory, European Bioinformatics Institute, Wellcome Genome Campus, Hinxton, Cambridgeshire, CB10 1SD, UK; www.genenames.org, retrieved Oct. 2018.
HGNC: 11820, HGNC Database, HUGO Gene Nomenclature Committee (HGNC), European Molecular Biology Laboratory, European Bioinformatics Institute, Wellcome Genome Campus, Hinxton, Cambridgeshire, CB10 1SD, UK; www.genenames.org, retrieved Oct. 2018.
HGNC: 3676, HGNC Database, HUGO Gene Nomenclature Committee (HGNC), European Molecular Biology aboratory, European Bioinformatics Institute, Wellcome Genome Campus, Hinxton, Cambridgeshire, CB10 1SD, UK; www.genenames.org, retrieved Oct. 2018.
Hisieh et al., "Controlled delivery of PDGF-BB for myocardial protection using injectable self-assembling peptide nanofibers," 2006, The Journal of Clinical Investigation, vol. 116, issue 1, pp. 237-248.
Huhn et al., "Pharmacodynamics of subcutaneous recombinant human interleukin-10 in healthy volunteers[ast]," 1997, Clin Pharmacol Ther., vol. 62, issue 2, pp. 171-180.
Hwang et al., "Improving regenerating potential of the heart after myocardial infarction: Factor-based approach," 2010, Life Sciences, vol. 86, pp. 461-472.
Hiwang et al., "The Combined Administration of Multiple Soluble Factors in the Repair of Chronically Infarcted Rat Myocardium," 2011, J Cardiovasc Pharmacol., vol. 57, issue 3, pp. 282-286.
Iyer et al., "Role of Interleukin 10 Transcriptional Regulation in Inflammation and Autoimmune Disease," 2012, Crit Rev Immunol., vol. 32, issue 1, pp. 23-63.
Jiang et al., "Design of a composite biomaterial system for tissue engineering applications," 2014, Acta Biomaterialia, vol. 10, pp. 1177-1186.
Jiao et al., "Chemical Structures and Bioactivities of Sulfated Polysaccharides from Marine Algae," 2011, Mar. Drugs, vol. 9, pp. 196-223.
Johnson et al., "Controlled delivery of heparin-binding EGF-like growth factor yields fast and comprehensive wound healing," 2013, Journal of Controlled Release, vol. 166, pp. 124-129.
Johnson et al., "Controlled Delivery of Sonic Hedgehog Morphogen and Its Potential for Cardiac Repair," 2013, PLOS One, vol. 8, issue 5, p. e63075.
Johnson et al., "Coacervate delivery systems for proteins and small molecule drugs," 2014, Expert Opinion on Drug Delivery, vol. 11, issue 12, pp. 1829-1832.
Johnson et al., "Lysine-based polycation heparin coacervate for controlled protein delivery", Acta Biomater., 2014, vol. 10, pp. 40-46.
Johnson et al., "Coacervate delivery of HB-EGF accelerates healing of type 2 diabetic wounds," 2015, Wound Rep Reg., vol. 23, pp. 591-600.
Kim et al., "The enhancement of mature vessel formation and cardiac function in infarcted hearts using dual growth factor delivery with self-assembling peptides," 2011, Biomaterials, vol. 32, issue 26, pp. 6080-6088.
Kim et al., "Co-delivery of platelet-derived growth factor (PDGF-BB) and bone morphogenic protein (BMP-2) coated onto heparinized titanium for improving osteoblast function and osteointegration," 2015, Journal of Tissue Engineering and Regenerative Medicine, vol. 9, pp. E219-E228.
Kinsella et al., "Interactions of putative heparin-binding domains of basic fibroblast growth factor and its receptor, FGFR-1, with heparin using synthetic peptides," 1998, Glycoconjugate Journal, vol. 15, issue 4, pp. 419-422.
Kis et al., "Second window of protection following myocardial preconditioning: an essential role for PI3 kinase and p70S6 kinase," 2003, Journal of Molecular and Cellular Cardiology, vol. 35, pp. 1063-1071.
Kishimoto et al., "Novel Experimental and Clinical Therapeutic Uses of Low-Molecular-Weight Heparin/Protamine Microparticles," 2012, Pharmaceutics, vol. 4, pp. 42-57.
Krishnamurthy et al., "IL-10 inhibits inflammation and attenuates left ventricular remodeling after myocardial infarction via activation of STAT-3 and suppression of HuR," 2009, Circ Res., vol. 104, issue 2, pp. e9-e18.
Kuhn et al., "Periostin induces proliferation of differentiated cardiomyocytes and promotes cardiac repair," 2007, Nature Medicine, vol. 13, issue 8, pp. 962-969.
Kurrelmeyer et al., "Cardiac Remodeling as a Consequence and Cause of Progressive Heart Failure," 1998, Clinical Cardiology; 1998; vol. 21, sup. I, pp. 14-19.
Lambert et al., "Macrophage roles following myocardial infarction," 2008, International Journal of Cardiology, vol. 130, pp. 147-158.
Latet et al., "The cellular immune system in the post-myocardial infarction repair process," 2015, International Journal of Cardiology, vol. 179, pp. 240-247.
Lee et al., "VEGF Gene Delivery to Myocardium: Deleterious Effects of Unregulated Expression," 2000, Circulation, vol. 102, pp. 898-901.
Lee et al., "Growth factor delivery-based tissue engineering: general approaches and a review of recent developments," 2011, Journal of The Royal Society Interface, vol. 8, pp. 153-170.
Svystonyuk et al., "Fibroblast growth factor-2 regulates human cardiac myofibroblast-mediated extracellular matrix remodeling," 2015, J Transl Med., 2015, vol. 13, issue 147, pp. 1-11.

(56) References Cited

OTHER PUBLICATIONS

Takabayashi et al., "Platelet-rich plasma-containing fragmin-protamine micro-nanoparticles promote epithelialization and angiogenesis in split-thickness skin graft donor sites," 2015, J Surg Res., vol. 193, pp. 483-491.
Takehara et al., "Controlled Delivery of Basic Fibroblast Growth Factor Promotes Human Cardiosphere-Derived Cell Engraftment to Enhance Cardiac Repair for Chronic Myocardial Infarction," 2008, Journal of the American College of Cardiology; vol. 52, issue 23, pp. 1858-1865.
Takikawa et al., "PRP&F/P MPs Improved Survival of Dorsal Paired Pedicle Skin Flaps in Rats," 2011, Journal of Surgical Research, vol. 170, pp. e189-e196.
Tang et al., "VEGF/SDF-1 promotes cardiac stem cell mobilization and myocardial repair in the infarcted heart," 2011, Cardiovascular Research, vol. 91, pp. 402-411.
Tang et al., "The enhancement of endothelial cell therapy for angiogenesis in hindlimb ischemia using hyaluronan," 2011, Biomaterials, vol. 32, pp. 75-85.
Tayalia et al., "Controlled Growth Factor Delivery for Tissue Engineering," 2009, Advanced Materials, vol. 21, pp. 3269-3285.
Tengood et al., "Sequential delivery of vascular endothelial growth factor and sphingosine 1-phosphate for angiogenesis," 2010, Biomaterials, vol. 31, pp. 7805-7812.
Tengood et al., "Sequential Delivery of Basic Fibroblast Growth Factor and Platelet-Derived Growth Factor for Angiogenesis," 2011, Tissue Engineering: Part A, vol. 17, pp. 1181-1189.
Tian et al., "Inhibiting Matrix Metalloproteinase by Cell-Based Timp-3 Gene Transfer Effectively Treats Acute and Chronic Ischemic Cardiomyopathy," 2012, Cell Transplantation, vol. 21, pp. 1039-1053.
Tsai, "von Willebrand Factor, Shear Stress, and ADAMTS13 in Hemostasis and Thrombosis," 2012, ASAIO Journal, vol. 58, pp. 163-169.
Tsang et al., "Postconditioning: A Form of "Modified Reperfusion" Protects the Myocardium by Activating the Phosphatidylinositol 3-Kinase-Akt Pathway," 2004, Circ Res., vol. 95, pp. 230-232.
Turner et al., "Chronic beta2-adrenergic receptor stimulation increases proliferation of human cardiac fibroblasts via an autocrine mechanism," 2003, Cardiovascular Research, vol. 57, pp. 784-792.
Uchinaka et al., "Tissue inhibitor of Metalloproteinase-1 and -3 Improves Cardiac Function in an Ischemic Cardiomyopathy Model Rat," 2014, Tissue Engineering: Part A, vol. 20, pp. 3073-3084.
UniProtKB: P01033, UniProt: the universal protein knowledgebase Nucleic Acids Res. 45: D158-D169 (2017), Accession No.
UniProtKB: P09038, UniProt: the universal protein knowledgebase Nucleic Acids Res. 45: D158-D169 (2017), Accession No.
UniProtKB: P48061, UniProt: the universal protein knowledgebase Nucleic Acids Res. 45: D158-D169 (2017), Accession No.
Van Der Zee et al., "Vascular Endothelial Growth Factor/Vascular Permeability Factor Augments Nitric Oxide Release From Quiescent Rabbit and Human Vascular Endothelium," 1997, Circulation, vol. 95, pp. 1030-1037.
Van Rugge et al., "Magnetic Resonance Imaging During Dobutamine Stress for Detection and Localization of Coronary Artery Disease: Quantitative Wall Motion Analysis Using a Modification of the Centerline Method," 1994, Circulation, vol. 90, issue 1, pp. 127-138.
Vasita et al., "Growth factor-delivery systems for tissue engineering: a materials perspective," 2006, Expert Rev Med. Devices, vol. 3, issue 1, pp. 29-47.
Visse et al., "Matrix Metalloproteinases and Tissue Inhibitors of Metalloproteinases: Structure, Function, and Biochemistry," 2003, Circ Res., vol. 92, pp. 827-839.
Vu et al., "Matrix metalloproteinases: effectors of development and normal physiology," 2000, Genes & Development, vol. 14, pp. 2123-2133.
Vu et al., "An autologous platelet-rich plasma hydrogel compound restores left ventricular structure, function and ameliorates adverse remodeling in a minimally invasive large animal myocardial restoration model: A translational approach Vu and Pal Myocardial Repair: PRP, Hydrogel and Supplements," 2015, Biomaterials, vol. 45, pp. 27-35.
Wandt et al., "Echocardiographic assessment of ejection fraction in left ventricular hypertrophy," 1999, Heart, vol. 82, issue 2, pp. 192-198.
Wang, "Mitogen-Activated Protein Kinases in Heart Development and Diseases," 2007, Circulation, vol. 116, issue 12. pp. 1413-1423.
Wright et al., "Early healing events in a porcine model of contaminated wounds: effects of nanocrystalline silver on matrix metalloproteinases, cell apoptosis, and healing," 2002, Wound Rep Reg., vol. 10, pp. 141-151.
Yan et al., "Acceleration of Full-thickness Wound Healing in Porcine Model by Autologous Platelet Gel," 2007, Wounds, vol. 19, issue 4, pp. 79-86.
Yang et al., "Enhanced skin wound healing by a sustained release of growth factors contained in platelet-rich plasma," 2011, Experimental and Molecular Medicine, vol. 43, issue 11, pp. 622-629.
Yu et al., "TIMP-3 Binds to Sulfated Glycosaminoglycans of the Extracellular Matrix," 2000, J Biol Chem., vol. 275, issue 40, pp. 31226-31232.
Yu et al., "Effects of Combination of Angiotensin-Converting Enzyme Inhibitor and Angiotensin Receptor Antagonist on Inflammatory Cellular Infiltration and Myocardial Interstitial Fibrosis After Acute Myocardial Infarction," 2001, Journal of the American College of Cardiology, vol. 38, issue 4, pp. 1207-1215.
Zachary et al., "Therapeutic angiogenesis for cardiovascular disease: biological context, challenges, prospects," 2010, Heart, vol. 97, pp. 181-189.
Zangi et al., "Modified mRNA directs the fate of heart progenitor cells and induces vascular regeneration after myocardial infarction," 2013, Nat Biotechnol., vol. 31, issue 10, pp. 898-907.
Zern et al., "Control growth factor release using a self-assembled [polycation: heparin] complex," 2010, PLoS One, vol. 5, p. e11017.
Zhang et al., "Sequential, timely and controlled expression of hVEGF165 and Ang-1 effectively improves functional angiogenesis and cardiac function in vivo," 2013, Gene Therapy, vol. 20, pp. 893-900.
Zhang et al., "The Potential Use of Allogeneic Platelet-Rich Plasma for Large Bone Defect Treatment: Immunogenicity and Defect Healing Efficacy," 2013, Cell Transplantation, vol. 22, pp. 175-187.
Zhao et al., "Efficacy of topical recombinant human platelet-derived growth factor for treatment of diabetic lower extremity ulcers: Systematic review and meta-analysis," 2014, Metabolism Clinical and Experimental, vol. 63, pp. 1304-1313.
Lee et al., "Bone regeneration with low dose BMP-2 amplified by biomimetic supramolecular nanofibers within collagen scaffolds," 2013, Biomaterials, vol. 34, pp. 452-459.
Lee et al., "Human progenitor cell recruitment via SDF-1alpha coacervate-laden PGS vascular grafts," 2013, Biomaterials, vol. 34, pp. 9877-9885.
Li et al., "The Role of Therapeutic Angiogenesis in Tissue Repair and Regeneration," 2005, Advances in Skin and Wound Care, vol. 18, issue 9, pp. 491-500.
Li et al., "Sustained release of bone morphogenetic protein 2 via coacervate improves the osteogenic potential of muscle-derived stem cells," 2013, Stem Cells Transl Med., vol. 2, issue 9, pp. 667-677.
Long et al., "Complex Coacervate as a Protein Delivery Vehicle," 2016, Poster Presentation, McGowan Retreat.
Lubinski et al., "Speckle tracking methods for ultrasonic elasticity imaging using short-time correlation," 1999, IEEE Transactions on Ultrasonics, Ferroelectrics, and Frequency Control, vol. 46, issue 1, pp. 82-96.
Lui et al., "Cardiovascular regenerative therapeutics via synthetic paracrine factor modified mRNA," 2014, Stem Cell Research, vol. 13, issue 3B, pp. 693-704.
Madduri et al., "Effect of controlled co-delivery of synergistic neurotrophic factors on early nerve regeneration in rats," 2010, Biomaterials, vol. 31, issue 32, pp. 8402-8409.
Malliaras et al., "Cardiomyocyte proliferation vs progenitor cells in myocardial regeneration: The debate continues," 2013, Global Cardiology Science and Practice, vol. 37, pp. 303-315.

(56) References Cited

OTHER PUBLICATIONS

Manning et al., "In vivo assessment of LV mass in mice using high-frequency cardiac ultrasound: necropsy validation," 1994, American Journal of Physiology, vol. 266, issue 4, pp. H1672-H1675.
Martinez-Zapata et al., "Autologous platelet-rich plasma for treating chronic wounds (Review)," 2016, Cochrane Database of Systematic Reviews, vol. 5, p. CD006899.
Maulik et al., "Growth factor/s and cell therapy in myocardial regeneration," 2008, Journal of Molecular and Cellular Cardiology, vol. 44, pp. 219-227.
Middleton et al., "Evaluation Of The Effects Of Platelet-Rich Plasma (PRP) Therapy Involved In The Healing Of Sports-Related Soft Tissue Injuries," 2012, The Iowa Orthopaedic Journal, vol. 32, pp. 150-163.
Mohtaram et al., "Biomaterial-based drug delivery systems for the controlled release of neurotrophic factors," 2013, Biomedical Materials, vol. 8, issue 2, p. 022001.
Moore et al., "Interleukin-10 and the interleukin-10 receptor," 2001, Annual Review of Immunology, vol. 19, issue 1, pp. 683-765.
Morbidelli et al., "Nitric oxide mediates mitogenic effect of VEGF on coronary venular endothelium," 1996, American Journal of Physiology, vol. 270, pp. H411-H415.
Mulloy et al., "Conformation and dynamics of heparin and heparan sulfate," 2000, Glycobiology, vol. 10, issue 11, pp. 1147-1156.
Mussano et al., "Cytokine, chemokine, and growth factor profile of platelet-rich plasma," 2016, Platelets, vol. 27, issue 5, pp. 467-471.
Nagai et al., "Gene and cytokine therapy for heart failure: Molecular mechanisms in the improvement of cardiac function," 2012, Am J Physiol Heart Circ Physiol., vol. 303, pp. H501-H512.
O'Donnell et al., "Internal displacement and strain imaging using ultrasonic speckle tracking," 1994, IEEE Transactions on Ultrasonics, Ferroelectrics, and Frequency Control, vol. 41, issue 3, pp. 314-325.
Ogle et al., "Distilling complexity to advance cardiac tissue engineering," 2016, Science Translational Medicine, vol. 8, issue 342, p. 342ps13.
Online Mendelian Inheritance in Man, OMIM (TM). Johns Hopkins University, Baltimore, MD. MIM No. 134920: Oct. 7, 2016: Retrieved from http://www.ncbi.nlm.nih.gov/omim/.
Online Mendelian Inheritance in Man, OMIM (TM). Johns Hopkins University, Baltimore, MD. MIM No. 305370: Oct. 14, 2010: Retrieved from http://www.ncbi.nlm.nih.gov/omim/.
Online Mendelian Inheritance in Man, OMIM (TM). Johns Hopkins University, Baltimore, MD. MIM No. 600835: Jan. 19, 2016: Retrieved from http://www.ncbi.nlm.nih.gov/omim/.
Papanas et al., "Becaplermin gel in the treatment of diabetic neuropathic foot ulcers," 2008, Clinical Interventions in Aging, vol. 3, issue 2, pp. 233-240.
Pellegrini, "Role of heparan sulfate in fibroblast growth factor signaling: a structural view," 2001, Current Opinion in Structural Biology, vol. 11, pp. 629-634.
Pinto et al., "Macrophages in cardiac homeostasis, injury responses and progenitor cell mobilization," 2014, Stem Cell Research, vol. 13, issue 3B, pp. 705-714.
Pollick et al., "Echocardiographic and cardiac doppler assessment of mice," 1995, Journal of the American Society of Echocardiography, vol. 8, issue 5, pp. 602-610.
Porter et al., "Simvastatin reduces human atrial myofibroblast proliferation independently of cholesterol lowering via inhibition of RhoA," 2004, Cardiovascular Research, vol. 61, pp. 745-755.
Qian et al., "In vivo reprogramming of murine cardiac fibroblasts into induced cardiomyocytes," 2012, Nature, vol. 485, pp. 593-598.
Rajangam et al., "Heparin Binding Nanostructures to Promote Growth of Blood Vessels," 2006, Nano Letters, vol. 6, issue 9, pp. 2086-2090.
Rauck et al., "Biocompatibility of a Coacervate-Based Controlled Release System for Protein Delivery to the Injured Spinal Cord," 2015, Acta Biomater., vol. 11, pp. 204-211.
Richardson et al., "Polymeric system for dual growth factor delivery," 2001, Nature Biotechnology, vol. 19, pp. 1029-1034.
Ruvinov et al., "The promotion of myocardial repair by the sequential delivery of IGF-1 and HGF from an injectable alginate biomaterial in a model of acute myocardial infarction," 2011, Biomaterials, vol. 32, pp. 565-578.
Sager et al., "RNAi targeting multiple cell adhesion molecules reduces immune cell recruitment and vascular inflammation after myocardial infarction," 2016, Science Translational Medicine, vol. 8, issue 342, p. 342ra80.
Salek-Ardakani et al., "Heparin and heparan sulfate bind interleukin-10 and modulate its activity," 2000, Blood, vol. 96, issue 5, pp. 1879-1888.
Sakiyama-Elbert, "Incorporation of heparin into biomaterials," 2014, Acta Biomaterialia, vol. 10, pp. 1581-1587.
Schoen et al., "The Heart," 2010, Robbins & Cotran Pathologic Basis of Disease, 8th ed., chap. 12, pp. 555-618.
Schultz et al., "Interactions between extracellular matrix and growth factors in wound healing," 2009, Wound Rep Reg., vol. 17, pp. 153-162.
Segers et al., "Protein Therapeutics for Cardiac Regeneration after Myocardial Infarction," 2010, J Cardiovasc Trans Res., vol. 3, pp. 469-477.
Senyo et al., "Cardiac regeneration based on mechanisms of cardiomyocyte proliferation and differentiation," 2014, Stem Cell Research, vol. 13, issue 3B, pp. 532-541.
Shin et al., "Co-delivery of Vascular Endothelial Growth Factor and Angiopoietin-1 Using Injectable Microsphere/ Hydrogel Hybrid Systems for Therapeutic Angiogenesis," 2013, Pharmaceutical Research, vol. 30, issue 8, pp. 2157-2165.
Shin et al., "Sequential delivery of TAT-HSP27 and VEGF using microsphere/hydrogel hybrid systems for therapeutic angiogenesis," 2013, Journal of Controlled Release, vol. 166, pp. 38-45.
Silva et al., "Growth Factor Delivery Approaches in Hydrogels," 2009, Biomacromolecules, vol. 10, issue 1, pp. 9-18.
Slawson et al., "Cardiac MRI of the Normal and Hypertrophied Mouse Heart," 1998, Magnetic Resonance in Medicine, vol. 39, pp. 980-987.
Sternlicht et al., "How Matrix Metalloproteinases Regulate Cell Behavior," 2001, Annu Rev Cell Dev Biol., vol. 17, pp. 463-516.
Stumpf et al., "Interleukin-10 improves left ventricular function in rats with heart failure subsequent to myocardial infarction," 2008, Eur J. Heart Failure, vol. 10, issue 8, pp. 733-739.
Sun et al., "Angiotensin II, Transforming Growth Factor-Beta1 and Repair in the Infarcted Heart," 1998, J Mol Cell Cardiol., vol. 30, pp. 1559-1569.
Sun et al., "Sustained Release of Multiple Growth Factors from Injectable Polymeric System as a Novel Therapeutic Approach Towards Angiogenesis," 2010, Pharmaceutical Research, vol. 27, issue 2, pp. 264-271.
Sutton et al., "Left Ventricular Remodeling After Myocardial Infarction: Pathophysiology and Therapy," 2000, Circulation, vol. 101, pp. 2981-2988.
Giordano et al., "Intracoronary gene transfer of fibroblast growth factor-5 increases blood flow and contractile function in an ischemic region of the heart," 1996, Nature Medicine, vol. 2, pp. 534-539.
Kawamoto et al., "Therapeutic Potential of Ex Vivo Expanded Endothelial Progenitor Cells for Myocardial Ischemia," 2001, Circulation, vol. 103, pp. 634-637.

\* cited by examiner

A

*Primary Tumor*

B

*Contralateral Tumor*

A

Primary Tumor

B

Contralateral Tumor

- IL-12, 1ug
- IL-12, 10ug
- IL-12, 30ug
- Blank
- PBS

COMPLEX COACERVATE FOR CONTROLLED RELEASE AND RELATED METHODS

CROSS REFERENCE TO RELATED APPLICATIONS

This application is a divisional application of U.S. patent application Ser. No. 16/060,075, filed Jun. 7, 2018, which is the United States national phase of International Application No. PCT/US2016/066640 filed Dec. 14, 2016, and claims the benefit of U.S. Provisional Patent Application No. 62/266,896, filed Dec. 14, 2015, each of which is incorporated herein by reference in its entirety.

STATEMENT REGARDING FEDERAL FUNDING

This invention was made with government support under Grant Nos DMR1005766 and IIP1444774, awarded by the National Science Foundation. The government has certain rights in the invention.

SEQUENCE LISTING STATEMENT

The Sequence Listing associated with this application is filed in electronic format via EFS-Web and is hereby incorporated by reference into the specification in its entirety. The name of the text file containing the Sequence Listing is 6527_1803711_ST25.txt. The size of the text file is 1828 bytes, and the text file was created on Jun. 7, 2018.

BACKGROUND OF THE INVENTION

Provided herein are compositions useful for drug delivery, for example for delivery of cytokines, and methods of use of those compositions, for example for treatment of coronary heart disease and cancer.

Cytokines are produced by a broad range of cell types and serve as soluble modulators of immune function in vitro and in vivo. In the cancer setting, interleukins (IL), such as IL-2 and IL-12, and interferons (IFN), such as IFN-α and IFN-γ, are capable of promoting protective anti-tumor immunity in patients with solid forms of cancer. However, systemic delivery of high-doses of these agents over prolonged periods of time has resulted in severe toxicities, and even patient deaths.

Coronary heart disease (CHD) affects 15.4 million Americans and is the most common type of heart disease. CHD alone accounts for 385,000 deaths and costs an estimated total of $108.9 billion annually (direct and indirect) in the United States. CHD caused by pathological blockage of the coronary circulation may lead to prolonged ischemia which in turn results in permanent cardiomyopathy and/or myocardial infarction (MI). MI causes death of cardiac myocytes and triggers local inflammatory responses and the compensatory scar formation, leading to pathological remodeling and ultimately heart failure (HF). Recent experimental therapies for cardiac repair primarily focus on revascularization and regeneration of impaired myocardium. However, to break the vicious cycle of MI-to-HF, not only is revascularization of the ischemic tissue desirable, but also modulation or the over-activated and prolonged inflammation following myocardial injury.

A safe and effective method of delivery of cytokines is needed for treatment of patients, for example with coronary heart disease and cancer.

SUMMARY

Systemic toxicities of cytokines can be avoided by the directed delivery of these cytokines in a local manner, i.e. into the treatment site. Provided herein is a controlled delivery coacervate made of a combination of a polyanion, such as heparin or heparan sulfate and a synthetic polycationic copolymer. The coacervate is formed by the mixing of an active agent, such as a drug or protein with the polyanion, such as heparin or heparan sulfate, and a custom-made polycation (e.g., PEAD or PELD). Complex coacervates are formed by mixing oppositely charged polyelectrolytes resulting in spherical droplets of organic molecules held together noncovalently and apart from the surrounding liquid. The coacervate system provides a higher level of control over the release of drugs from a delivery system. Embedding a drug in coacervate compositions leads to the release of the drug over days to months. Slow release of drugs also is desirable when timing of delivery impacts treatment—for example, to prevent release of a large bolus of cytokines to a patient, and to normalize delivery of cytokines over a much longer time period than has been possible using conventional delivery vehicles such as saline.

Provided is a composition comprising a complex or coacervate of a polycationic polymer, a polyanionic polymer, such as heparin or heparan sulfate and a cytokine selected from an interferon and/or an interleukin. In one aspect, the polycationic polymer is PEAD or PELD, or polymer composition comprising at least one moiety selected from the following:

(a) [—OC(O)—CH(NHY)—$CH_2$—C(O)O—$CH_2$—CH(O—R1)-$CH_2$—O—$CH_2$—$CH_2$—O—$CH_2$—CH(O—R2)-$CH_2$-]$_n$, (b) [—OC(O)—$CH_2$—CH(NHY)—C(O)O—$CH_2$—CH(O—R1)-$CH_2$—O—$CH_2$—$CH_2$—O—$CH_2$—CH(O—R2)-$CH_2$-]n, (c) [—OC(O)—CH(NHY)—$CH_2$—$CH_2$—C(O)O—$CH_2$—CH(O—R1)-$CH_2$—O—$CH_2$—$CH_2$—O—$CH_2$—CH(O—R2)-$CH_2$-]$_n$, and/or (d) [—OC(O)—$CH_2$—$CH_2$—CH(NHY)—C(O)O—$CH_2$—CH(O—R1)-$CH_2$—O—$CH_2$—$CH_2$—O—$CH_2$—CH(O—R2)-$CH_2$-]n, wherein Y is —C(O)—CH($NH_3^+$)—$(CH_2)_3$—NH—C$(NH_2)_2^+$ or —C(O)—CH($NH_3^+$)—$(CH_2)_4$—$(NH_3)^+$, and R1 and R2 are the same or different and are independently selected from the group consisting of hydrogen, a carboxy-containing group, a $C_{1-6}$ alkyl group, an amine-containing group, a quaternary ammonium containing group, and a peptide. In one aspect, the cytokine is immunomodulatory. In another aspect, the cytokine is IL-12. In another, the cytokine is IL-10, and the composition optionally further comprises an angiogenic growth factor such as FGF2. In another aspect, the composition is embedded in a hydrogel.

Also provided are methods of treatment of coronary heart disease, such as a myocardial infarction comprising administering to a patient in need thereof an effective amount of the composition described above, and herein, e.g., including effective amounts of IL-10 and FGF2. Further, a method of treatment of a cancer is provided, comprising administering to a patient in need thereof an effective amount of the composition described above and herein, e.g., including an effective amount of an IL-12.

BRIEF DESCRIPTION OF THE DRAWINGS

(FIG. 1A) Schematic illustration of putative FGF2/IL- 10 coacervate structure (PEAD in blue in original, heparin in green in original, FGF2 in yellow in original, and IL-10 in orange in original). Please note that FGF2 and IL-10 molecules bound to heparin are circled with green dashed lines while FGF2 and IL-10 molecules physically entrapped within the coacervate structure (no affinity-based binding) are circled with dashed line. (FIG. 1B) Analysis of coacervate droplet size with polydispersity index (PDI). (FIG. 1C) The release profile of FGF2/IL-10 coacervate in vitro for 3 weeks. Equal amount of FGF2 and IL-10 were first combined and then mixed with heparin, followed by the addition of PEAD to form coacervate, with a mass ratio of PEAD:heparin:FGF2:IL-10=500:100:1:1. Supernatants were collected on Day 0, 0.5, 1, 4, 7, 10, 14, and 21 and then replenished with PBS containing fresh 0.5 U/mL heparinase II in order to simulate the release of cargo proteins in vivo (N=4 per time point). The amount of released FGF2 and IL-10 was measured by ELISA. Data are presented as percent cumulative release (normalized to the original load). Error bars indicate means±SD. (FIG. 1D) Incorporation of fluorescently labeled FGF2 (green in original) and IL-10 (red in original) into coacervate droplets (scale bar=25 µm) (FIG. 1E) High-magnification enlargement of the coacervate droplet in the dotted area in (FIG. 1D) showing fluorescently labeled FGF-2 and IL-10 molecules evenly distributed within the droplet (scale bar=5 µm). (FIG. 1F) Triply labeled heparin (red in original), FGF2 (green in original) and IL-10 (blue in original) showing nearly homogeneous structure of FGF-2/IL-10 coacervate (scale bar=10 µm). Please note that due to the limitation of imaging resolution, larger coacervate droplets were chosen for high-magnification imaging.

(FIG. 5A) Representative axial strain maps laid over B-mode images (4×6 mm) showing the axial strain distribution of the normal (left panel) and untreated MI control (right panel, mid-infarct level) left ventricles respectively. For normalization purpose, the infarct area was designated as B, and the non-infarct area was designated as A. (FIG. 5B) Normalized strain was obtained by dividing spatially averaged axial strain of B by that of A (B/A). Coa-F-500, Coa-F/I-500/100, and Coa-F/I-500/500 showed markedly greater normalized strains than the saline control and Free-F/I-500/500. Free-F/I-500/500 also showed notably higher normalized strains than the saline control (#p<0.001, †p<0.01; N=3 per group). Error bars indicate means±SD. Statistical differences between groups were analyzed by one-way ANOVA with Bonferroni post-hoc analysis.

(FIG. 7A) Representative images of CD31+ ECs (red in original) and αSMA+ cells (green in original) within the infarct and peri-infarct areas at the mid-infarct level, with dotted areas enlarged. Please note that vascular smooth muscle cells (VSMC) were defined as perivascular/peri-CD31 αSMA+ cells. Nuclei were stained with DAPI in blue (in original). (scale bars=100 μm) (FIG. 7B, left) Quantitative analyses of CD31+ EC density within the infarct area revealed that Coa-F/I-500/500 had significantly higher EC density than the saline control and Free-F/I-500/500 while Coa-F/I-500/100 had significantly higher EC density than the saline control (*p<0.05, †p<0.01; N=4 per group). (FIG. 7B, right) Within the peri-infarct area, Coa-F/I-500/500 had significantly higher EC density than the saline control, Free-F/I-500/500, and Coa-F-500 while Coa-F/I-500/100 had significantly higher EC density than the saline control and Free-F/I-500/500 (#p<0.001, *p<0.05; N=4 per group). Error bars indicate means±SD. Statistical differences between groups were analyzed by one-way ANOVA with Bonferroni post-hoc analysis.

DETAILED DESCRIPTION

Figure 1A:
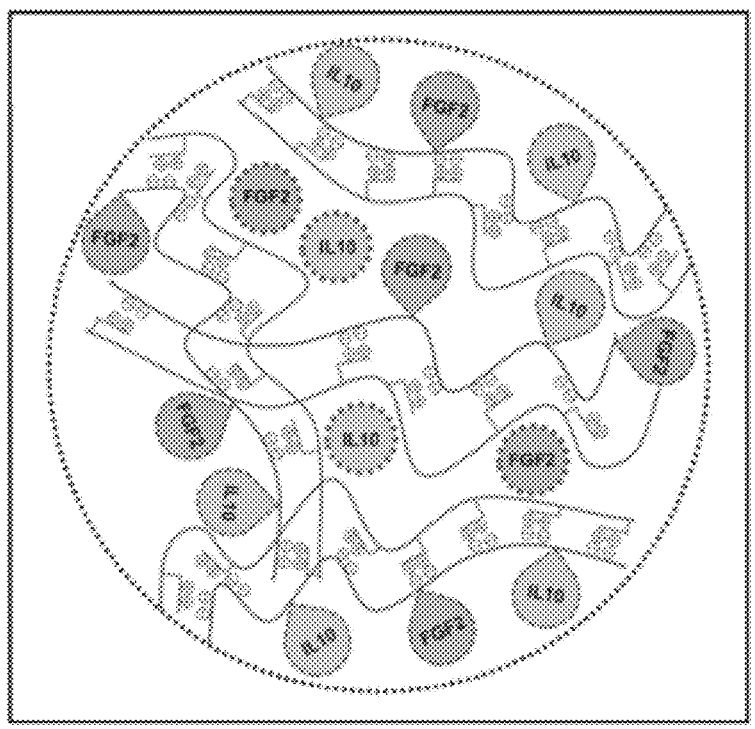
FIGS. 1A-1F. Characterization of FGF2/IL-10 coacervate.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

A composition is provided herein to control the delivery rate of cytokines, for example, interleukins (IL), such as IL-2 and IL-12 (e.g., IL-12 p70), and interferons (IFN), such as IFN-γ. The controlled delivery system comprises a recently developed heparin-based coacervate. Complex coacervates are formed by mixing oppositely charged polyelectrolytes resulting in spherical droplets of organic molecules held together noncovalently and apart from the surrounding liquid and have shown potential in sustained protein delivery. One application of the coacervate is to control the release of cytokines and interferons. Methods of making and using the composition also are provided.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

A "coacervate" refers to herein as a reversible aggregation of compositions in a liquid, for example, as described herein, for example, resulting from the aggregation of oppositely-charged polyionic compositions. Exemplary coacervates are illustrated in the examples below with the aggregation of the polycation, polyanion, and active agent(s), as described herein, for example with the aggregation of PEAD, Heparin, and IL-12, or IL-10 combined with FGF2. A "complex" is a non-covalent aggregation of two or more compositions.

The term "alkyl" refers to both branched and straight-chain saturated aliphatic hydrocarbon groups. These groups can have a stated number of carbon atoms, expressed as $C_{x-y}$, where x and y typically are integers. For example, $C_{5-10}$, includes $C_5$, $C_6$, $C_7$, $C_8$, $C_9$, and $C_{10}$. Alkyl groups include, without limitation: methyl, ethyl, propyl, isopropyl, n-, s- and t-butyl, n- and s-pentyl, hexyl, heptyl, octyl, etc. Alkenes comprise one or more double bonds and alkynes comprise one or more triple bonds. These groups include groups that have two or more points of attachment (e.g., alkylene). Cycloalkyl groups are saturated ring groups, such as cyclopropyl, cyclobutyl, or cyclopentyl. As used herein, "halo" or "halogen" refers to fluoro, chloro, bromo, and iodo.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage, such as an ester, or urethane linkage, if that linkage is present in the polymer.

Certain polymers described herein, such as heparin and PEAD, are said to be bioerodible or biodegradable. By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months. Non-limiting examples of such chemical reactions include acid/base reactions, hydrolysis reactions, and enzyme catalyzed bond scission. Certain polymers described herein contain labile ester linkages. The polymer or polymers may be selected so that it degrades over a time period. Non-limiting examples of useful in situ degradation rates include between 12 hours and 5 years, and increments of hours, days, weeks, months or years therebetween.

A drug delivery composition is provided, comprising, a coacervate of a polycationic polymer, a polyanionic polymer, and an active agent. In certain aspects, the polycationic polymer described herein comprises the structure (that is, comprises the moiety: [—OC(O)—B'—CH(OR1)-B-]$_n$ or —[OC(O)—B—C(O)O—CH$_2$—CH(O—R1)-CH$_2$—B'—CH$_2$—CH(O—R2)-CH$_2$-]$_n$, in which B and B' are the same or different and are organic groups, or B' is not present, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids, and R1 and R2 are the same or different and are hydrogen or a functional group (e.g., as described herein). As seen below, the composition exhibits low polydispersity, with a polydispersity index of less than 3.0, and in many cases less than 2.0. These compositions are described in U.S. Pat. No. 9,023,972, which is incorporated by reference in its entirety.

In one aspect, the polycationic polymer is a polymer composition comprising at least one moiety selected from the following in which B and B' are residues of aspartic acid or glutamic acid, which are optionally further derivatized with an amine-containing group, for example, the amines of the aspartic acid or glutamic acid are further derivatized with lysine or arginine:

(a) [—OC(O)—CH(NHY)—CH$_2$—C(O)O—CH$_2$—CH(O—R1)-CH$_2$—O—CH$_2$—CH$_2$—O—CH$_2$—CH(O—R2)-CH$_2$-]$_n$, (b) [—OC(O)—CH$_2$—CH(NHY)—C(O)O—CH$_2$—CH(O—R1)-CH$_2$—O—CH$_2$—CH$_2$—O—CH$_2$—CH(O—R2)-CH$_2$-]$_n$, (c) [—OC(O)—CH(NHY)—CH$_2$—CH$_2$—C(O)O—CH2-CH(O—R1)-CH$_2$—O—CH$_2$—CH$_2$—O—CH$_2$—CH(O—R2)-CH$_2$-]$_n$, and/or (d) [—OC(O)—CH$_2$—CH$_2$—CH(NHY)—C(O)O—CH2-CH(O—R1)-CH$_2$—O—CH$_2$—CH$_2$—O—CH$_2$—CH(O—R2)-CH$_2$-]$_n$, wherein Y is —C(O)—CH(NH$_3^+$)—(CH$_2$)$_3$—NH—C(NH$_2$)$_2^+$ or —C(O)—CH(NH$_3^+$)—(CH$_2$)$_4$—(NH$_3$)$^+$, and R1 and R2 are the same or different and are independently selected from the group consisting of hydrogen, a carboxy-containing group, a $C_{1-6}$ alkyl group, an amine-containing group, a quaternary ammonium containing group, and a peptide.

The polymers described herein can be functionalized, e.g., at B, B', R1 and R2, meaning they comprise one or more groups with an activity, such as a biological activity. For example and without limitation, as shown herein, the polymer may be functionalized with an acetylcholine-like group or moiety, a cross-linking agent (cross-linking agents contain at least two reactive groups that are reactive towards numerous groups, including sulfhydryls and amines, and create chemical covalent bonds between two or more molecules, functional groups that can be targeted with cross-linking agents include primary amines, carboxyls, sulfhydryls, carbohydrates and carboxylic acids. A large number of such agents are available commercially from, e.g., Thermo fisher Scientific (Pierce) and Sigma.

Other functions that can be provided by or enhanced by addition of functional groups include: increased hydrophobicity, for instance by functionalizing with a superhydrophobic moiety, such as a perfluoroalkane, a perfluoro(alkylsilane), and/or a siloxane; increased hydrophilicity, for instance by functionalizing with polyethylene glycol (PEG); or antimicrobial, for instance, by functionalizing with a quaternary amine. The polymer can be functionalized with a tag, such as a fluorescent tag (e.g., FITC, a cyanine dye, etc.). The polymer can be functionalized by linking to additional synthetic or natural polymers, including, without limitation: synthetic polymers, such as a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, a polymer comprising carbonate linkages, a polycarbonate, a polyglyconate, a poly(glycolide-co-trimethylene carbonate), a poly(glycolide-co-trimethylene carbonate-co-dioxanone), a polymer comprising urethane linkages, a polyurethane, a poly(ester urethane) urea, a poly(ester urethane) urea elastomer, a polymer comprising ester linkages, a polyalkanoate, a polyhydroxybutyrate, a polyhydroxyvalerate, a polydioxanone, a polygalactin, or natural polymers, such as chitosan, collagen, gelatin, elastin, alginate, cellulose, hyaluronic acid and other glycosaminoglycans.

The compositions may be functionalized with organic or inorganic moieties to achieve desired physical attributes (e.g., hardness, elasticity, color, additional chemical reactivity, etc.), or desired functionality. For example, the polymer composition may be derivatized with maleic acid or phosphate.

The composition is formed into a coacervate with active agents or polyanionic or polycationic groups for sequestering active agents for controlled delivery in vivo. Drug products comprising the coacervate described herein may be delivered to a patient by any suitable route of delivery (e.g. oral or parenteral), or as an implantable device for slow release of the active agent.

The functional groups may vary as indicated above. For example, in certain embodiments, R1 and R2 are the same or different and are independently selected from the group consisting of hydrogen, a carboxy-containing group, a $C_{1-6}$ alkyl group, an amine-containing group, a quaternary ammonium containing group, and a peptide. In one embodiment, one or more of B, B', R1 and R2 are charged such that it is possible to bind various water insoluble organic or inorganic compounds to the polymer, such as magnetic inorganic compounds. As above, in one embodiment, one or more of B, B', R1 and R2 are positively charged. In one embodiment, one or both of R1 and R2 are functionalized with a phosphate group. In another embodiment, the composition is attached non-covalently to a calcium phosphate (including as a group, for example and without limitation: hydroxyapatite, apatite, tricalcium phosphate, octacalcium phosphate, calcium hydrogen phosphate, and calcium dihydrogen phosphate). In yet another embodiment, R1 and R2 are independently one Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12)).

In forming the composition (e.g., coacervate), the cationic polycationic polymer is complexed with a polyanionic polymer, such as heparin or heparan sulfate, which is further complexed with an active agent, such as a growth factor, small molecule, cytokine, drug, a biologic, a protein or polypeptide, a chemoattractant, a binding reagent, an antibody or antibody fragment, a receptor or a receptor fragment, a ligand, or an antigen and/or an epitope. Specific examples of active agents include interleukins (IL), such as IL-2 and IL-12 (e.g., IL-12 p70), and interferons (IFN), such as IFN-γ. In one aspect, the composition comprises a coacervate of a polycationic polymer comprising one or more of moieties (a), (b), (c), and/or (d), as described above, and further comprising heparin or heparin sulfate complexed (that is non-covalently bound) with the a first active agent, such as IL-2, IL-12 (e.g., IL-12 p70), and/or IFN-γ, in any combination. The composition is formed, for example, by mixing in a suitable solvent, such as an aqueous solution, such as water, saline (e.g. normal saline), or PBS, the polyanionic, polycationic, and active agent constituents of the composition.

Additional active agents that may be incorporated into the coacervate include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, anti-inflammatory cytokines, and anti-inflammatory proteins or steroidal anti-inflammatory agents); antibiotics; anticlotting factors such as heparin, Pebac, enoxaparin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethasone, dexamethasone, flumethasone, isoflupredone, methylprednisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, bevacizumab, neovastat; (3) antiproliferatives such as sirolimus, paclitaxel, perillyl alcohol, farnesyl transferase inhibitors, FPTIII, L744, anti-proliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, nitrates, nitrites, Diethylamine NONOate, Diethylamine NONOate/AM, Glyco-SNAP-1, Glyco-SNAP-2, (.+-.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, ofloxacin, ampicillin, amphotericin B, atovaquone, azithromycin, ciprofloxacin, clarithromycin, clindamycin, clofazimine, dapsone, diclazuril, doxycycline, erythromycin, ethambutol, fluconazole, fluoroquinolones, foscarnet, ganciclovir, gentamicin, itraconazole, isoniazid, ketoconazole, levofloxacin, lincomycin, miconazole, neomycin, norfloxacin, ofloxacin, paromomycin, penicillin, pentamidine, polymyxin B, pyrazinamide, pyrimethamine, rifabutin, rifampin, sparfloxacin, streptomycin, sulfadiazine, tetracycline, tobramycin, trifluorouridine, trimethoprim sulfate, Zn-pyrithione, and silver salts such as chloride, bromide, iodide and periodate.

Further examples of additional active agents include: basic fibroblast growth factor (bFGF or FGF-2), acidic fibroblast growth factor (aFGF), nerve growth factor (NGF), vascular endothelial growth factor (VEGF), hepatocyte growth factor (HGF), transforming growth factor-beta pleiotrophin protein, midkine protein, platelet-derived growth factor (PDGF) and angiopoietin-1 (Ang-1). Active agents are included in the delivery system described herein, and are administered in amounts effective to achieve a desired end-point, such as angiogenesis, tissue growth, inhibition of tissue growth, or any other desirable end-point.

According to one aspect, complex structures are provided that comprise the coacervate described herein mixed with, distributed within, or otherwise combined with another composition, such as a hydrogel, a polymer, an inorganic substrate, a medical implant or device such as a prosthetic, a dosage form, a woven or non-woven mesh, etc. According to one aspect, the coacervate is combined with a hydrogel, for example by embedding the coacervate in a hydrogel. Such a structure is useful for providing complex release profiles for active agents, for instance for promoting specific tissue growth or as a timed-release dosage form. In such an aspect, one or more active agents are distributed by any method in the coacervate and in the hydrogel so as to cause a defined degradation and release pattern. One useful aspect would be to embed the coacervate having a first active agent into a hydrogel, having a second active agent, to provide a complex release profile. In any aspect, the active agent(s) can be any effective active agent(s), for example as described above. As an example, factor A is embedded into a hydrogel, e.g. a fibrin gel, for early release and factor B is contained within the coacervate, for delayed release. For each indicated purpose it is noted that appropriate relative amounts of the coacervate and hydrogel may be used, as well as including effective amounts of the active agents for the intended purpose, respectively in the coacervate and hydrogel. Appropriate and effective amounts of each component can be determined in the ordinary course by a person of skill in the art.

Examples of useful active agents and combinations of agents for incorporation into the described coacervate for treatment of cancers include: IL2, IL-12, and IFNγ and combinations thereof. Also described herein is a method of treatment of myocardial infarction, using the combination of IL-10 and fibroblast growth factor-2 (FGF-2) in the described coacervate.

The coacervate composition is delivered in any manner useful for treatment of a condition in a patient, such as for treatment of cardiovascular disease or cancer, such as by enteral, parenteral, or topical routes, for example and without limitation by: intravenous (IV), local injection, intramuscular, intracerebral, subcutaneous, orally, inhalation, topically, enema, intravaginal, intrauterine, ocular, or otic routes.

Suitable excipients or carriers are employed for delivery of the coacervate composition, though the excipients are consistent with maintenance of the coacervate complex. Suitable excipients are broadly-known in the pharmaceutical arts, and include: solvents, such as water, phosphate-buffered saline (PBS), saline; buffers; salts; acids; bases; rheology modifiers; chelating agents; colorants; flavorings; penetration enhancers; and preservatives. The coacervate composition is provided in a suitable vessel for storage, distribution and/or use of the composition. In one aspect, the coacervate composition is provided in a tube, a medical syringe, an IV bag. In another aspect, the coacervate composition is delivered to a patient in an amount effective to treat a myocardial infarction, for example by direct injection of the coacervate composition comprising IL-10 and FGF-2 into the heart, e.g., the myocardium at or adjacent to an infarct.

An "amount effective" for treatment of a condition is an amount of an active agent or dosage form, such as the coacervate composition described herein, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. In the context of cancers, the end point may be increased survival, reduction in tumor mass, or any other objectively-determinable indicator of improvement in a patient's condition or symptoms. Using the teachings of the present disclosure, a person of ordinary skill in the arts can prepare the coacervate composition described herein, and titrate the effect on any objectively-determinable end-point, such as tumor mass or survival, for instance first in an animal model and later in humans. As shown in the Examples below, an example of an "amount effective" is indicated.

The coacervate composition may be administered continually for a period of time, or at intervals, ranging from hourly, weekly, monthly, or yearly, including increments therebetween, such as from one to six times per day, daily, every other day, weekly, bi-weekly, monthly, bi-monthly, quarterly, etc. An appropriate dosing schedule can be determined by a person of ordinary skill, such as a physician, and can also be tailored to disease progression and severity in a patient (e.g., staging and/or grading) and/or the type of cancer, or improvement in cardiac output or repair.

In use, according to one aspect, the coacervate composition is delivered to a patient in an amount effective to treat a cancer or hyperplasia in a patient. Cancers or hyperplasia particularly suited for treatment in this manner include solid tumors, that is, a mass or masses of cancerous cells, such as melanoma, or other hyperplasia. The composition is delivered, for example by injection, at or adjacent to a mass. In one aspect, the composition is delivered to a patient at or adjacent to a mass, such as a tumor, the composition comprising IL-12. The composition is administered in an amount effective to treat the cancer, that is to improve one or more clinically-relevant markers, such as to reduce mass size, to destroy the mass, to reduce the cancer grade, and/or to improve patient survival.

In another aspect, the coacervate composition is delivered to a patient in an amount effective to treat a cardiovascular disease, such as coronary heart disease, including treatment of ischemic conditions, such as myocardial infarction. In one aspect, the composition is delivered to a patient's myocardium at or adjacent to an infarct, the composition comprising an antiinflammatory immunomodulatory cytokine, such as IL-10, and an amount of an angiogenic growth factor, such as FGF-2. The cytokine and angiogenic growth factor are administered in an amount effective to treat the infarct, that is to improve one or more clinically-relevant markers, such as to improve cardiac function parameters such as myocardial elasticity, to reduce infarct size, to increase revascularization of the infarct, to reduce scarring of the myocardium, and/or stimulate repair of the myocardium. Other conditions, such as myocardial reperfusion injury and peripheral artery disease may be treated in the same manner.

Example 1—Synthesis and Testing of PEAD

Synthesis and testing of PEAD, PEAD-heparin, and PEAD FGF2 are described in U.S. Pat. No. 9,023,972, which is incorporated by reference in its entirety. Briefly, for synthesis of PEAD—t-BOC protected aspartic acid (t-BOC Asp), t-BOC protected arginine (t-BOC-Arg) (EMD Chemicals, NJ), ethylene glycol diglycidyl ether (EGDE), trifluoroacetic acid (TFA) (TCI America, OR), anhydrous 1,4-dioxane and tetra-n-butylammonium bromide (TBAB) (Acros organics, Geel, Belgium), dicyclohexylcarbodiimide (DCC), N-hydroxysuccinimide (NHS) (Alfa Aesar, MA) and 4-dimethylaminopyridine (DMAP) (Avocado Research Chemicals Ltd, Lancaster, UK) were used for PEAD synthesis without purification. The synthesis of PEAD is performed as follows. EGDE and t-BOC Asp were polymerized in 1,4-dioxane under the catalysis of TBAB. t-BOC protection was later removed by TFA to generate primary amine. t-BOC-Arg was conjugated by DCC/NHS/DMAP coupling followed by the second de-protection to yield PEAD. The chemical structure was confirmed using NMR and FT-IR. The molecular weight of PEAD was measured by PL-GPC 50 Plus-RI equipped with a PD 2020 light scattering detector (Varian, MA). Two MesoPore 300×7.5 mm columns and 0.1% of LiBr in DMF were used as solid phase and mobile phase, respectively. In one example, the weight-average molecular weight (Mw) is 30,337 Da with polydispersity index (PDI) 2.28.

Since PEAD is a positively-charged molecule, addition of PEAD into heparin solution should neutralize the negative charge of heparin and forms PEAD/heparin complex. To test the binding ability of PEAD to heparin, zeta potential measurement was performed and the zeta potential of the complex shifted from negatively-charged (−45 mV) at ratio 1 to positively-charged (+23.2 mV) at ratio 10. Continuing adding more PEAD did not change the zeta potential and +23.2 mV is close to the zeta potential of PEAD itself. Data suggested that for the described PEAD preparation after ratio 10 the complex was all covered by PEAD. Besides it also shows at ratio 5 PEAD almost neutralized all negative charges of heparin. From the macroscopic observation, below ratio 5 the addition of PEAD let the heparin solution became more turbid and precipitate was seen after a few minutes. Whereas the ratio was over 5, the addition of PEAD would let the solution become clear again.

Further confirming the binding ability, different amounts of PEAD to heparin solutions were mixed and then precipitated by centrifugation. Because the neutralization of the negative-charged heparin favors the formation of precipitate, we measured the amount of heparin left in the supernatant was measured to determine the binding affinity between PEAD and heparin. For this assay, a heparin binding dye, dimethylmethylene blue (DMB) was applied to detect free heparin by measuring the absorption of DMB at 520 nm. The result shows the amount of heparin in the supernatant was gradually lowered with the addition of PEAD. When the ratio of PEAD to heparin is over 3, >90% of heparin was precipitated through centrifugation. At the ratio 5, that would be >99% of heparin. This result has a good correlation with that of zeta potential measurement because both experiments suggest at ratio 5 PEAD and heparin has the maximum interaction.

It is understood that a variety of growth factors can bind to heparin with the dissociation constant (Kd) from μM to nM. The loading efficiency of growth factors to PEAD/heparin complex was studied. 100 ng or 500 ng of fibroblast growth factor-2 (FGF-2) plus $^{125}$I-labeled FGF-2 used as a tracer were mixed with heparin then added into PEAD solution. After staying at room temperature for 2 hr, centrifugation was used to precipitate PEAD/heparin/FGF-2. The amount of unloaded FGF-2 remaining in the supernatant can be determined by a gamma counter. The result showed PEAD/heparin loaded ~68% of FGF-2 for both high and low amounts of FGF-2. The other growth factor, NGF, the release is faster. The initial burst reached almost 20%. The release sustained till day 20 and reached a plateau corresponding to ~30% of the loaded NGF.

Example 2—Cytokine Delivery and Treatment of Cancer

The following represents use of the compositions described herein in the cancer setting using coacervates integrating the immunostimulatory cytokines IL-2, IL-12, and IFN-γ as locoregional therapies against murine melanomas.

Methods:

Generation of QC of Coacervates: Coacervates containing cytokines will be prepared according to the following. Briefly, poly(ethylene argininylaspartate diglyceride) (PEAD) and clinical-grade heparin (Scientific Protein Labs, Waunakee, Wis., USA) will be separately dissolved in 0.9% normal saline (Baxter Healthcare, Deerfield, Ill., USA) at 10 mg/ml and sterilized by passing through a 0.22 μm syringe filter. A 5:1 ratio of PEAD and heparin by weight will be used to maintain electric neutrality (that is, the coacervate has a neutral charge where the ratio of the polycationic polymer to the polyanionic polymer is such that the overall positive charge of the polycationic polymer equals or approximates the overall negative charge of the polyanionic polymer in the coacervate). Heparin will be first complexed with a pre-determined, equal amount of recombinant murine IL-2, IL-12p70, or IFN-γ (all from PeproTech, Rocky Hill, N.J., USA) and mixed well. PEAD will subsequently be added into the solution containing [heparin:cytokine] complexes. Self-assembly of PEAD and [heparin:cytokine] will immediately precipitated the ternary complex out of solution to form the cytokine coacervates. Precipitation of coacervate complexes will immediately increase turbidity in solution. Coacervates will be freshly-prepared immediately before all in vitro and in vivo experiments to avoid aggregation. Coacervate droplet sizes will be measured using a Zetasizer Nano ZS90 (Malvern, Worcestershire, UK) and reported as the mean with polydispersity index (PDI) from 25 measurements. Results will then be averaged from measurements of three independent coacervate samples for each cytokine cohort. PDI in the area of light scattering will depict the droplet size distribution.

The cytokine release profile of the prepared coacervates will be determined in vitro as previously described (Chen W C, et al., Controlled dual delivery of fibroblast growth factor-2 and Interleukin-10 by heparin-based coacervate synergistically enhances ischemic heart repair. *Biomaterials.* 2015; 72:138-51. PMID: 26370927; PMCID: PMC4617784). To simulate release of cargo molecules, phosphate-buffered saline (PBS) supplemented with 0.5 U/mL heparinase II will be added to each sample to bring up the final volume to 200 μL. Four independent samples were then placed statically in a humidified cell culture incubator at 37° C. At Day 0, 0.5, 1, 4, 7, 10, 14, and 21, samples will be pelleted by centrifugation (12,100 g for 10 min), followed by the collection of supernatants. Samples will then be replenished with fresh solution and well mixed before being returned to the incubator. Solutions will be stored at −80° C. prior to analysis using cytokine-specific ELISA (BD Biosciences).

Tumor Therapy Experiments: C57BL/6 mice will be injected s.c. in their right flank with 1-2×10$^5$ syngeneic melanoma cells (BRAF$^{WT}$ B16 or BRAF$^{V600}$E BP) and tumors allowed to establish for 7-10 days. Tumor-bearing mice will then be randomized into cohorts of 5 mice/group, with each group exhibiting similar mean tumor sizes (based on the product of orthogonal measurements in mm$^2$). Cohorts of mice will then be injected intra-tumorally (i.t.) with 50 microliters of i.) PBS (control), ii.) a cytokine-free coacervate (control), iii.) coacervates containing rmIL-2, iv.) coacervates containing rmIL-12, v.) coacervates containing rmIFN-γ, vi.) rmIFN-γ (control), vii.) rmIL-2 (control), viii.) rmIL-12 (control), and/or ix.) rmIFN-γ (control). Combinations of cytokines also are tested essentially as indicated above. If in vitro QC analyses suggest abbreviated release of a given incorporated cytokine, individual cohorts of mice may be retreated with an identical i.t. injection (PBS, control coacervate or cytokine-containing coacervate) based on the kinetic profile of cytokine release. Mice will be monitored for tumor size over time, as well as, time-to-euthanasia as a measure of survival. Animals will be euthanized if melanomas exceed a size of 400 mm$^2$ or if they become openly ulcerated. It is to be expected that animals undergoing a protective immune response will exhibit inflammation at tumor sites, hence the reddening of lesions may be reflective of an ongoing local immune response and will not be grounds for euthanasia. Mice will also be euthanized if they exhibit signs of discomfort or behavioral abnormalities (i.e. hunching, labored breathing, fur ruffling), or if they exhibit a >20% weight-loss on protocol. Experiments will be performed at least twice for both the B16 and BP melanoma models.

Second-level analyses of coacervates that mediate statistically-significant therapeutic benefits to melanoma-bearing mice will be evaluated in 2-site (s.c. right flank+s.c. left flank) melanoma models, where only tumor on the right flank will be treated by i.t. delivered coacervates (vs. PBS). This will allow us to discern systemic immune benefits resulting from treatment on both directly-treated tumors (right flank) vs. untreated lesions (left flank), allowing us to interpret therapy efficacy against disseminated disease. At time of euthanasia, we will harvest the lungs of tumor-bearing mice to enumerate pulmonary metastases (i.e. both B16 and BP melanomas spontaneously metastasize to the lungs) as we have previously described[36]. If >1 cytokine-containing coacervate mediates anti-melanoma efficacy in vivo, we plan to determine whether combination of such species is capable of providing improved treatment outcome. Such studies would involve cohorts (n=5 each) of melanoma-bearing animals treated with i.) PBS, ii.) cytokine-free coacervate, iii.) cytokine 1 coacervate, iv.) cytokine 2 coacervate, v.) cytokine 1 coacervate+cytokine 2 coacervate. Combinations of cytokines also are tested essentially as indicated above.

In both single and 2-site melanoma models we may include additional animals per cohort to allow for immune monitoring. In particular, 1-2 additional mice/treatment cohort would allow for us to harvest spleens, tumor-draining lymph nodes (TDLNs) and tumors for analysis of anti-melanoma CD8$^+$ T cell frequencies (after stimulation with melanoma antigen [MART1, gp100, TRP2]-derived peptides as monitored in IFN-γ ELISPOT assays) and total lymphocyte subset counts (i.e. CD4$^+$ T cells, CD8$^+$ T cells, NKp46$^+$ NK cells, CD4$^+$Foxp3$^+$ Treg, and CD11b$^+$Gr1$^+$ MDSC as determined by flow cytometry). It would be anticipated that cytokine-containing coacervates mediating treatment benefits would promote increased anti-specific CD8$^+$ T cell frequencies and reduced presence of Treg/MDSC based on our past experience with effective immunotherapies in murine melanoma models.

Statistics: Non-parametric tests will be used for the comparison of different groups of in vitro experiments. Mixed effect models will be fit to the log scale tumor volume to compare the growth curve of different treatment groups to controls. Time-to-euthanasia will be summarized by the Kaplan-Meier method, and log-rank tests will be used to compare the survival curves between different treatment groups.

Example 3—Cytokine Delivery and Treatment of Myocardial Infarction (MI)

Myocardial infarction (MI) causes myocardial necrosis, triggers chronic inflammatory responses, and leads to pathological remodeling. Controlled delivery of a combination of angiogenic and immunoregulatory proteins may be a promising therapeutic approach for MI. We investigated the bioactivity and therapeutic potential of an injectable, heparin-based coacervate co-delivering an angiogenic factor, fibroblast growth factor-2 (FGF2), and an anti-inflammatory cytokine, Interleukin-10 (IL-10) in a spatially and temporally controlled manner. Coacervate delivery of FGF2 and IL-10 preserved their bioactivities on cardiac stromal cell proliferation in vitro. Upon intramyocardial injection into a mouse MI model, echocardiography revealed that FGF2/IL-10 coacervate treated groups showed significantly improved long-term LV contractile function and ameliorated LV dilatation. FGF2/IL-10 coacervate substantially augmented LV myocardial elasticity. Additionally, FGF2/IL-10 coacervate notably enhanced long-term revascularization, especially at the infarct area. In addition, coacervate loaded with 500 ng FGF2 and 500 ng IL-10 significantly reduced LV fibrosis, considerably preserved infarct wall thickness, and markedly inhibited chronic inflammation at the infarct area. These results indicate that FGF2/IL-10 coacervate has notably greater therapeutic potential than coacervate containing only FGF2. Overall, our data suggest therapeutically synergistic effects of FGF-2/IL-10 coacervate, particularly coacervate with FGF2 and 500 ng IL-10, for the treatment of ischemic heart disease.

Example 4—Controlled Dual Delivery of Fibroblast Growth Factor-2 and Interleukin-10 by Heparin-Based Coacervate Synergistically Enhances Ischemic Heart Repair We recently developed a controlled delivery system that utilizes the charge interaction between a biodegradable polycation, poly(ethylene argininylaspartate diglyceride) (PEAD), and a natural polyanion, heparin, to form coacervate. This heparin-based coacervate delivery platform protects and steadily releases heparin-binding growth factors, including fibroblast growth factor-2 (FGF2) (See, e.g., U.S. Pat. No. 9,023,972, which is incorporated herein by reference in its entirety), nerve growth factor (NGF), heparin-binding epidermal growth factor-like growth factor (HB-EGF), stromal cell-derived factor (SDF)-1α, and bone morphogenetic protein-2 (Chu, H., et al., *A [polycation: heparin] complex releases growth factors with enhanced bioactivity*. Journal of Controlled Release, 2011. 150(2): p. 157-163; Johnson, N. R. and Wang, Y., *Controlled delivery of heparin-binding EGF-like growth factor yields fast and comprehensive wound healing*. Journal of Controlled Release, 2013. 166(2): p. 124-129; Li, H., et al., *Sustained Release of Bone Morphogenetic Protein 2 via Coacervate Improves the Osteogenic Potential of Muscle-Derived Stem Cells*. Stem Cells Translational Medicine, 2013. 2(9): p. 667-77; and Li, H., et al., *Sustained Release of Bone Morphogenetic Protein 2 via Coacervate Improves the Osteogenic Potential of Muscle-Derived Stem Cells*. Stem Cells Translational Medicine, 2013. 2(9): p. 667-77). In addition, heparin-based coacervate has been shown to efficiently deliver HB-EGF in a mouse model of skin wound healing, accelerating keratinocyte migration and wound closure, and FGF2 in a mouse model of subcutaneous injection, promoting local neoangiogenesis and blood vessel maturation (Johnson, N. R. and Wang, Y., Journal of Controlled Release, 2013. 166(2): p. 124-129 and Chu, H., et al., *Injectable fibroblast growth factor-2 coacervate for persistent angiogenesis*. Proceedings of the National Academy of Sciences, 2011. 108(33): p. 13444-13449. Furthermore, in a murine MI model, coacervate containing 500 ng FGF2 has been proven effective in augmenting functional angiogenesis and blood vessel stabilization, reducing cardiomyocyte death and peri-infarct fibrosis, and improving cardiac function (Chu, H., et al., *The effect of a heparin-based coacervate of fibroblast growth factor-2 on scarring in the*

*infarcted myocardium.* Biomaterials, 2013. 34(6): p. 1747-1756). Utilizing the versatile protein-binding capacity of heparin, we theorized that dual delivery of FGF2 and an anti-inflammatory agent by coacervate can be therapeutically more effective than the delivery of FGF2 alone.

Interleukin-10 (IL-10) is a pleiotropic cytokine that exhibits broad immunoregulatory and anti-inflammatory activities. Human IL-10 binds to heparin with high affinity at pH 7.4 (Kd=54±7 nM). The role of IL-10 in the cardiac milieu has been investigated in recent years. In congestive HF patients, higher plasma levels of anti-inflammatory mediators such as IL-10 notably correlates with augmented contractile function of the left ventricle (LV). Daily subcutaneous injections of recombinant human IL-10 (rhIL-10, 75 µg/kg-day) for 4 weeks in a rat model of acute MI (AMI) resulted in significantly reduced productions of proinflammatory cytokines, diminished myocardial macrophage infiltration, and augmented LV function (Stumpf, C., et al., *Interleukin-10 improves left ventricular function in rats with heart failure subsequent to myocardial infarction.* European Journal of Heart Failure, 2008. 10(8): p. 733-739). Nonetheless, due to its short half-life (2.7 to 4.5 hours) after subcutaneous injection, it typically requires repeated administrations of high-dose IL-10 to achieve therapeutic potency, leading to increasing risks of side-effects and high treatment cost. Given its high heparin-binding affinity, coacervate may serve as an ideal vehicle for sustained, localized delivery of IL-10 and further reduce the required therapeutic dosage.

Controlled co-delivery of two trophic factors to promote tissue repair has lately been explored. In particular, sustained delivery of FGF2 and hepatocyte growth factor (HGF) via cross-linked albumin-alginate microcapsules augmented angiogenic and arteriogenic responses, improved cardiac perfusion and function, and attenuated cardiac hypertrophy and fibrosis (Banquet, S., et al., *Arteriogenic Therapy by Intramyocardial Sustained Delivery of a Novel Growth Factor Combination Prevents Chronic Heart Failure.* Circulation, 2011. 124(9): p. 1059-1069). Co-delivery of angiogenic FGF-2 and arteriogenic platelet-derived growth factor (PDGF)-BB with self-assembling peptides resulted in reduced infarct size, stable vessel formation, and improvement of cardiac function (Kim, J. H., et al., *The enhancement of mature vessel formation and cardiac function in infarcted hearts using dual growth factor delivery with self-assembling peptides.* Biomaterials, 2011. 32(26): p. 6080-6088). Using a poly(D,L-lactic-co-glycolic acid) microsphere/alginate hydrogel hybrid system, combined delivery of vascular endothelial growth factor (VEGF) and angiopoietin-1 synergistically enhanced vascular maturation and attenuated muscle degeneration at the ischemic site in an murine model hind-limb ischemia, more effective than single factor delivery (Shin, S.-H., et al., *Co-delivery of Vascular Endothelial Growth Factor and Angiopoietin-1 Using Injectable Microsphere/Hydrogel Hybrid Systems for Therapeutic Angiogenesis.* Pharmaceutical Research, 2013. 30(8): p. 2157-2165). On the other hand, our group recently demonstrated that heparin-based coacervate is capable of incorporating and sustaining the release of VEGF and HGF for at least three weeks (Awada, H. K., Johnson, N. R., and Wang, Y., Dual Delivery of Vascular Endothelial Growth Factor and Hepatocyte Growth Factor Coacervate Displays Strong Angiogenic Effects. *Macromolecular Bioscience,* 2014. 14(5): p. 679-686). Dual delivery of VEGF and HGF by coacervate showed stronger angiogenic effects on endothelial cell proliferation and tube formation in vitro than free or coacervate delivery of individual factor (Awada, H. K., Johnson, N. R., and Wang, Y., *Macromolecular Bioscience,* 2014. 14(5): p. 679-686).

It was hypothesize that dual delivery of FGF2 and IL-10 synergistically enhances their angiogenic and/or cardioprotective potency in the ischemic heart. Here, the characterized FGF2/IL-10 coacervate is characterized and its bioactivity on cardiac stromal cells in vitro is investigated. The therapeutic efficacy of FGF2/IL-10 coacervate was evaluated in a mouse AMI model. The data suggest that controlled release of FGF2 and IL-10 by heparin-based coacervate exerts synergistic effects in improving long-term cardiac function, augmenting myocardial elasticity, promoting revascularization, ameliorating myocardial fibrosis, and inhibiting chronic inflammation.

Material and Methods

Preparation of FGF-2/IL-10 Coacervate: Poly(ethylene argininylaspartate diglyceride) (PEAD) was synthesized as previously described. PEAD and clinical-grade heparin (Scientific Protein Labs, Waunakee, Wis., USA) were separately dissolved in 0.9% normal saline (Baxter Healthcare, Deerfield, Ill., USA) at 10 mg ml$^{-1}$ and sterilized by passing through 0.22 µm syringe filter. A 5:1 ratio of PEAD and heparin by weight was used to maintain electric neutrality as previously described [7]. Heparin was first complexed with a pre-determined, equal amount of recombinant human FGF-2 (rhFGF-2; 17.2 kDa protein consisting of 154 amino acid residues) and IL-10 (rhIL-10; 18.6 kDa protein of consisting of 161 amino acid residues) (both from PeproTech, Rocky Hill, N.J., USA) and mixed well. PEAD was subsequently added into the solution containing [heparin: FGF-2/IL-10] complexes. Self-assembly of PEAD and [heparin:FGF-2/IL-10] immediately precipitated the ternary complex out of solution to form the FGF-2/IL-10 coacervate. Precipitation of coacervate complexes immediately increased opaque turbidity in solution. Coacervate was freshly prepared immediately before all in vitro and in vivo experiments to avoid aggregation. Coacervate droplet size was measured by Zetasizer Nano ZS90 (Malvern, Worcestershire, UK) and reported as the mean with polydispersity index (PDI) from 25 measurements. Results were then averaged from measurements of three independent coacervate samples. PDI in the area of light scattering depicts the droplet size distribution.

Fluorescent labeling of FGF-2/IL-10 Coacervate: To fluorescently visualize the incorporation of FGF2 and IL-10 in coacervate complexes, amine-reactive dyes (Thermo Scientific, Waltham, Mass., USA) were utilized to label FGF2 and IL-10 molecules, following the manufacturer's instructions. Briefly, FGF2 and IL-10 solutions were added into vials containing concentrated NHS ester-activated derivatives of DyLight 488 and DyLight 594 respectively and reacted at room temperature for 1 hour. A spin desalting column was used to remove unreacted dyes. To triply label biological components in FGF-2/IL-10 coacervate, FGF2 and IL10 were first labelled with NHS-DyLight 488 and NHS-DyLight 405 individually. FGF2-DL488 and IL-10-DL405 were then mixed well with heparin before rhodamine conjugated *Ulex europaeus* agglutinin I (UEA-1) was applied to label heparin. PEAD was then added into the solution containing [heparin-rhodamine: FGF2-DL488/IL-10-DL405] complexes to form coacervate.

In vitro Release Profile of FGF-2/IL-10 Coacervate: The release profile of FGF2/IL-10 coacervate was determined in vitro as previously described. Briefly, FGF2/IL-10 coacervate was freshly prepared with a mass ratio of PEAD: heparin:FGF2:IL-10=500:100:1:1, using 100 ng each of FGF2 and IL-10. To simulate release of cargo molecules in vivo, additional phosphate-buffered saline (PBS) supplemented with 0.5 U/mL heparinase II was added to each sample to bring up the final volume to 200 µL. Four independent samples were then placed statically in a humidified cell culture incubator at 37° C. At Day 0, 0.5, 1, 4, 7, 10, 14, and 21, samples were pelleted by centrifugation (12,100 g for 10 min), followed by the collection of supernatants. Samples were then replenished with fresh solution and well mixed before being returned to the incubator. Solutions were stored at −80° C. for future analysis. After the final collection on Day 21, samples were replenished with PBS supplemented with 2 U/mL heparinase II and incubated at 37° C. overnight in order to dissociate the remaining coacervate. The amount of FGF2 and IL-10 released into the supernatant was quantified by enzyme-linked immunosorbent assay (ELISA) for FGF2 or IL-10 respectively (both from Abcam, Cambridge, Mass., USA), following the manufacturer's instructions. Supernatants collected from four samples at all-time points were analyzed simultaneously. The absorbance was recorded by SynergyMX (Biotek, Winooski, Vt., USA) or Infinite 200 PRO plate reader (Tecan, Männedorf, Switzerland). Results were averaged. The loading efficiency was determined from the first collection immediately after the initial resuspension (Day 0).

Primary Cell Isolation and Culture: Single donor-derived human umbilical vein endothelial cells (HUVECs) and human cardiac fibroblasts (hCFs) were purchased from Lonza (Allendale, N.J., USA) and respectively expanded in complete endothelial cell growth medium 2 (EGM-2, Lonza) and DMEM high glucose supplemented with 10% fetal bovine serum (FBS) and 1% penicillin-streptomycin (P/S) (all from Life Technologies, Grand Island, N.Y., USA). Mouse cardiac fibroblasts (mCFs) were isolated as previously described (Balasubramanian, S., et al., β3 Integrin in Cardiac Fibroblast Is Critical for Extracellular Matrix Accumulation during Pressure Overload Hypertrophy in Mouse. *PLoS ONE*, 2012. 7(9): p. e45076) and expanded in DMEM high glucose with 10% FBS and 1% P/S. Human heart pericytes (hHPs) were isolated and purified by flow cytometry as we previously reported (Chen, W. C. W., et al., Human Myocardial Pericytes: Multipotent Mesodermal Precursors Exhibiting Cardiac Specificity. *STEM CELLS*, 2015. 33(2): p. 557-573). hHPs were expanded in DMEM high glucose with 20% FBS and 1% P/S. Primary cells at passage 5-7 were used in subsequent experiments.

Measurement of Cell Proliferation in vitro: HUVECs, hCFs, hHPs, and mCFs were trypsinized and plated in triplicate ($1.5 \times 10^3$ cells/well) overnight with 100 µl complete culture media in bottom wells of a HTS transwell-96 well permeable support system (Corning, Tewksbury, MA, USA). Immediately before the transwell support was assembled, all bottom wells were first filled up with 135 µl fresh serum-free basal media (EBM-2 for HUVECs and DMEM for hCFs, hHPs, and mCFs; both supplemented with 1% P/S) with or without 10 ng/ml (for HUVECs) or 100 ng/ml (for all other cell types) of tumor necrosis factor alpha (TNF-α). Free 500 ng FGF2 combined with either 100 ng or 500 ng IL-10 and coacervate containing a fixed load of 500 ng FGF2 alone or combined with either 100 ng or 500 ng IL-10 were resuspended in 75 µl serum-free basal media and then added into transwells. Control transwells were added with plain basal media with or without empty coacervate vehicle. The final concentration of serum was approximately 33% of that in complete culture media in each well. Plates were assembled and subsequently incubated for 72 hours under ambient conditions. After washing all wells, CellTiter 96© AQueous One Solution Cell Proliferation Assay (MTS) reagent (Promega, Madison, Wis., USA) in DMEM was added. The plate was incubated in 5% $CO_2$ at 37° C. for 3 hrs, at which point the absorbance at 490 nm (with reference at 650 nm) was read with Infinite 200 PRO plate reader (Tecan, Männedorf, Switzerland). All experiments were independently repeated 3 times. Results were individually normalized to each experimental control and then averaged.

Experimental Animals: A Total of 77 male BALB/cJ mice at 9-12 weeks old (Jackson Laboratory, Bar harbor, ME, USA) were used for this study.

Intramyocardial Administration of FGF-2/IL-10 Coacervate in a Mouse Model of Acute Myocardial Infarction (AMI): After the induction of anesthesia with 4% isoflurane gas, mice were intubated and inhalationally anesthetized with 2% isoflurane gas throughout the surgery. The induction of myocardial infarction (MI) and intramyocardial injection have been performed as previously reported (Chu, H., et al., *Biomaterials*, 2013. 34(6): p. 1747-1756 and Chen, C.-W., et al., Human Pericytes for Ischemic Heart Repair. *STEM CELLS*, 2013. 31(2): p. 305-316). In brief, MI was microscopically induced by permanent ligation of the left anterior descending coronary artery (LAD). Mice were then randomly assigned to one of the five groups: saline control, FGF2 500 ng coacervate (Coa-F-500), Free FGF2/IL-10 500/500 ng (Free-F/I-500/500), FGF2/IL-10 500/100 ng coacervate (Coa-F/I-500/100), or FGF2/IL-10 500/500 ng coacervate (Coa-F/I-500/500). Five minutes after the induction of MI, free or coacervate FGF2/IL-10 diluted in 30 µl of sterile 0.9% normal saline were injected at three sites of the ischemic myocardium (center and two borders of the infarct). Control mice received injections of 30 µl saline.

Echocardiography: Echocardiographic studies were performed repeatedly before surgery and at 5 days, 2 and 6 weeks post-surgery to assess the cardiac function as we previously described (Chu, H., et al., *Biomaterials*, 2013. 34(6): p. 1747-1756 and Chen, C.-W., et al., *STEM CELLS*, 2013. 31(2): p. 305-316). Briefly, mice were anesthetized with 2% isoflurane gas and immobilized on a heated stage equipped with electrocardiography. Heart and respiratory rates were continuously monitored while the body temperature was maintained at 37° C. Echocardiographic parameters were measured using a high-resolution echocardiography system (Vevo 2100) equipped with a high-frequency linear probe (MS400, 30 MHz) (FUJIFILM VisualSonics, Toronto, Ontario, Canada). Three hundred B-mode frames were acquired at a frame rate of 40 Hz during each scan. End-systolic dimension (ESD) and end-diastolic dimensions (EDD) were determined from the short axis images of the LV and measured from 10 consecutive beats using the M-mode tracing. End-systolic area (ESA) and end-diastolic area (EDA) were measured from short-axis images of the LV. All echocardiographic measurements were taken at the mid-infarct level in LV. Functional parameters, including LV fractional shortening (LVFS), LV fractional area change (LVFAC), and LV ejection fraction (LVEF), were determined as previously described (Manning, W. J., et al., In vivo assessment of LV mass in mice using high-frequency cardiac ultrasound: necropsy validation. *American Journal of Physiology—Heart and Circulatory Physiology*, 1994. 266(4): p. H1672-H1675; Pollick, C., Hale, S. L., and Kloner, R. A., Echocardiographic and cardiac doppler assessment of mice. *Journal of the American Society of Echocardiography*, 1995. 8(5, Part 1): p. 602-610; and Wandt, B., et al., Echocardiographic assessment of ejection fraction in left ventricular hypertrophy. *Heart*, 1999. 82(2):

p. 192-198). Mice died or sacrificed for histological analysis prior to 6 weeks post-injection were not included in the echocardiographic study.

Ultrasonic Analysis of Myocardial Elasticity: The ultrasound in-phase and quadrature (IQ) data were separately acquired at 6 weeks post-MI during the echocardiographic scanning described in the above section (N=3 per group). The IQ data were then converted to the radio frequency (RF) data using standard quadrature sampling algorithms and subsequently analyzed by a blinded investigator. Briefly, pixels were selected in the lateral (infarcted region) and anterior medial (non-infarct region) walls of LV in the first B-mode frame. The 2D phase-sensitive speckle tracking was then applied to the RF data to obtain frame-to-frame axial displacements (direction along the ultrasound beam) of the selected pixels (O'Donnell, M., et al., Internal displacement and strain imaging using ultrasonic speckle tracking. *Ultrasonics, Ferroelectrics, and Frequency Control, IEEE Transactions on*, 1994. 41(3): p. 314-325 and Lubinski, M. A., et al., Speckle tracking methods for ultrasonic elasticity imaging using short-time correlation. *Ultrasonics, Ferroelectrics, and Frequency Control, IEEE Transactions on*, 1999. 46(1): p. 82-96). Axial displacements were accumulated during each cardiac cycle (from diastole to systole). Axial strains in LV wall were obtained by derivative of the accumulated axial displacements. To unbiasedly estimate myocardial elasticity, two regions of interest (ROI) in the axial strain map were respectively selected in the infarcted and non-infarct LV walls. Axial strains in these ROIs were spatially averaged and then normalized by dividing the averaged strain of the infarcted ROI by that of the non-infarct ROI.

Histology and Immunohistochemistry: Mice were sacrificed at 6 weeks post-surgery. Intraventricular injection of 1M potassium chloride (KCl) was performed to arrest hearts in diastole. For histology and immunohistochemistry, harvested hearts were flash frozen in 2-methylbutane (Sigma-Aldrich, St. Louis, Mo., USA) pre-cooled in liquid nitrogen, preserved at −80° C., and then processed as formerly described (Chu, H., et al., *Biomaterials*, 2013. 34(6): p. 1747-1756 and Chen, C.-W., et al., STEM CELLS, 2013. 31(2): p. 305-316). Briefly, frozen hearts were serially cryosectioned at 6-8 μm thickness from apex to the ligation level (approximately 0.5 mm in length). Each series contained 18-21 heart sections and was collected on one glass slide. Hematoxylin and eosin (H&E) staining was performed following the standard protocol. For immunohistochemistry, sections were fixed in a pre-cooled (−20° C.) mixture of methanol and acetone (1:1) for 5 min or in 4% paraformaldehyde for 8 min prior to staining. Non-specific antibody binding was blocked with 10% donkey or goat serum for 1-2 hours at room temperature (RT), and, if necessary, with the Mouse-on-Mouse antibody staining kit (Vector Laboratories, Burlingame, Calif., USA). Sections were incubated overnight at 4° C. with the following primary antibodies (all diluted with 5% donkey or goat serum in PBS): rat anti-mouse CD31 antibody (diluted at 1:100; Becton-Dickinson Biosciences, Franklin Lakes, N.J., USA), mouse anti-mammalian alpha-smooth muscle actin (αSMA)-FITC (diluted at 1:100; Sigma-Aldrich, St. Louis, Mo., USA), and/or rat anti-mouse CD68 antibody (diluted at 1:200; Abcam, Cambridge, Mass., USA). Sections were then incubated at RT for 1 hour with the following fluorochrome-conjugated antibodies: donkey anti-rat-Alexa594 IgG or goat anti-rat-Alexa488 IgG (both diluted at 1:250; Jackson Laboratory, Bar Harbor, Me., USA). Nuclei were stained with 4',6-diamidino-2-phenylindole (DAPI) (1:1000, Life Technologies, Grand Island, N.Y., USA) at RT for 5 min. Immunofluorescent images were taken by Nikon Eclipse Ti fluorescence microscope equipped with NIS-Elements AR imaging software (both from Nikon, Tokyo, Japan).

Measurement of Cardiac Fibrosis and Infarct Wall Thickness: Masson's trichrome staining kit (IMEB, San Marcos, Calif., USA) was used to reveal collagen deposition on heart serial cross-sections, following the manufacturer's instruction. The area of collagen deposition (representing fibrosis/scar) and the area of the entire left ventricular cardiac tissue (including septal area but excluding right ventricle and void space in the chamber cavity) were separately measured using a digital image analyzer (Image J, National Institutes of Health, Bethesda, Md., USA). Fibrotic area fraction was estimated as the ratio of left ventricular fibrotic tissue to the entire left ventricular tissue. Results were averaged from 6 randomly selected sections at comparable infarct levels per heart. Left ventricular wall thickness at the center of the infarct was estimated as the mean of 3 adjacent measurements (0.25 mm apart) and was averaged from 6 randomly selected sections at comparable infarct levels per heart.

Quantification of Chronic Inflammation and Revascularization: To evaluate chronic inflammation within the infarct region, immunofluorescent staining of phagocytic cell marker CD68 was performed on serial cryosections as described above. The infiltration index, represented by the number of CD68+ phagocytic cells per $mm^2$, was subsequently computed by a blinded investigator from 6-8 randomly selected images of the infarct region of each heart at the mid-infarct level, using Image J. To quantify revascularization post-MI, immunofluorescent staining of endothelial cell (EC) marker CD31 and vascular smooth muscle cell (VSMC) marker αSMA was sequentially performed on serial cryosections. The capillary density, represented by the number of CD31+ capillary ECs per $mm^2$, was subsequently computed by a blinded investigator from 6 randomly selected images of the infarct or peri-infarct area of each heart at the mid-infarct level, using Image J as described previously (Chu, H., et al., *Biomaterials*, 2013. 34(6): p. 1747-1756 and Chen, C.-W., et al., *STEM CELLS*, 2013. 31(2): p. 305-316). The VSMC density, represented by the number of perivascular (i.e. adjacent to CD31+ ECs and/or surrounding vascular structures) αSMA+ cells per $mm^2$, was subsequently computed from 6 randomly selected images of the infarct region or peri-infarct area of each heart at the mid-infarct level, using Image J.

Multi-photon Excitation Imaging: For multi-photon excitation (MPE) imaging, rhodamine tagged with UEA-1 (2 μg) was mixed well with heparin before PEAD was added into the solution containing [heparin:rhodamine] complexes to form coacervate. Intramyocardial injection of free or heparin-bound rhodamine-UEA-1 (2 μg) or rhodamine-UEA-1 coacervate (all diluted in 30 μl of sterile 0.9% normal saline) was performed after the induction of MI as described above. Hearts were harvested at 5, 14, and 28 days post-injection, washed 3 times in PBS, and immediately fixed in fresh 4% paraformaldehyde overnight. Hearts were then washed in PBS twice and subsequently immersed in ScaleView-A2 optical clearing agent (Olympus Scientific Solutions Americas, Waltham, Mass., USA) at 4° C. for 7-10 days. Processed hearts were block-sectioned at 1 mm thickness to obtain cross-sections from apex to ligature immediately before performing MPE imaging on an Olympus multiphoton microscope at the Center for Biologic Imaging, University of Pittsburgh.

Statistical Analysis: All measured data are presented as mean±standard deviation (SD). Kaplan-Meier survival curve estimation with log-rank test was performed to compare the animal survival rate between treatment groups. Statistical differences between groups were analyzed by one-way ANOVA (multiple groups) or two-way repeated ANOVA (for repeated echocardiographic measurements) with 95% confidence interval. Statistical significance was set at p≤0.05. Bonferroni multiple comparison test was performed for ANOVA post-hoc analysis. Statistical analyses were performed with SigmaStat 3.5 (Systat Software) and SPSS21 (IBM) statistics software.

Results

Figure 1B:
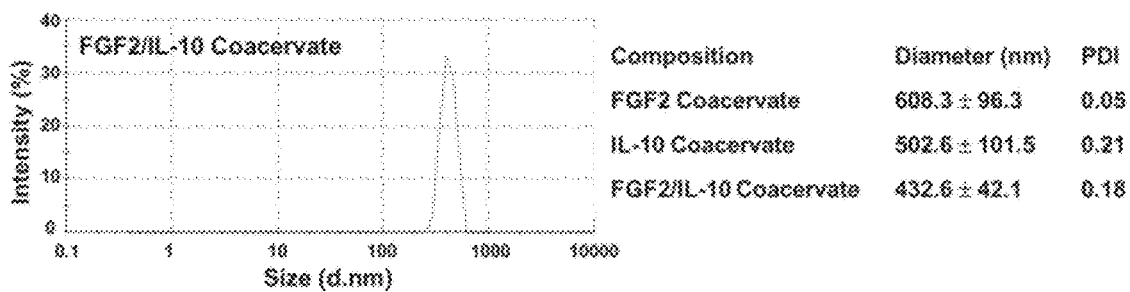

Characterization of FGF-2/IL-10 coacervate: FGF-2 and IL-10 both have high heparin-binding affinity (FGF-2: $K_d \approx 74$ nM [34]; IL-10: $K_d \approx 54$ nM). A mixture of FGF2 and IL-10 is first complexed with heparin and subsequently incorporated into the ternary [PEAD:heparin:FGF2/IL-10] coacervate droplets by adding PEAD. We have theorized that the four structural components of FGF-2/IL-10 coacervate (PEAD, heparin, FGF2, and IL-10) are evenly distributed when the coacervate forms, following affinity-based binding of FGF2 and IL-10 to heparin, charge interactions between PEAD and heparin, and physical entrapment of FGF2 and IL-10 within the complex coacervate (FIG. 1A). FGF2/IL-10 coacervate droplets had an average size of 432.6±42.1 nm in diameter, smaller than the sizes of coacervate droplets containing only FGF2 (608.3±96.3 nm) or IL-10 (502.6±101.5 nm) (FIG. 1B).

Figure 1C:
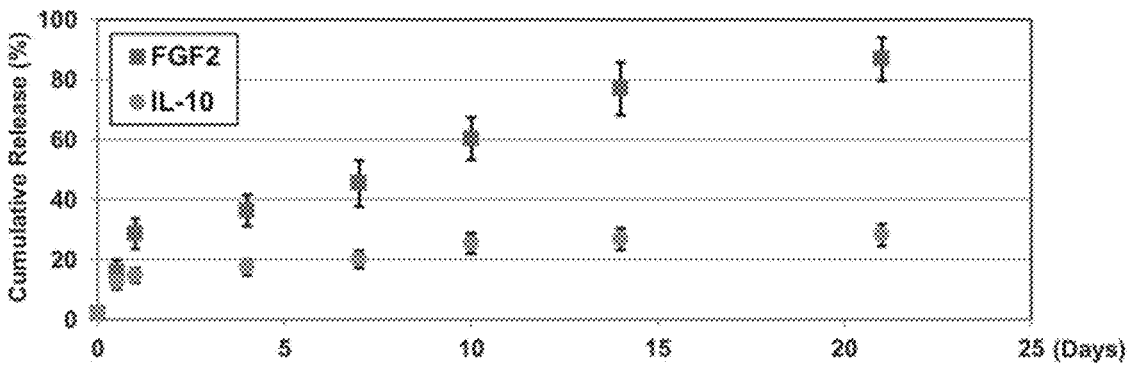
Figure 2:
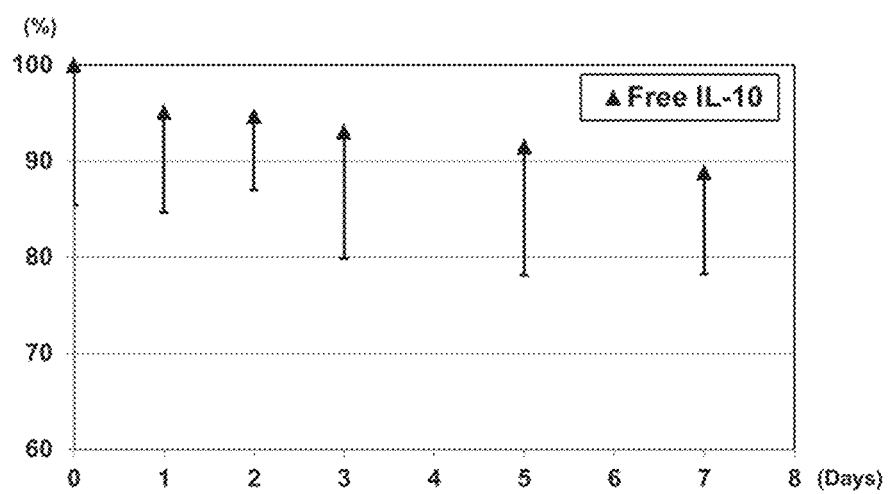
FIG. 2. The spontaneous degradation of free IL-10 in vitro. The degradation profile of free IL-10 (1 µg/mL) in PBS containing 0.5 U/mL heparinase II was measured for 7 days. Supernatants were collected on Day 0, 1, 2, 3, 5, and 7 and stored at −80° C. for simultaneous ELISA analysis (N=4 per time point). A spontaneous loss of free IL-10 was detected at an average rate of 1.59% per day.

To simulate the release of cargo proteins in vivo, the amount of FGF2 and IL-10 released from FGF2/IL-10 coacervate was measured by ELISA after immersion in PBS supplemented with heparinase II (0.5 U/mL) for 0, 0.5, 1, 4, 7, 10, 14, and 21 days (N=4). The loading efficiency of FGF2 and IL-10 was approximately 98.0±1.6% and 97.9±0.5% respectively (FIG. 1C). Cumulatively, FGF2/IL-10 coacervate released roughly 16.1±3.8% and 12.5±2.4% FGF2 and IL-10 respectively during the first 12 hours and approximately 28.7±5.0% and 14.8±2.3% respectively by 24 hours (FIG. 1C). The total release of FGF2 and IL-10 from coacervate was estimated to be 86.8±7.1% and 28.2±3.6% respectively over the 21-day duration (FIG. 1C). Final digestion with 2 U/mL heparinase II showed that at least nearly 3% FGF2 and 15% IL-10 remained in residual coacervate. However, these data did not take into account the spontaneous degradation of free IL-10, on average 1.59% per day, in PBS supplemented with 0.5 U/mL heparinase II (FIG. 2).

Figure 1D:
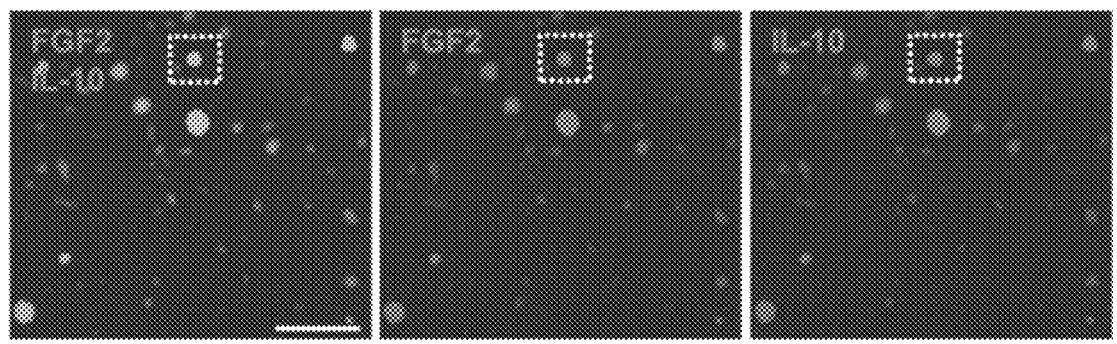
Figure 1E:
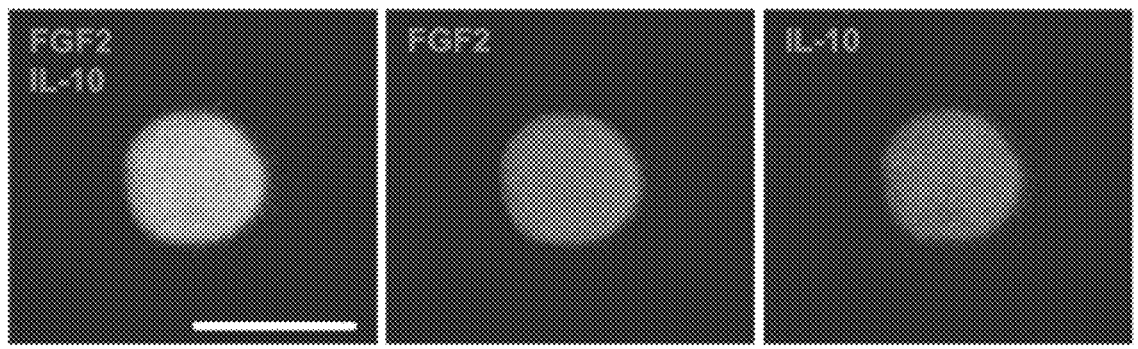
Figure 1F:
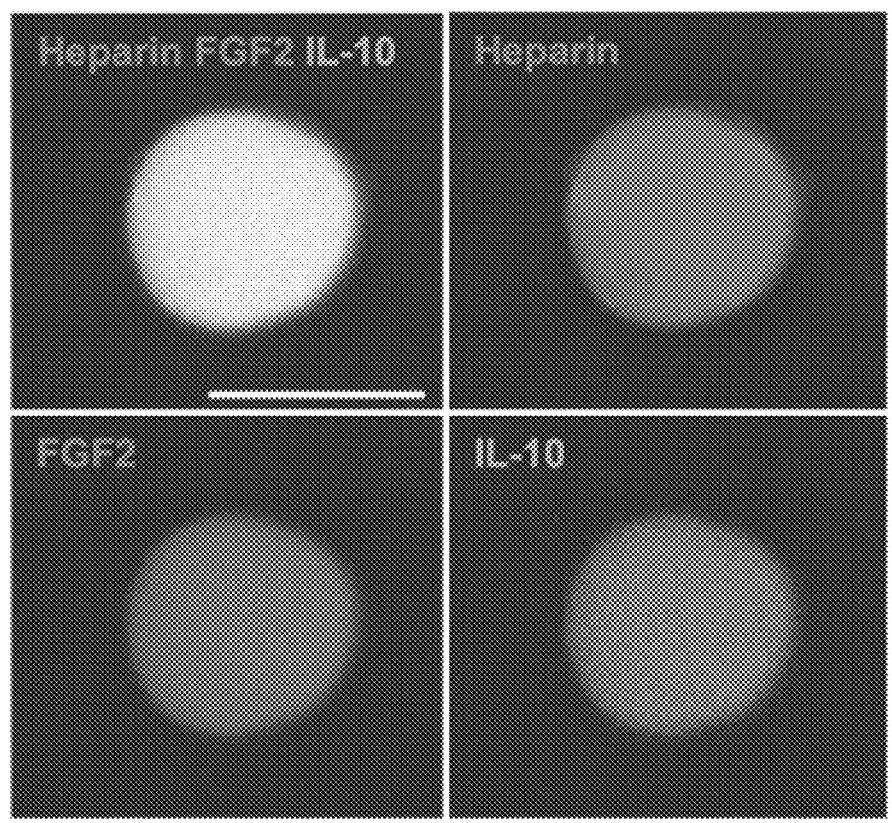

To further demonstrate that FGF2 and IL-10 have been evenly incorporated into coacervate droplets, we fluorescently labeled FGF2 (DyLight 488, green in original) and IL-10 (DyLight 594, red in original). Spherical droplets of different sizes containing FGF-2 and IL-10 were observed following coacervate formation (FIG. 1D). High-magnification confocal microscopy showed an even distribution of FGF-2 and IL-10 molecules within a coacervate droplet (FIG. 1E). By triply labeling heparin (rhodamine, red in original FGF2 (DyLight 488, green in original) and IL-10 (DyLight 405, blue in original), the nearly homogeneous structure of FGF-2/IL-10 coacervate was further revealed (FIG. 1F).

Bioactivity of FGF-2/IL-10 coacervate in vitro: The bioactivity of FGF2/IL-10 coacervate on cardiac stromal cell proliferation was tested in a non-contact release system to avoid direct ingestion of coacervate particles by cells. Cells were cultured at bottom wells with treatment solutions in suspended transwells. Human umbilical vein endothelial cells (HUVECs), human cardiac fibroblasts (hCFs), and human heart pericytes (hHPs), and mouse cardiac fibroblasts (mCFs) were used in this assay. Cells were seeded in complete culture media overnight and then maintained in diluted media throughout the experiment to simulate nutrient starvation following coronary artery blockage. Based on previous study work, we selected a fixed load of FGF2 (500 ng) alone or combined with a low (100 ng) or high (500 ng) load of IL-10 for coacervate delivery (designated as Coa-F-500, Coa-F/I-500/100, and Coa-F/I-500/500 respectively). Free 500 ng FGF2 combined with either 100 ng or 500 ng IL-10 served as positive controls (designated as Free-F/I-500/100 and Free-F/I-500/500 respectively). No treatment (plain or DMEM basal medium) and empty coacervate vehicle groups served as negative controls.

Figure 3:
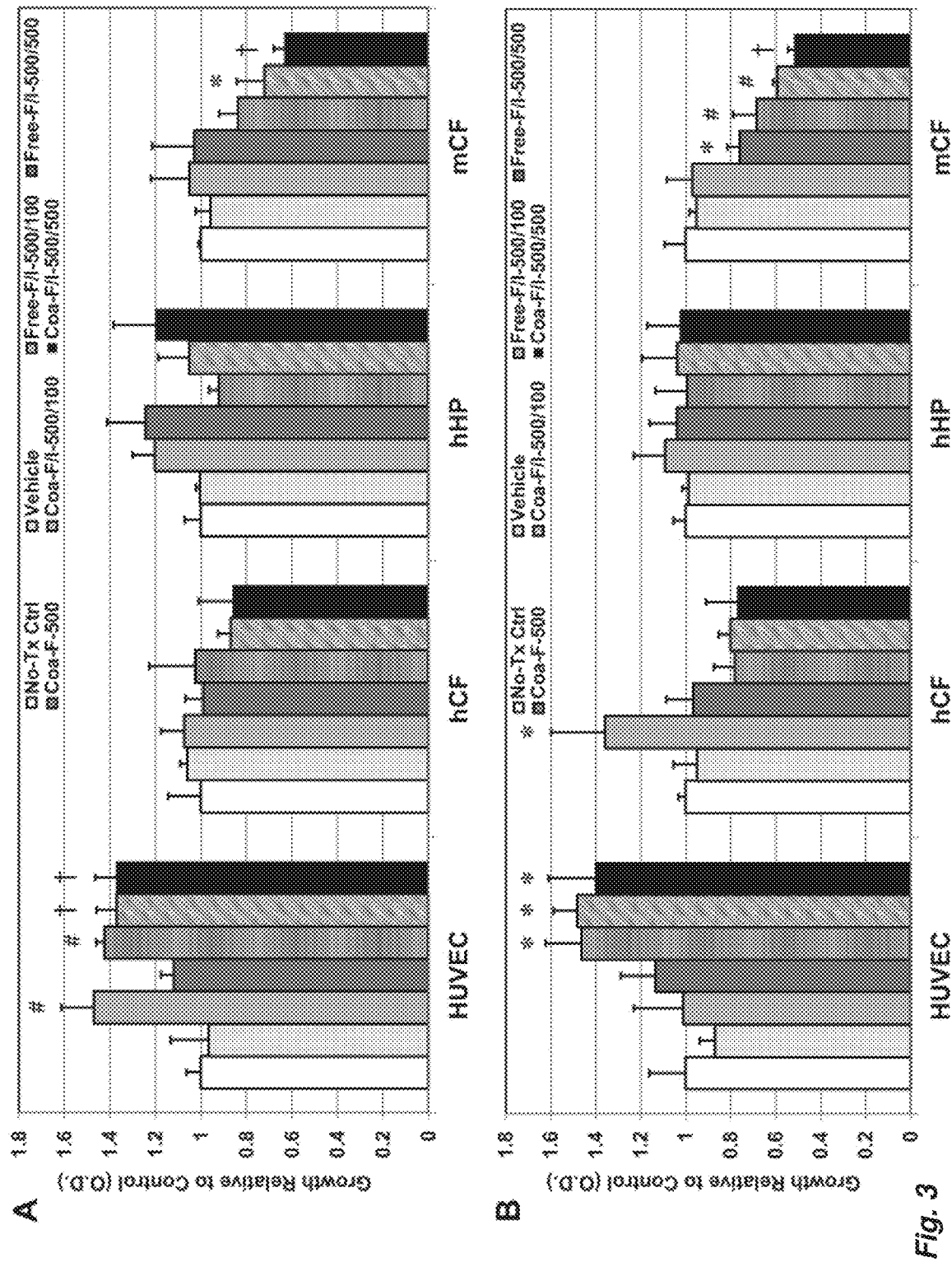
FIG. 3. Bioactivity of FGF-2/IL-10 coacervate on cardiac stromal cell proliferation in vitro. Bioactivity of FGF2/IL-10 coacervate on cardiac stromal cell proliferation was tested in a non-contact transwell system for 72 hours with human umbilical vein endothelial cells (HUVECs), human cardiac fibroblasts (hCFs), and human heart pericytes (hHPs), and mouse cardiac fibroblasts (mCFs) cultured at bottom wells and treatment solutions loaded into suspended transwells. (A) Under the simple serum-deprived condition, Free-F/I-500/100, Coa-F-500, Coa-F/I-500/100 and Coa-F/I-500/500 had significantly higher HUVEC proliferation than the no-treatment control and Free-F/I-500/500. Coa-F/I-500/500 had significantly lower mCF proliferation than the no-treatment control, Free-F/I-500/100, and Free-F/I-500/500 while Coa-F/I-500/100 had significantly lower mCF proliferation than Free-F/I-500/100 and Free-F/I-500/500. Free-F/I-500/100, Free-F/I-500/500, and Coa-F/I-500/500 marginally promoted hHP proliferation (all p>0.05). (B) Under the serum-deprived condition with inflammatory stress (10 ng/ml of TNF-α for HUVECs and 100 ng/ml of TNF-α for all other cell types), Coa-F-500, Coa-F/I-500/100, and Coa-F/I-500/500 had significantly higher HUVEC proliferation than the no-treatment control. Coa-F-500, Coa-F/I-500/100, and Coa-F/I-500/500 had significantly lower hCF proliferation than Free-F/I-500/100. Additionally, Coa-F/I-500/500 had significantly lower mCF proliferation than the no-treatment control, Free-F/I-500/100, and Free-F/I-500/500 while Coa-F-500 and Coa-F/I-500/100 had significantly lower mCF proliferation than the no-treatment control and Free-F/I-500/100. Error bars indicate means±SD. Statistical differences between groups were analyzed by one-way ANOVA with Bonferroni post-hoc analysis. (*p<0.05, †p<0.01, § p<0.005, #p<0.001 in all graphs) (From left-to-right in each group in Figure; No-Tc Ctrl: basal medium; Vehicle: empty [PEAD:heparin]coacervate; Free-F/I-500/100: naked mixture of 500 ng FGF2 and 100 ng IL-10; Free-F/I-500/500: naked mixture of 500 ng FGF2 and 500 ng IL-10; Coa-F-500: coacervate loaded with 500 ng FGF2; Coa-F/I-500/100: coacervate loaded with 500 ng FGF2 and 100 ng IL-10; Coa-F/I-500/500: coacervate loaded with 500 ng FGF2 and 500 ng IL-10)

After incubation for 72 hours, Free-F/I-500/100, Coa-F-500, Coa-F/I-500/100 and Coa-F/I-500/500 significantly increased HUVEC proliferation when compared with the no-treatment control and Free-F/I-500/500 (FIG. 3A, all p<0.01). Coa-F/I-500/100 and Coa-F/I-500/500 showed trends of reducing hCF proliferation and notably inhibited mCF proliferation when compared with Free-F/I-500/100 and Free-F/I-500/500 (FIG. 3A, both p<0.05). Coa-F/I-500/500 demonstrated the most significant inhibition of mCF proliferation when compared with the no-treatment control (p=0.006). On the other hand, Free-F/I-500/100, Free-F/I-500/500, and Coa-F/I-500/500 slightly promoted hHP proliferation (FIG. 3A, all p>0.05). No significant difference was observed between no-treatment control and empty coacervate vehicle group in all four cell types (FIG. 3(A), p>0.05).

To further simulate inflammatory stress following ischemic insult, 10 ng/ml of TNF-α for HUVECs and 100 ng/ml of TNF-α for all other cell types were added into bottom wells immediately before the start of the experiment. After incubation for 72 hours, Coa-F-500, Coa-F/I-500/100 and Coa-F/I-500/500 significantly promoted HUVEC proliferation when compared with the no-treatment control (FIG. 3(B), all p<0.05). All three coacervate groups exhibited reduced hCF proliferation and significantly inhibited mCF proliferation when compared with the no-treatment control and Free-F/I-500/100 (FIG. 3(B), all p<0.01). Similarly, Coa-F/I-500/500 showed the most striking inhibition of mCF growth when compared with all non-coacervate groups (all p<0.01). All treatment groups maintained hHP growth under inflammatory stress (all p>0.05). There was no notable difference between no-treatment and empty vehicle groups under inflammatory stress in all tested cell populations (FIG. 3(B), p>0.05). Altogether these results suggest that FGF2/IL-10 coacervate supports HUVEC growth under nutrient deprivation while inhibiting the proliferation of CFs, especially under inflammatory stress.

Intramyocardial codelivery of FGF-2/IL-10 coacervate synergistically improves cardiac function: We selected 500 ng FGF2 combined with a low (100 ng) or high (500 ng) dose of IL-10 for coacervate-based codelivery (Coa-F/I-500/100 and Coa-F/I-500/500 respectively) and examined the therapeutic efficacy of FGF-2/IL-10 coacervate in vivo. Intramyocardial injection of saline, coacervate containing only 500 ng FGF2 (Coa-F-500), or free FGF-2 500 ng combined with free IL-10 500 ng (Free-F/I-500/500) served as controls. The mortality rate was around 15% during and immediately after the surgery. Among all mice which recovered from the surgery, two died in each of the following groups: Saline, Free-F/I-500/500, and Coa-F-500, and one died in each of the following groups: Coa-F/I-500/100 and Coa-F/I-500/500, before the terminal time point. Most of these deaths occurred within the first week post-surgery. These mice were excluded from functional studies. No significant difference in animal survival rate was noted.

Figure 4A:
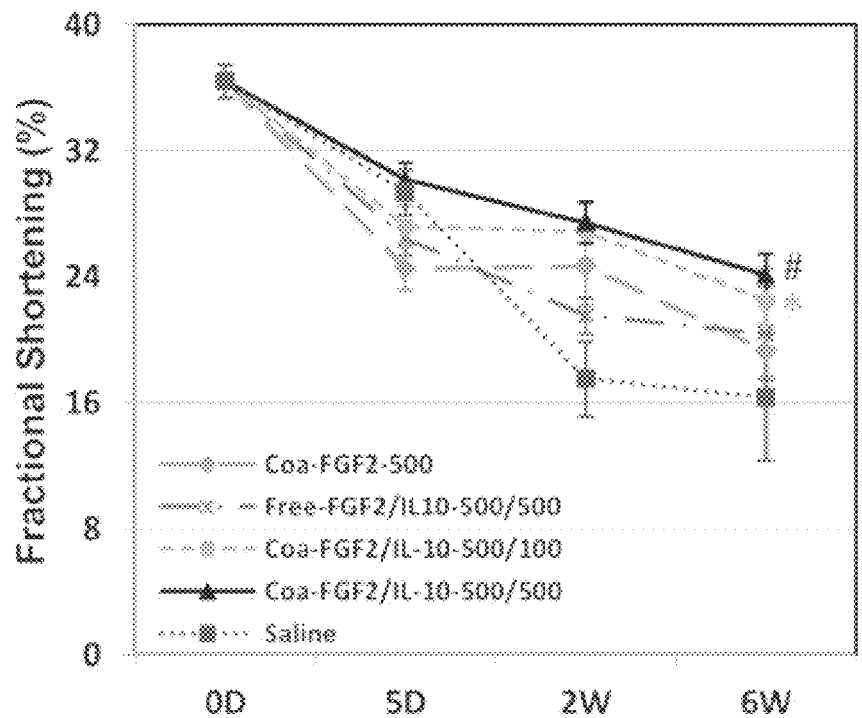
FIGS. 4A-4E. Intramyocardial injection of FGF2/IL-10 coacervate improves long-term cardiac contractility and ameliorates adverse remodeling. Echocardiographic analyses (N=8 per group except Free-F/I-500/500, N=7) were repeatedly performed at 5 days, 2 and 6 weeks post-surgery. Statistical differences in overall treatment effect were analyzed by two-way repeated ANOVA with Bonferroni multiple comparison test. The results revealed substantial improvement in LV contractility following intramyocardial injection of either Coa-F/I-500/100 or Coa-F/I-500/500, as indicated by the higher (FIG. 4A) fractional shortening (FS), (FIG. 4B) fractional area change (FAC), and (FIG. 4C) ejection fraction (EF) (*p<0.05, †p<0.01, § p<0.005, #p<0.001 in all graphs; FS: Coa-F/I-500/100 and Coa-F/I-500/500 vs. Saline, Free-F/I-500/500, and Coa-F-500; FAC and EF: Coa-F/I-500/500 vs. all groups, Coa-F-500 and Coa-F/I-500/100 vs. Saline and Free-F/I-500/500, Free-F/I-500/500 vs. Saline). Significant reductions of (FIG. 4D) end-diastolic area (EDA) and (FIG. 4E) end-systolic area (ESA) of LV were observed in hearts treated with Coa-F/I-500/100 or Coa-F/I-500/500 (*p<0.05, †p<0.01, § p<0.005, #p<0.001 in all graphs; EDA: Coa-F/I-500/500 vs. Saline, Free-F/I-500/500, and Coa-F-500; Coa-F/I-500/100 vs. Saline and Free-F/I-500/500; ESA: Coa-F/I-500/500 vs. Saline, Free-F/I-500/500, and Coa-F-500; Coa-F-500 and Coa-F/I-500/100 vs. Saline and Free-F/I-500/500). Error bars indicate means±SD. Please note that time points on the X-axis (time) in all graphs are not scaled to actual experimental duration.

Cardiac function was assessed by M- and B-mode echocardiography performed repeatedly at the mid-infarct level before (baseline) and after surgery at 5 days, 2 weeks, and 6 weeks (N=8 per group except Free-F/I-500/500, N=7; data analyzed by two-way repeated ANOVA). By analyzing the treatment effect, both FGF2/IL-10 coacervate groups exhibited substantially higher LVFS (FIG. 4A), LVFAC (FIG. 4B), and LVEF (FIG. 4C) than Saline (all p<0.001) and Free-F/I-500/500 (all p<0.05), indicating better LV contractility following controlled release of FGF2 and IL-10. However, only Coa-F/I-500/500, but not Coa-F/I-500/100, showed significant improvement in all three contractile parameters when compared with Coa-F-500 (all p<0.005). Moreover, Coa-F/I-500/500 had significantly better LVFAC and LVEF than Coa-F/I-500/100 (both p<0.05), suggesting a role of IL-10 dosage in prompting a notable synergistic effect for LV contractility.

In addition, ischemic hearts treated with either Coa-F/I-500/100 or Coa-F/I-500/500 had markedly reduced LVEDA (FIG. 4D) and LVESA (FIG. 4E) than Saline (all p<0.001) and Free-F/I-500/500 (all p<0.005), suggesting amelioration of progressive LV dilatation by FGF2/IL-10 coacervate treatment. Similarly, only Coa-F/I-500/500, but not Coa-F/I-500/100, showed significant diminution in both dilatation parameters when compared with Coa-F-500 (all p<0.001), suggesting a role of IL-10 dosage in ameliorating LV remodeling. Overall, our results indicate that the intramyocardial administration of FGF2/IL-10 coacervate, regardless of the IL-10 dose, significantly improved the LV contractile function and reduced the LV dilatation. These data further suggest the importance of IL-10 dosage in the synergistic therapeutic effect induced by FGF2/IL-10 coacervate.

Figure 4B:
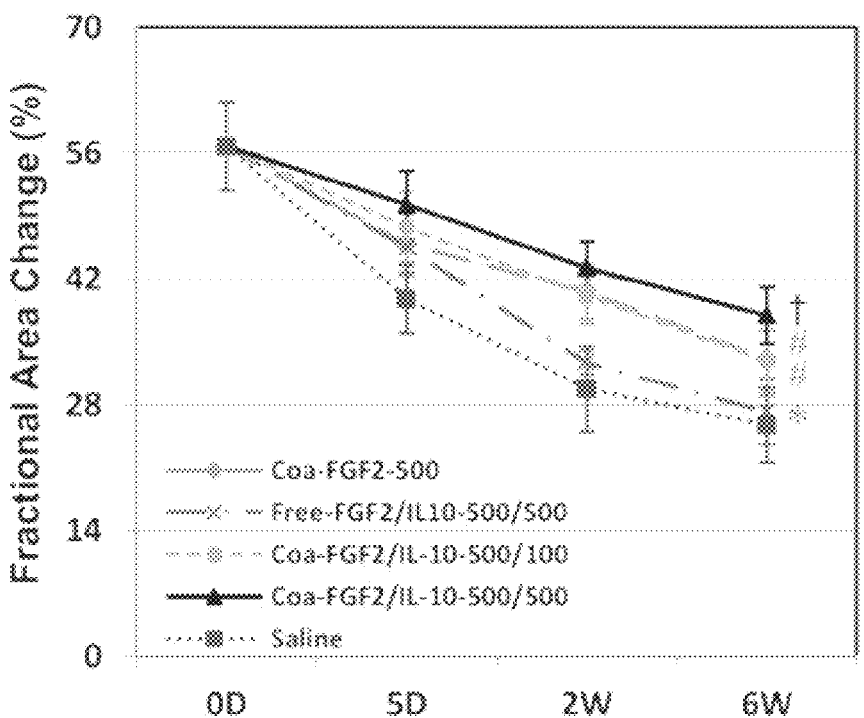
Figure 4C:
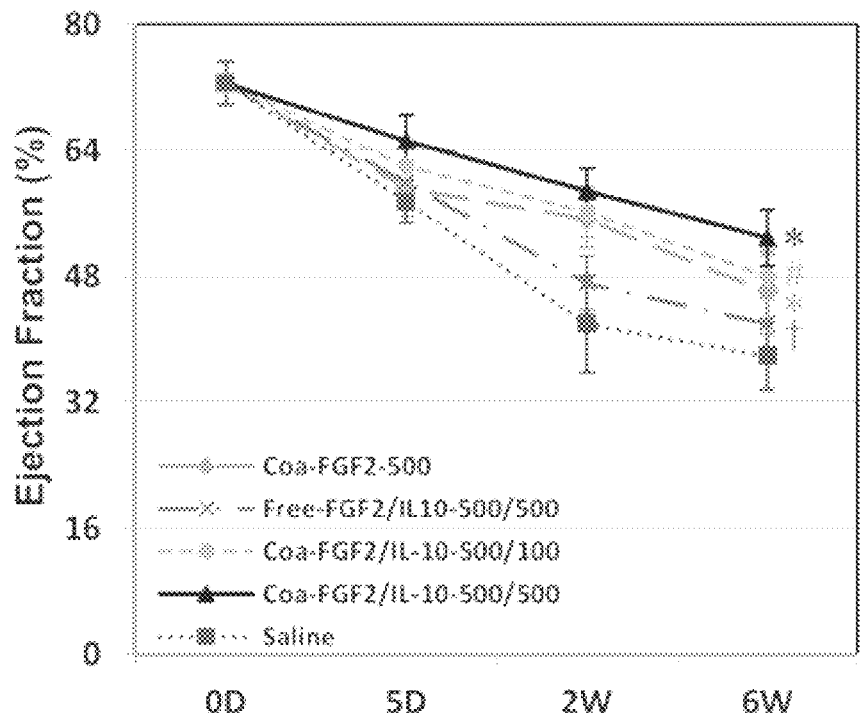
Figure 4D:
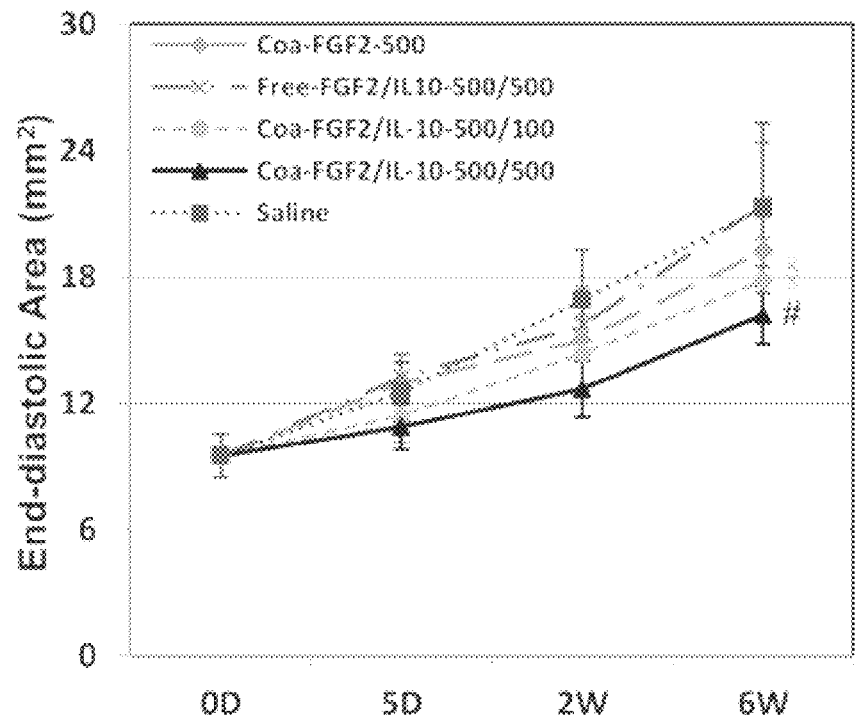
Figure 4E:
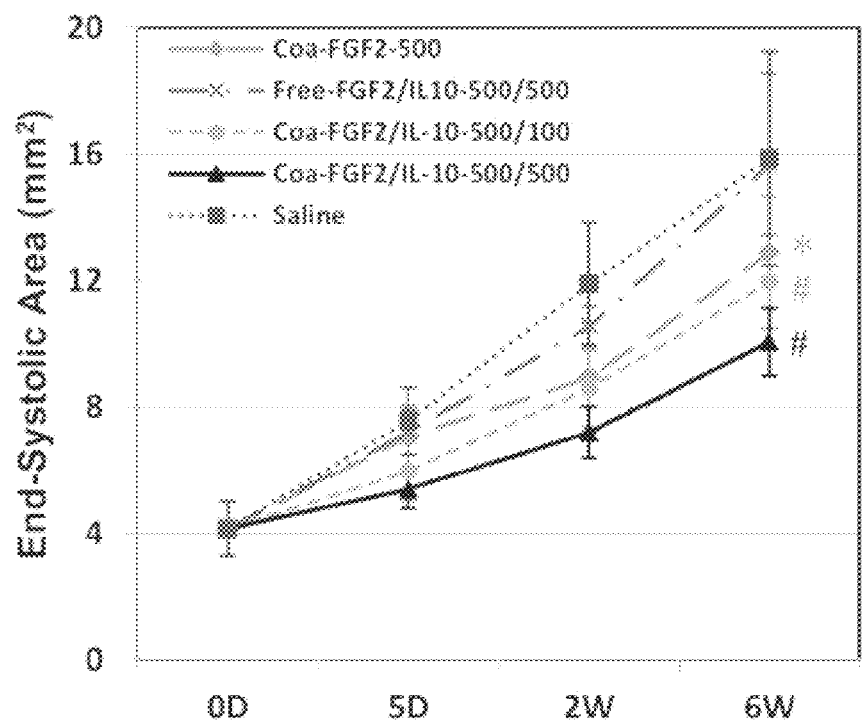
Figure 5A:
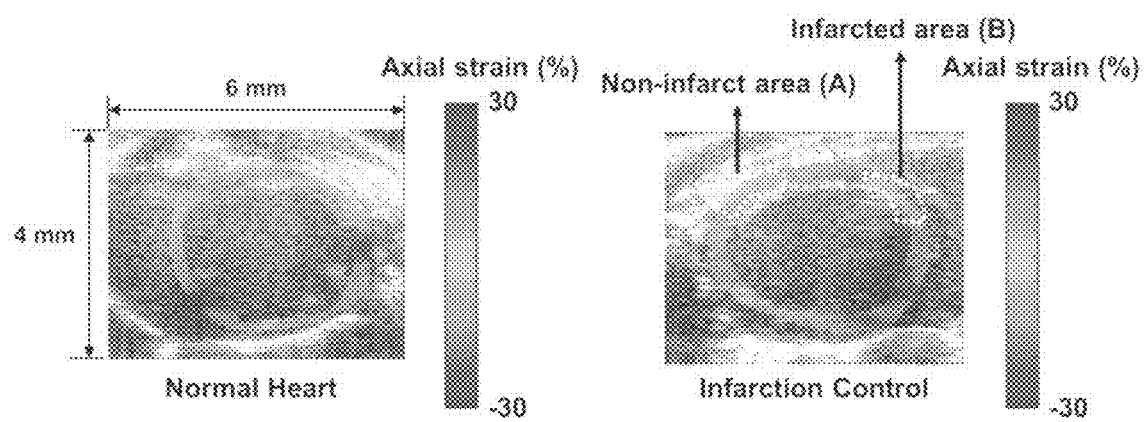
FIGS. 5A and 5B. FGF-2/IL-10 coacervate amends elasticity of infarcted myocardium.
Figure 5B:
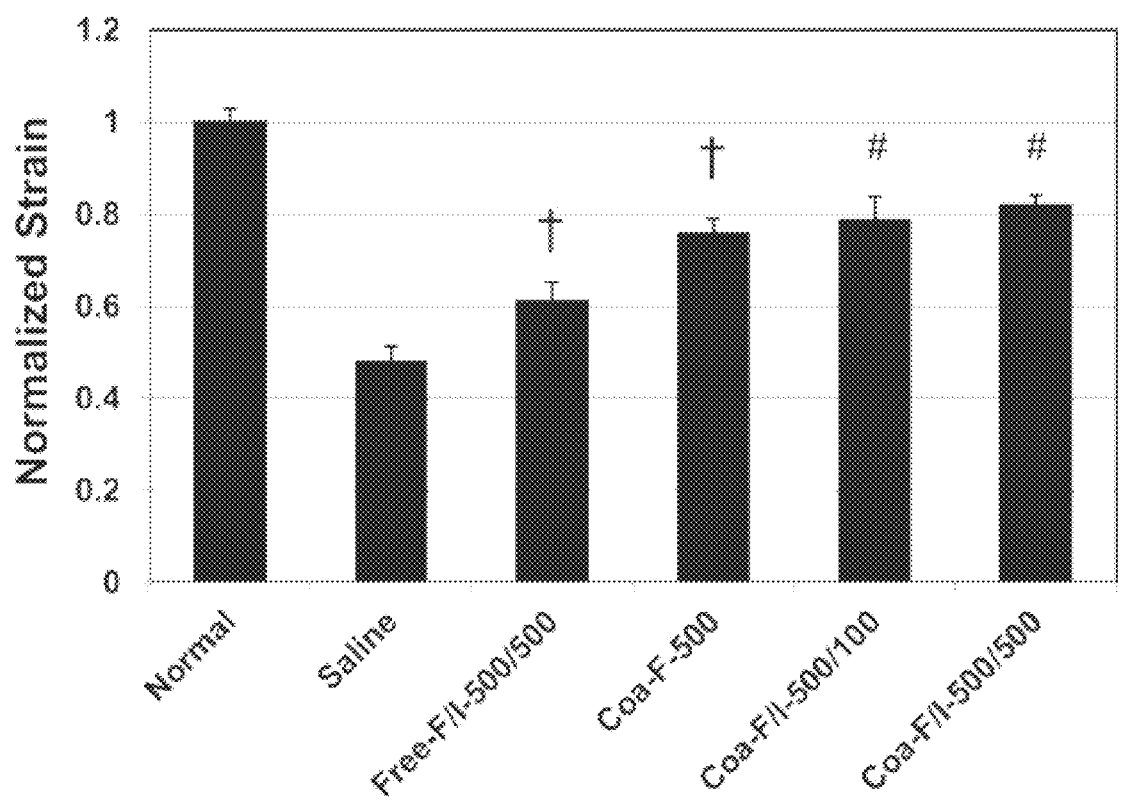
Figure 6:
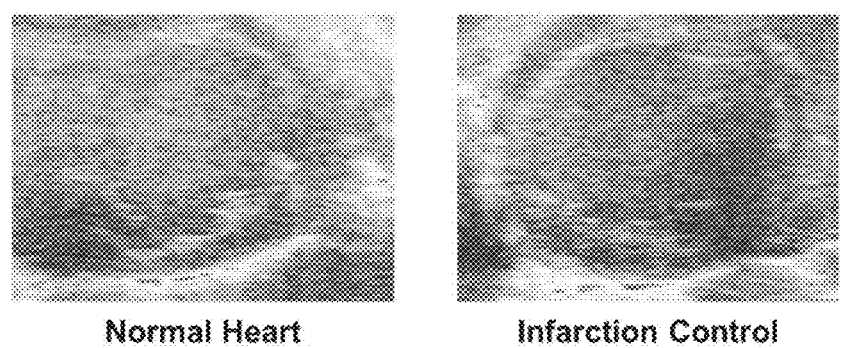
FIG. 6. B-mode images of normal and untreated MI control hearts without strain maps and ROIs.

FGF-2/IL-10 coacervate amends elasticity of the infarcted myocardium: To further assess the effect of FGF2/IL-10 coacervate on myocardial elasticity, we performed ultrasonic strain estimation at 6 weeks post-MI. The axial strains were determined in the infarcted (area B) and non-infarct (area A) LV walls during a cardiac cycle using the 2D correlation based speckle tracking. FIG. 5A shows the axial strain maps of normal (left panel) and untreated MI control (right panel) hearts laid over B-mode images reconstructed from IQ data respectively (negative strains in blue color and positive strains in red). The elasticity of the infarcted myocardium was estimated from spatially averaged axial strains in B and subsequently normalized by dividing the averaged strain of B by that of A (B/A) (FIG. 5A). B-mode images of normal and untreated MI control hearts without strain maps and ROIs are included in FIG. 6 for comparison. While all groups had similar averaged axial strains in A, Coa-F-500 (both p<0.01), Coa-F/I-500/100 (both p<0.001), and Coa-F/I-500/500 (both p<0.001) had significantly greater normalized strains than the saline control and Free-F/I-500/500 (FIG. 4B, N=3 per group). Free-F/I-500/500 also exhibited notably higher normalized strains than the saline control (p=0.004) (FIG. 4B). No significant difference was observed between the three coacervate treatment groups (FIG. 4B, all p>0.05). These data indicate the efficacy of FGF2/IL-10 coacervate in sustaining the long-term LV myocardial elasticity.

Figure 7A:
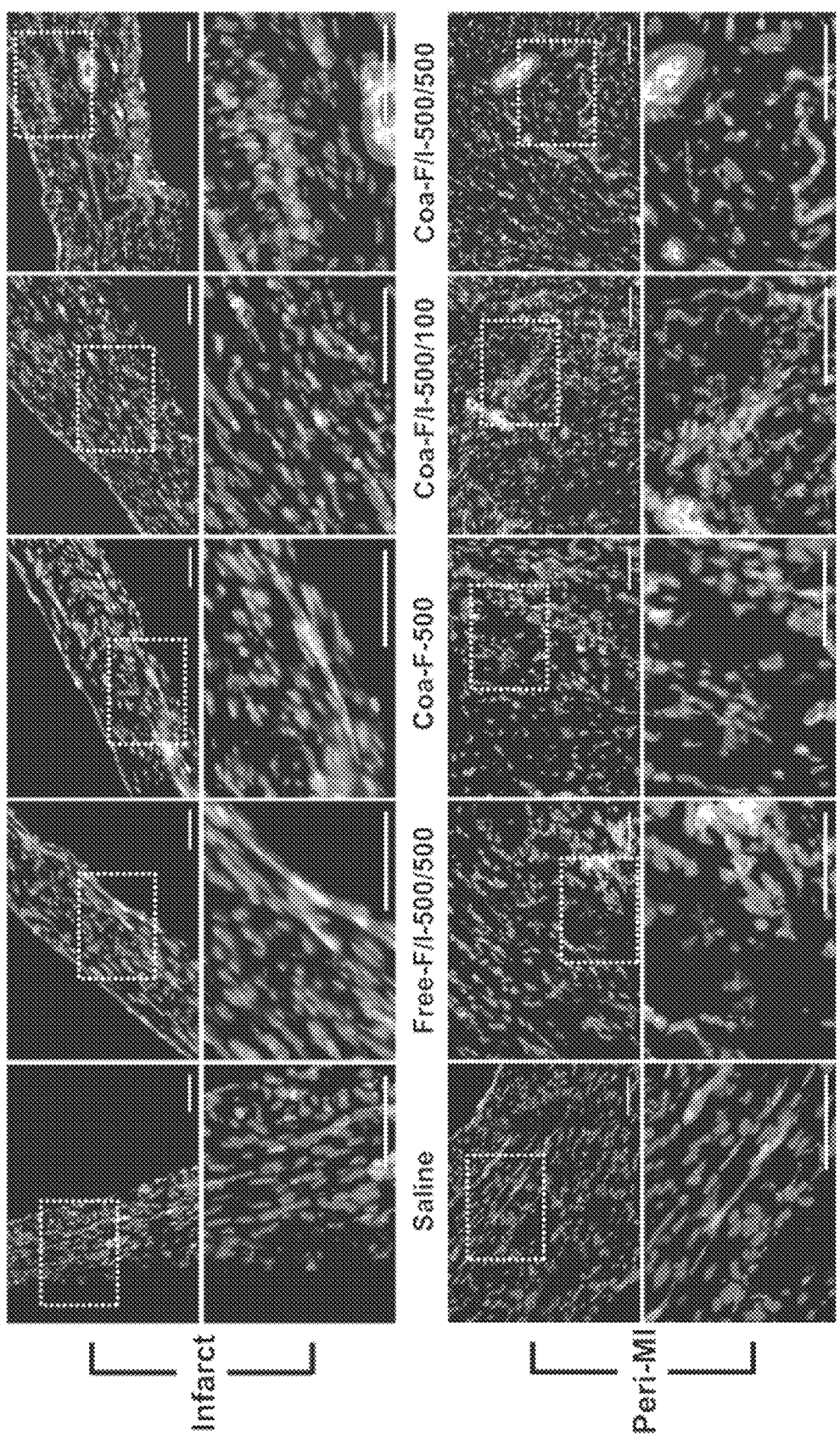
FIGS. 7A and 7B. FGF-2/IL-10 coacervate increases long-term endothelial cell density. Endothelial cell (EC) density at the infarct and peri-infarct border zone was revealed by immunohistochemical detection of CD31+ ECs at 6 weeks post-infarction.
Figure 7B:
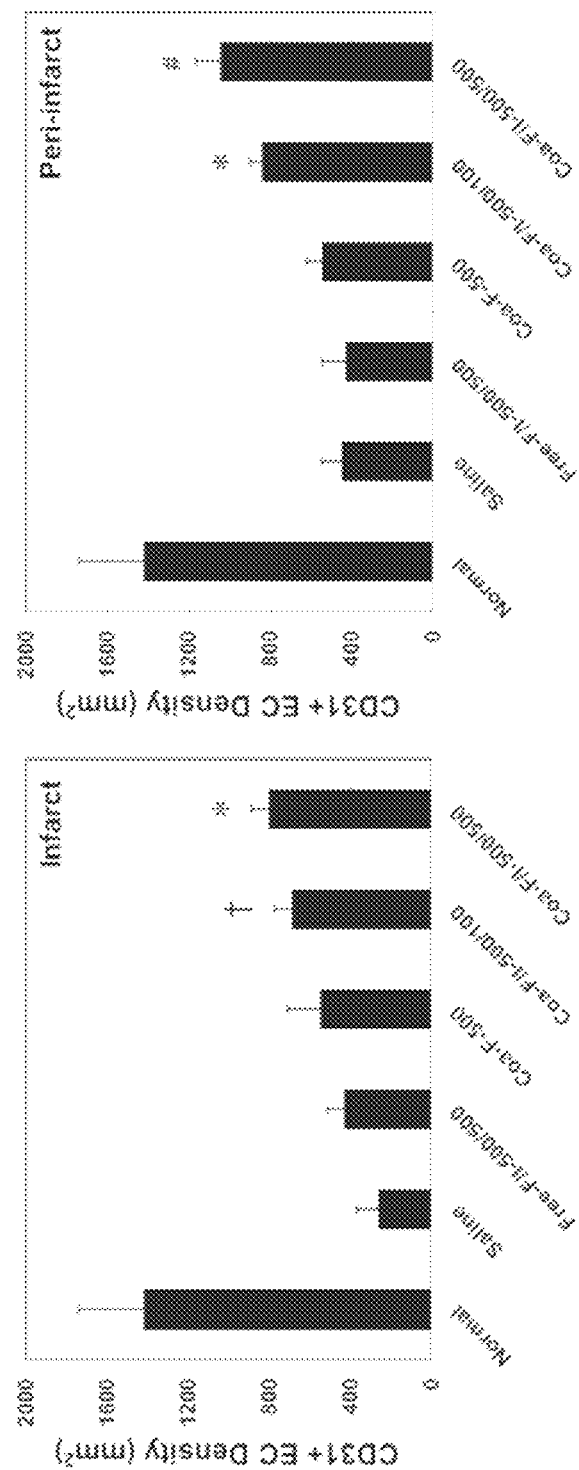
Figure 8:
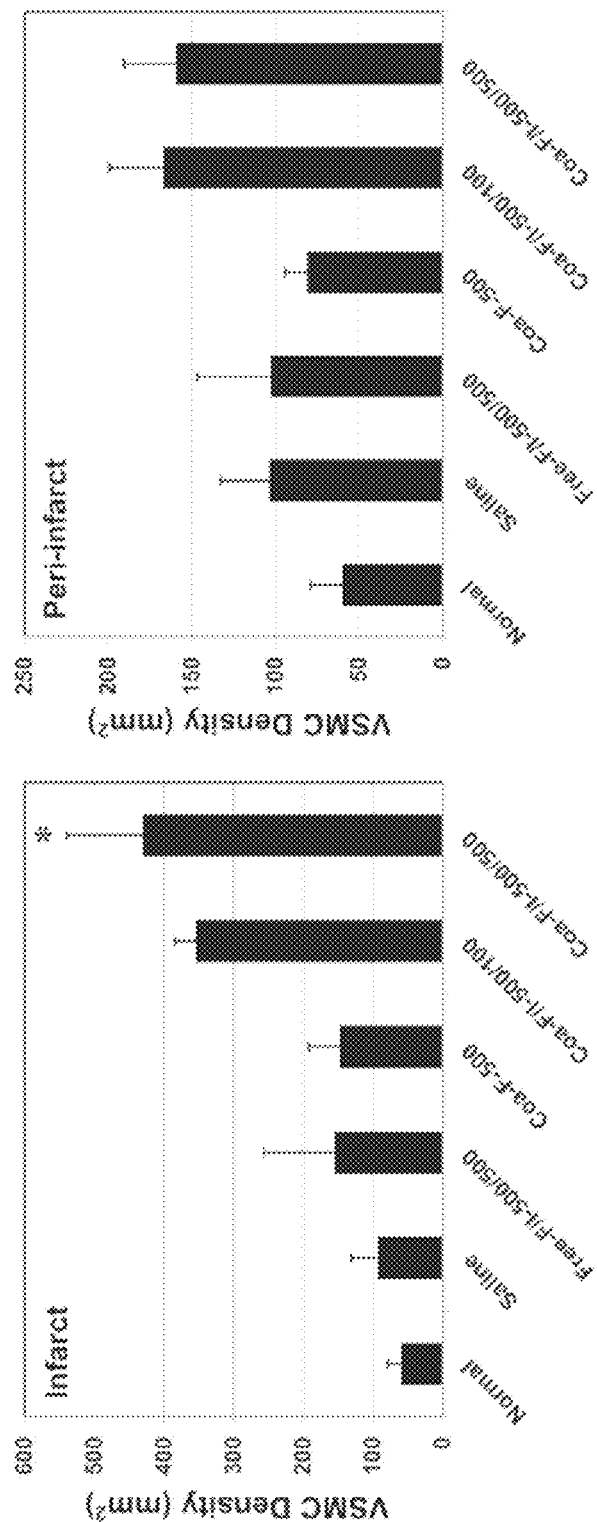
FIG. 8. FGF-2/IL-10 coacervate enhances long-term vascular stromal cell density. Vascular stromal cell density at the infarct and peri-infarct border zone was revealed by immunohistochemical detection of vascular smooth muscle cells (VSMC, defined as perivascular/peri-CD31 αSMA+ cells; representative images shown in FIG. 7(A)) at 6 weeks post-infarction. (left) Quantitative analyses of perivascular αSMA+VSMC density within the infarct area revealed that Coa-F/I-500/500 had significantly higher VSMC density than the saline control, Free-F/I-500/500, and Coa-F-500 (*p<0.05; N=4 per group). (right) Coa-F/I-500/100 and Coa-F/I-500/500 had marginally higher VSMC density than the saline control, Free-F/I-500/500, and Coa-F-500 within the peri-infarct area (all p>0.05; N=4 per group). Error bars indicate means±SD. Statistical differences between groups were analyzed by one-way ANOVA with Bonferroni post-hoc analysis.

FGF-2/IL-10 coacervate promotes long-term revascularization: The potency of intramyocardial administration of FGF2/IL-10 coacervate on long-term revascularization was investigated. Immunohistochemistry revealed the presence of CD31+ endothelial cells (ECs; mostly located at microvasculature/capillary) (FIG. 7A) and vascular smooth muscle cells (VSMC; mostly surrounding larger blood vessels) (FIG. 7A) in the infarct and peri-infarct areas at 6 weeks post-infarction. The number of CD31+ ECs was subsequently quantified in the infarct (FIG. 7B, left) and peri-infarct (FIG. 7B, right) areas (N=4 per group). Within the infarct area, Coa-F/I-500/500 had higher CD31+EC density when compared with the saline control (p<0.001), Free-F/I-500/500 (p=0.02), and Coa-F-500 (p>0.05) (FIG. 7B, left). Coa-F/I-500/100 had higher CD31+EC density when compared with the saline control (p=0.007) and Free-F/I-500/500 (p>0.05) (FIG. 7B, left). Within the peri-infarct area, Coa-F/I-500/500 exhibited the highest CD31+EC density when compared with the saline control (p<0.001), Free-F/I-500/500 (p<0.001), Coa-F-500 (p=0.001), and Coa-F/I-500/100 (p>0.05) (FIG. 7B, right). Coa-F/I-500/100 also had higher CD31+EC density when compared with the saline control (p=0.008), Free-F/I-500/500 (p=0.012), and Coa-F-500 (p>0.05) (FIG. 7B, right). The number of VSMCs and/or pericytes (i.e. perivascular αSMA+ cells) was also quantified in the infarct (FIG. 8, left) and peri-infarct (FIG. 8, right) areas (N=4 per group) at 6 weeks post-infarction. The results showed that Coa-F/I-500/500 had significantly higher VSMC density when compared with the saline control (p=0.008), Free-F/I-500/500 (p=0.038), and Coa-F-500 (p=0.031) within the infarct area (FIG. 8, left). In addition, hearts treated with Coa-F/I-500/100 and Coa-F/I-500/500 exhibited trends of increased VSMCs within the peri-infarct area (FIG. 8, right). Altogether our results suggest FGF2/IL-10 coacervate treatment promotes long-term revascularization at 6 weeks post-infarction, especially with Coa-F/I-500/500 treatment. Additionally, these data imply that the revascularzing effect of FGF2/IL-10 coacervate is positively correlated with the dose of IL-10.

Figure 9:
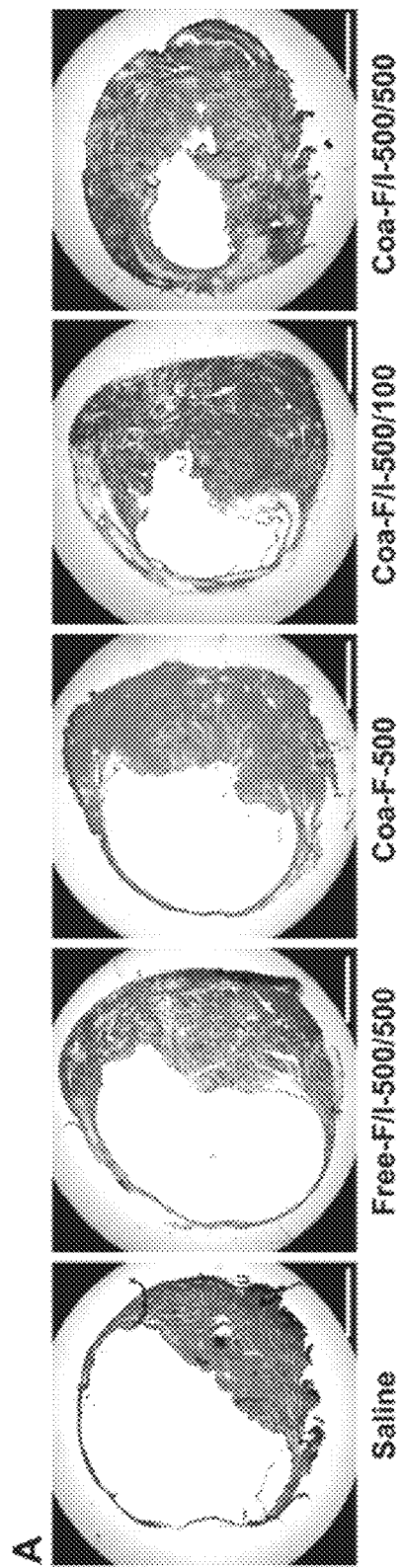
FIG. 9. FGF-2/IL-10 coacervate reduces myocardial fibrosis. Masson's trichrome histological staining was employed to reveal left ventricular (LV) myocardial fibrosis at 6 weeks post-infarction. (A) Representative images of myocardial fibrosis at the mid-infarct level (transverse sections of hearts). Collagen deposition (fibrosis/scar) was stained in blue/purple while cardiac muscle was stained in red (scale bars=1 mm). (B) Quantification of the LV fibrotic area fraction. Coa-F/I-500/500 exhibited significantly reduced LV fibrotic area fraction (#p<0.001, vs. saline; N=4 per group). Healthy heart (Normal) served as a negative control. (C) Measurement of LV wall thickness at the center of the infarct. Coa-F/I-500/500 had significantly thicker infarct wall than all other groups (*p<0.05, vs. all groups; N=4 per group). Error bars indicate means±SD. Statistical differences between groups were analyzed by one-way ANOVA with Bonferroni post-hoc analysis.
Figure 9:
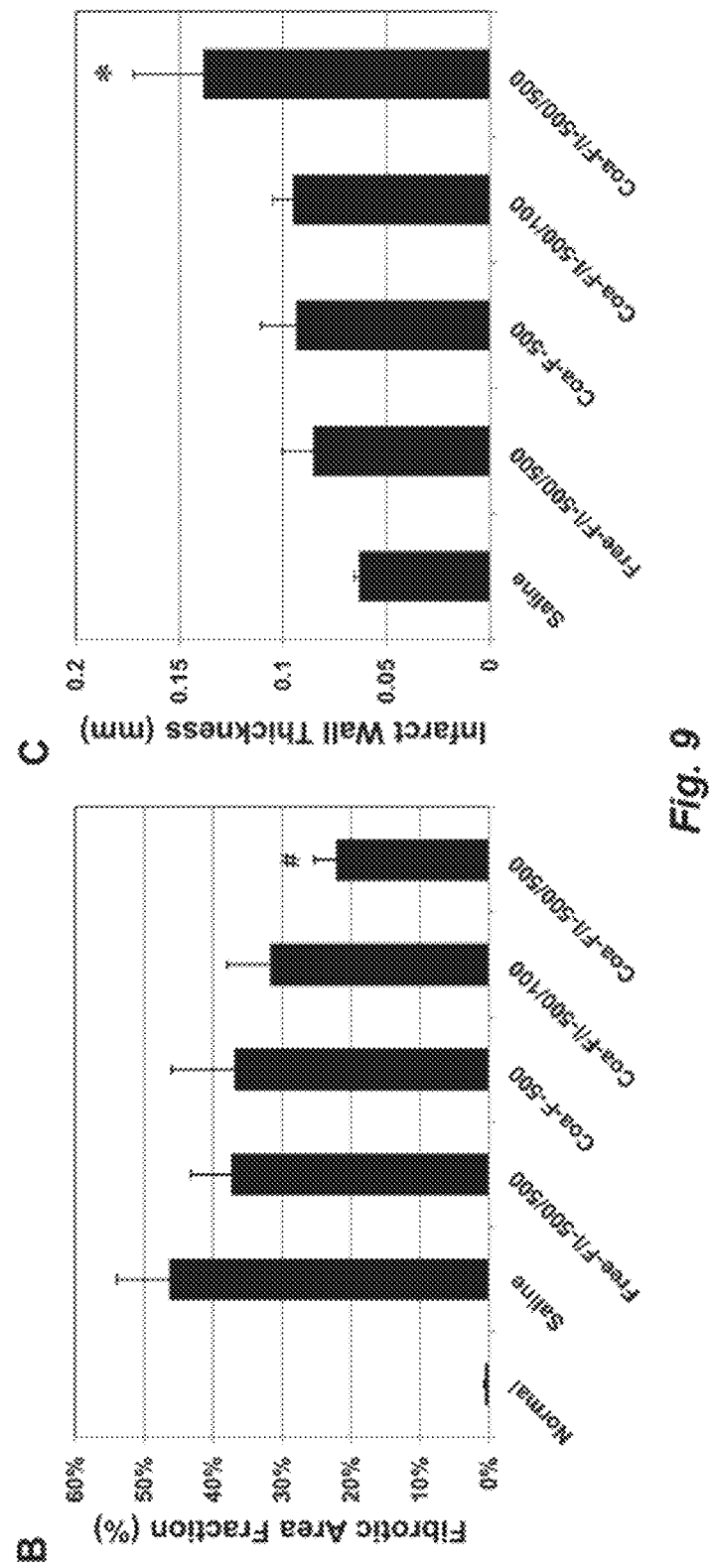

FGF-2/IL-10 coacervate reduces myocardial fibrosis: The effect of FGF2/IL-10 coacervate on long-term LV myocardial fibrosis was evaluated using Masson's trichrome histological staining (collagen deposition stained in blue/purple). At 6 weeks post-infarction, Coa-F/I-500/100 and Coa-F/I-500/500 appeared to have reduced infarct size and scar formation at the mid-infarct level when compared with the saline control and Free-F/I-500/500 (FIG. 9(A)). Quantitative analysis revealed that Coa-F/I-500/500 exhibited notably smaller LV scar fraction than the saline control (p=0.001) and all other treatment groups (all p>0.05) (FIG. 9(B), N=4 per group). Analysis of the LV wall thickness at the infarct center further showed that Coa-F/I-500/500 had a significantly thicker wall than the saline control (p<0.001) and all other test groups (all p<0.05) (FIG. 9(C), N=4 per group). These data suggest the efficacy of coacervate containing higher dose of IL-10 in ameliorating the formation of myocardial fibrosis and preserving wall thickness post-infarction.

Figure 10:
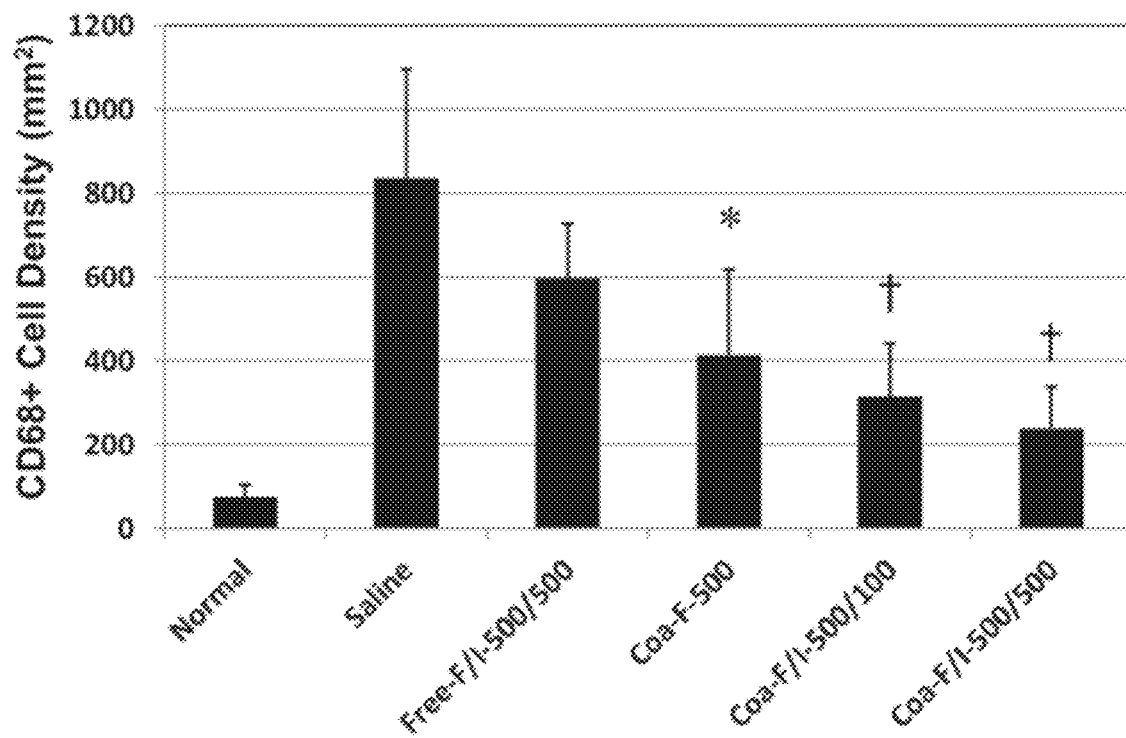
FIG. 10. FGF-2/IL-10 coacervate inhibits chronic phagocytic cell infiltration The effect of FGF-2/IL-10 coacervate on chronic inflammatory responses was evaluated by the number of focally infiltrating CD68+ phagocytic cells within the infarct region at 6 weeks post-infarction. When compared with the saline control, Coa-F-500, Coa-F/I-500/100, and Coa-F/I-500/500 had significantly reduced numbers of infiltrated CD68+ phagocytic cells within the infarct area. Error bars indicate means±SD. Statistical differences between groups were analyzed by one-way ANOVA with Bonferroni post-hoc analysis. (*p<0.05, †p<0.01, vs. saline; N=4 per group).

FGF-2/IL-10 coacervate inhibits chronic phagocytic cell infiltration: To investigate the underlying mechanism for the amelioration of myocardial fibrosis, we examined the anti-inflammatory effect of FGF2/IL-10 coacervate. Phagocytic cells within the infarct area were detected by anti-CD68 immunohistochemistry at 6 weeks post-infarction. All three coacervate groups showed significantly decreased numbers of infiltrated CD68+ phagocytic cells within the infarct area when compared with the saline control (FIG. 10, N=4 per group; Coa-F-500, p=0.037; Coa-F/I-500/100, p=0.007; Coa-F/I-500/500, p=0.002). In particular, Coa-F/I-500/100 and Coa-F/I-500/500 exhibited substantial 47.2% and 59.9% reduction of CD68+ cells respectively when compared with Free-F/I-500/500 (FIG. 10, both p>0.05). Although there is no statistical significance in the number of CD68+ cells between all three coacervate groups, comparing with Coa-F-500, Coa-F/I-500/100 and Coa-F/I-500/500 displayed notable 23.9% and 42.3% diminution of CD68+ cells respectively. Together these results suggest that coacervate delivery of FGF2 and IL-10 increases their long-term potency for immunoregulation, and the addition of IL-10 in FGF2 coacervate augments the inhibition of chronic inflammation.

Figure 11:
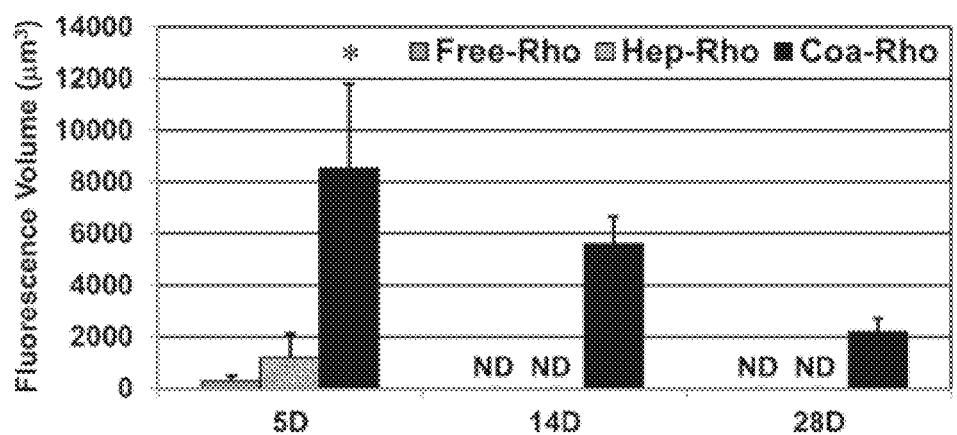
FIG. 11. Estimation of the duration of coacervate treatment in vivo. Multi-photon excitation (MPE) imaging was employed to detect intramyocardially injected free (Free-Rho), heparin-bound (Hep-Rho), or coacervate-bound rhodamine (Coa-Rho). Collagen fibers (blue in original) were revealed by second harmonic generation (SHG) signals. Quantification of the fluorescence volume of Free-Rho, Hep-Rho, and Coa-Rho at 5, 14, and 28 days post-injection. Error bars indicate means±SD. Statistical differences between groups were analyzed by one-way ANOVA with Bonferroni post-hoc analysis. (*p<0.05, vs. Free-Rho and Hep-Rho; N=3 per group).

Estimation of the duration of coacervate treatment in vivo: To estimate the duration of coacervate treatment post-MI, we employed multi-photon excitation (MPE) imaging to detect intramyocardially injected rhodamine-tagged coacervate (Coa-Rho). Collagen fibers were identified by second harmonic generation (SHG) signals. At 5 days after injection, Coa-Rho exhibited robust fluorescent signals within the infarct area while weak signals were detected in free (Free-Rho) or heparin-bound (Hep-Rho) rhodamine injected hearts. At 2 and 4 weeks post-MI, fluorescent signals were only detected in hearts injected with Coa-Rho, but not with Free-Rho or Hep-Rho. No signal was detected in any group at 6 weeks post-MI. Quantification of the fluorescence volume found that at 5 days post-injection, Coa-Rho had 28.9±11.1 and 7.1±2.7 folds higher signals than that of Free-Rho and Hep-Rho respectively (FIG. 11, N=3 per group, p<0.05). Moreover, when compared with the signal on Day 5, Coa-Rho had roughly 65.9% and 25.7% of residual fluorescence volume at 2 and 4 weeks post-injection respectively (FIG. 11, N=3 per time point). These results suggest a temporal distribution and progressive degradation of coacervate for at least 4 weeks in situ in infarcted hearts.

Discussion

Molecular therapy using trophic factors to promote cardiac repair and regeneration has been widely investigated. To promote revascularization in the ischemic myocardium, angiogenic GFs such as FGF2 and VEGF have been successfully tested in pre-clinical models of MI. However, clinical attempts using angiogenic GFs have demonstrated mixed results (Segers, V. M. and Lee, R., Protein Therapeutics for Cardiac Regeneration after Myocardial Infarction. *Journal of Cardiovascular Translational Research*, 2010. 3(5): p. 469-477). One major obstacle of molecular therapy with exogenous GFs and/or cytokines is the short in vivo half-life of most biological factors. In addition, the bioavailability of systemically delivered trophic factor(s) in the target tissue/organ varies dramatically, highly dependent on the availability of local vasculature. These shortcomings have led to common administrations of large, repetitive doses of GFs in order to achieve therapeutic efficacy, thus increasing the risk of on-target and/or off-target side effects. For example, VEGF can induce nitric oxide-mediated hypotension when a dose over 50 ng/kg/min is administered by intracoronary infusions in patients with myocardial ischemia (Henry, T. D., et al., Intracoronary administration of recombinant human vascular endothelial growth factor to patients with coronary artery disease. *American Heart Journal*, 2001. 142(5): p. 872-880). To effectively augment the local bioavailability and potency of exogenous trophic factor(s) and minimize the required therapeutic dosage in the context of ischemic insult, a suitable vehicle for sustained, localized delivery is critically needed.

Here, nearly even incorporation and homogeneous distribution of FGF2 and IL-10 is shown within coacervate droplets. FGF2/IL-10 coacervate not only had high loading efficiencies for FGF2 and IL-10 (approximately 98% for both) but also exhibited low initial releases of around 16.1% FGF2 and 12.5% IL-10 in the presence of heparinase during the first 12 hours and relatively linear releases of both factors thereafter throughout 21 days. The seemingly low cumulative release of IL-10 was primarily due to the spontaneous degradation of released IL-10 and molecules trapped in residual coacervate. Coacervate delivery of FGF2 and IL-10 preserved their bioactivities on cardiac stromal cell proliferation in vitro. FGF2/IL-10 coacervate sustained HUVEC and hHP proliferation while reducing CF proliferation in general, especially under the inflammatory stress condition.

Hearts treated with FGF2/IL-10 coacervate, Coa-F/I-500/500 in particular, exhibited significantly improved long-term LV contractile function and ameliorated LV dilatation, suggesting the synergistically therapeutic efficacy by controlled delivery of FGF2 and IL-10. FGF2/IL-10 coacervate, especially Coa-F/I-500/500, augmented long-term revascularization, particularly at the infarct area. The data provided in this Example also imply a positive correlation of revascularizing effects with the dose of IL-10. In addition, coacervate containing FGF2 and 500 ng IL-10 reduced LV fibrosis, preserved infarct wall thickness, and inhibited chronic phagocytic cell infiltration at the infarct area, more effective than coacervate loaded with FGF2 alone. These results further suggest the synergistic effects of coacervate with FGF2 and IL-10 in anti-fibrosis and anti-inflammation.

Figure 12:
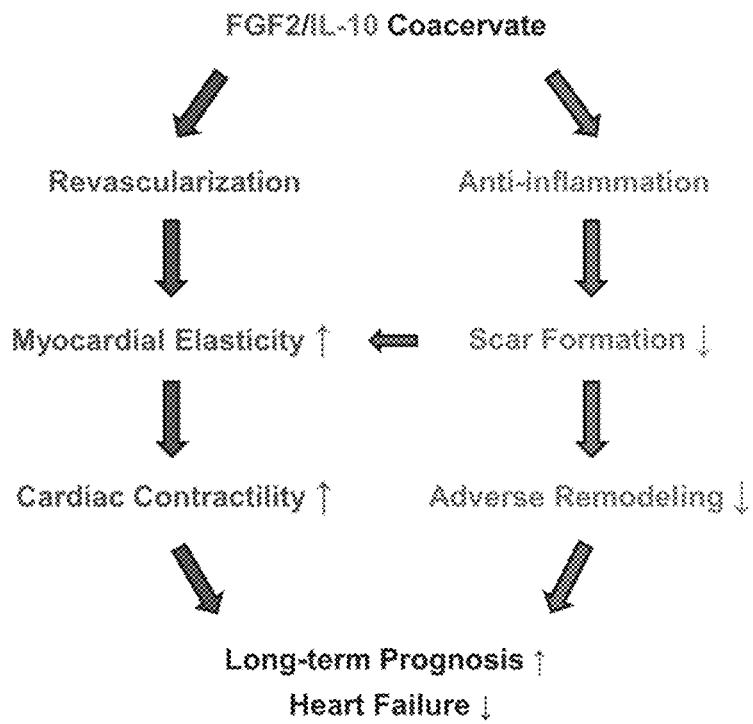
FIG. 12 depicts postulated mechanisms of FGF-2/IL-10 coacervate-mediated cardiac repair and functional recovery.

Moreover, Coa-F/I-500/100 and Coa-F/I-500/500 had substantially augmented long-term LV myocardial elasticity, maintaining around 80% of the normal myocardial strain. Interestingly, Coa-F-500 treated hearts also exhibited significantly increased myocardial elasticity. These data suggest the primary effect of controlled, localized delivery of FGF2 on myocardial elasticity, largely independent of IL-10 mediated anti-inflammatory benefits. This is likely attributed to the enhanced functional revascularization and reduced cardiomyocyte death mediated by controlled release of FGF2-Putative mechanisms involved in FGF2/IL-10 coacervate mediated ischemic heart repair are summarized in FIG. 12.

The estimation of the duration of coacervate treatment post-MI by MPE imaging indicates that injected coacervate had a temporal distribution of at least 4 weeks in situ. Consequently, FGF2, IL-10, or other therapeutic proteins with high heparin affinity will likely persist within coacervate and increase their long-term bioavailability in the local tissue.

Overall, Coa-F/I-500/500 exhibited the highest therapeutic potential among all treatment groups. This warrants the pre-clinical translation of coacervate delivery of FGF2 in combination with IL-10 in large animal models. In addition, the application of FGF2/IL-10 coacervate for the treatment of other ischemic conditions such as myocardial reperfusion injury and peripheral artery disease demands future investigation. Currently we are investigating the dose-dependent effect(s) and the precise mechanism(s) of anti-inflammation and immunomodulation mediated by controlled release of IL-10.

In summary, heparin-based coacervate represents a promising vehicle for localized, controlled delivery of a combination of angiogenic and anti-inflammatory proteins. A single coacervate treatment with 500 ng each of FGF2 and IL-10 resulted in long-term synergistic benefits in a mouse MI model. Future study in pre-clinical large animal models is warranted to evaluate its therapeutic potential for the treating ischemic heart disease. Given that heparin binds a wide range of trophic factors, coacervate delivery of single or multiple therapeutic proteins can be further expanded to applications in different pathological conditions.

Example 5—Treatment of Melanoma

Twenty four (24) C57BL/6 female mice were divided into three treatment groups: 1) protein coacervate; 3 doses; 2)

Blank coacervate, and PBS (phosphate-buffered saline), n=4 for each group. Ten days prior to the first treatment, the mice were each inoculated with cells in saline at two sites, one in each leg. Mice were randomized into groups and treated with 1st injection in only one leg (primary site). A second treatment was given seven (7) days subsequent to the first treatment. 50 µL injection per mouse per treatment consists of 25 µL of IL-2 or IL-12, and 25 µL of 3.75 mg coacervate. IL-2 (interleukin-2, purchased from PeproTech, Rocky Hill, N.J.) in 10 mM sodium citrate buffer with 0.1% BSA was dosed at 0.01 µg, 0.1 µg, and 1 µg per dose and mixed with 1.78 µL of 150 mg/mL heparin in 0.9% saline and 23.22 µL of 150 mg/mL PEAD in 0.9% saline. IL-12 (interleukin-12, purchased from PeproTech, Rocky Hill, N.J.) in 1.5×PBS with 0.1% BSA was dosed at 1 µg, 10 µg, and 30 µg per dose and mixed with heparin and PEAD in the same manner as IL-2 coacervates. Tumor size was determined for each time point, and blood was collected for analysis (TBD).

Figure 13:
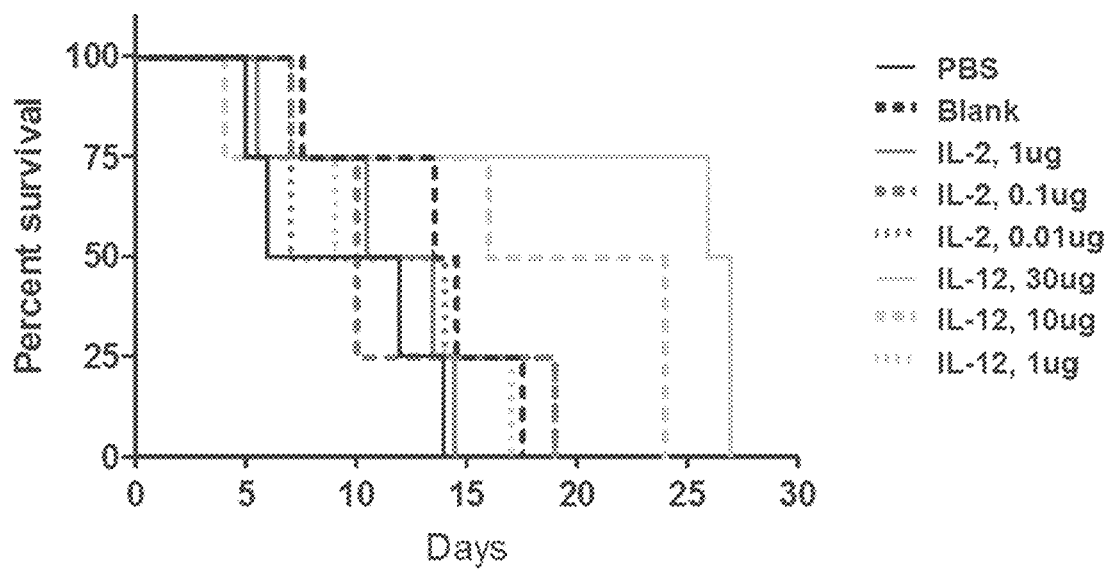
FIG. 13 is a graph depicting survival proportions as described in Example 5.
Figure 14:
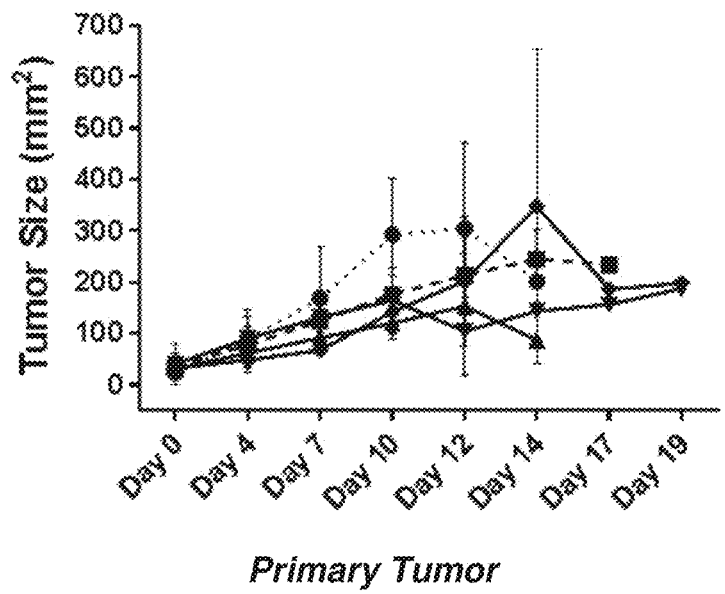
FIG. 14 provides graphs showing a summary of results for Example 5 (IL-2).
Figure 14:
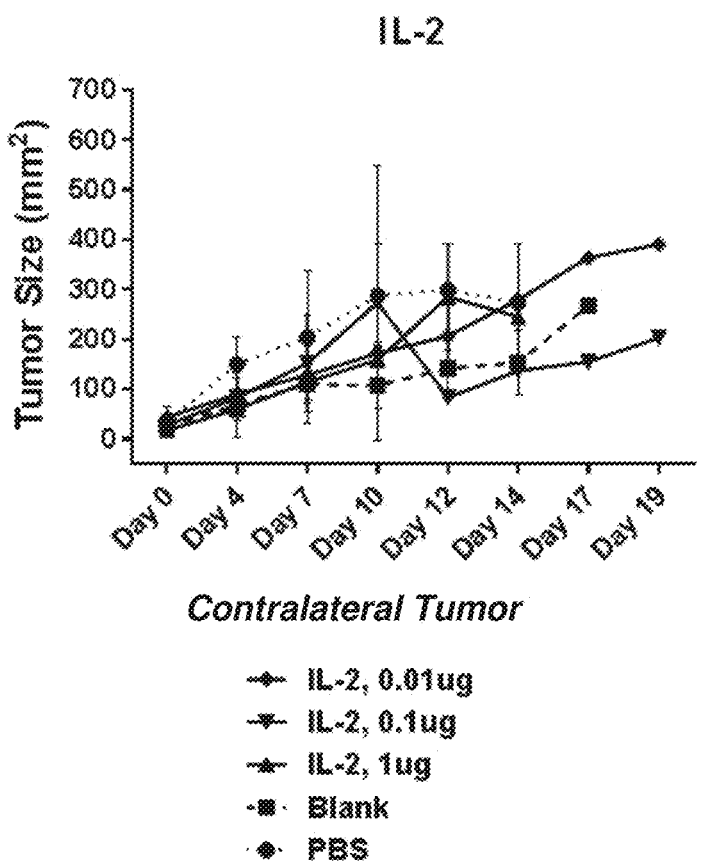
Figure 15A:
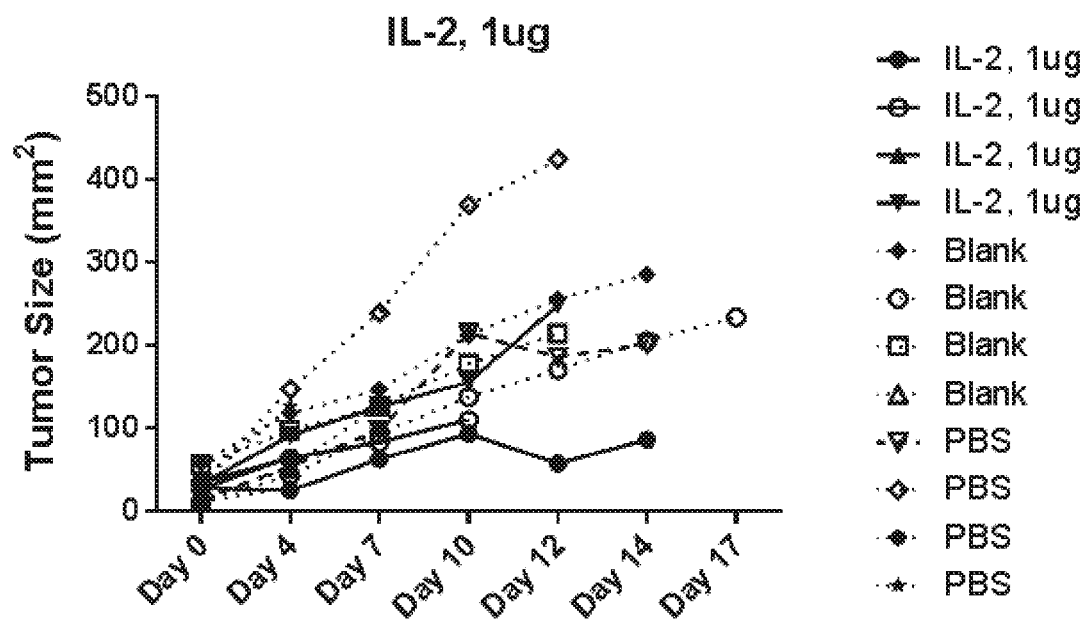
FIGS. 15A-15C are graphs showing the results for individual mice for Example 5 (IL-2).
Figure 15B:
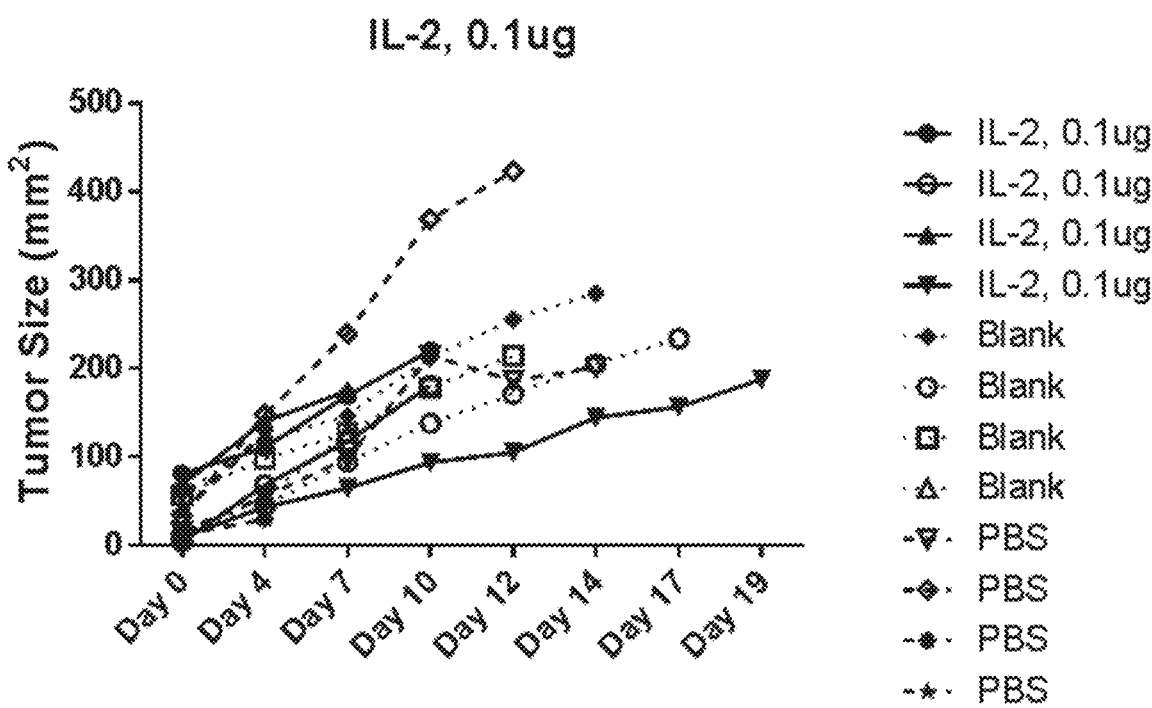
Figure 15C:
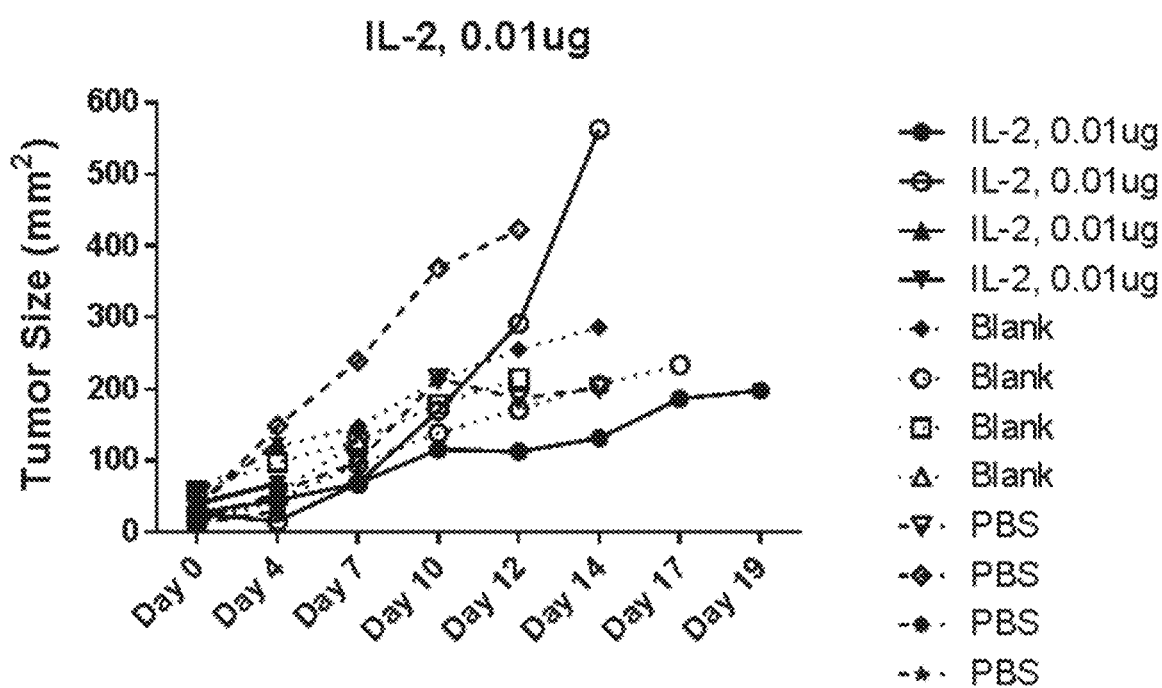
Figure 16:
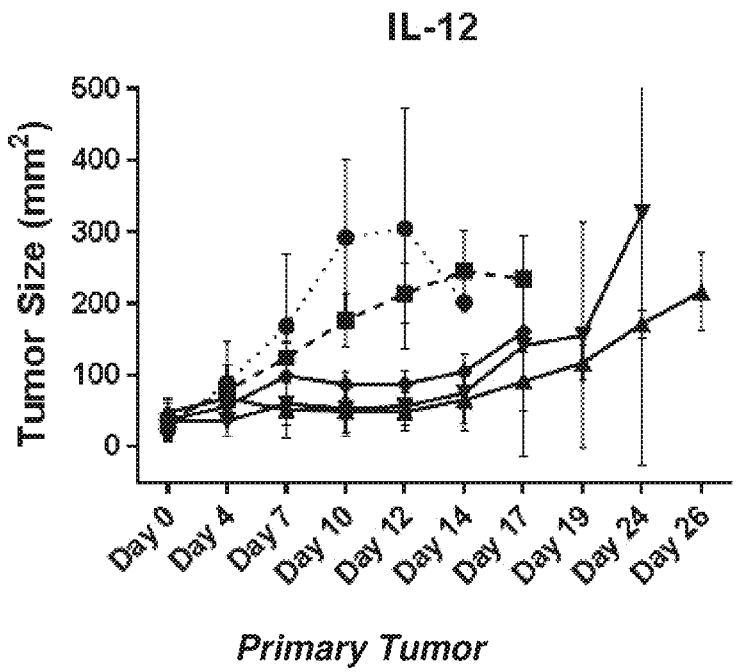
FIG. 16 provides graphs showing a summary of results for Example 5 (IL-12).
Figure 16:
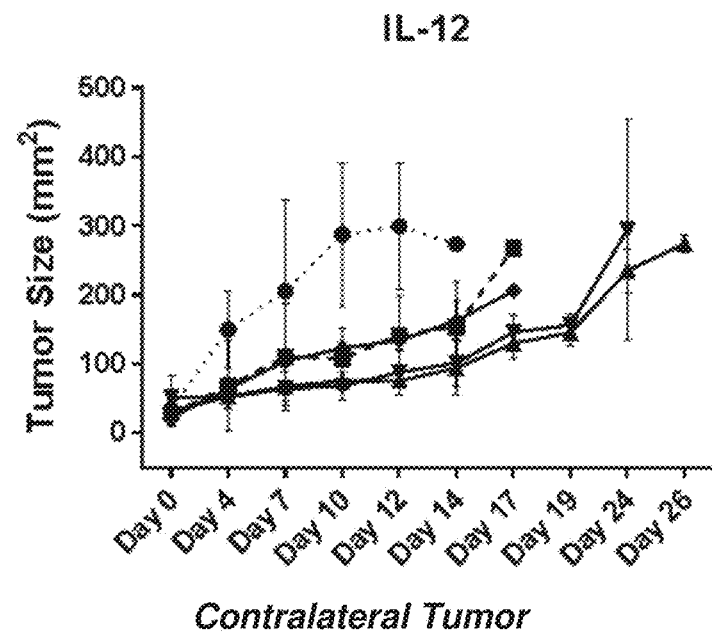
Figure 17A:
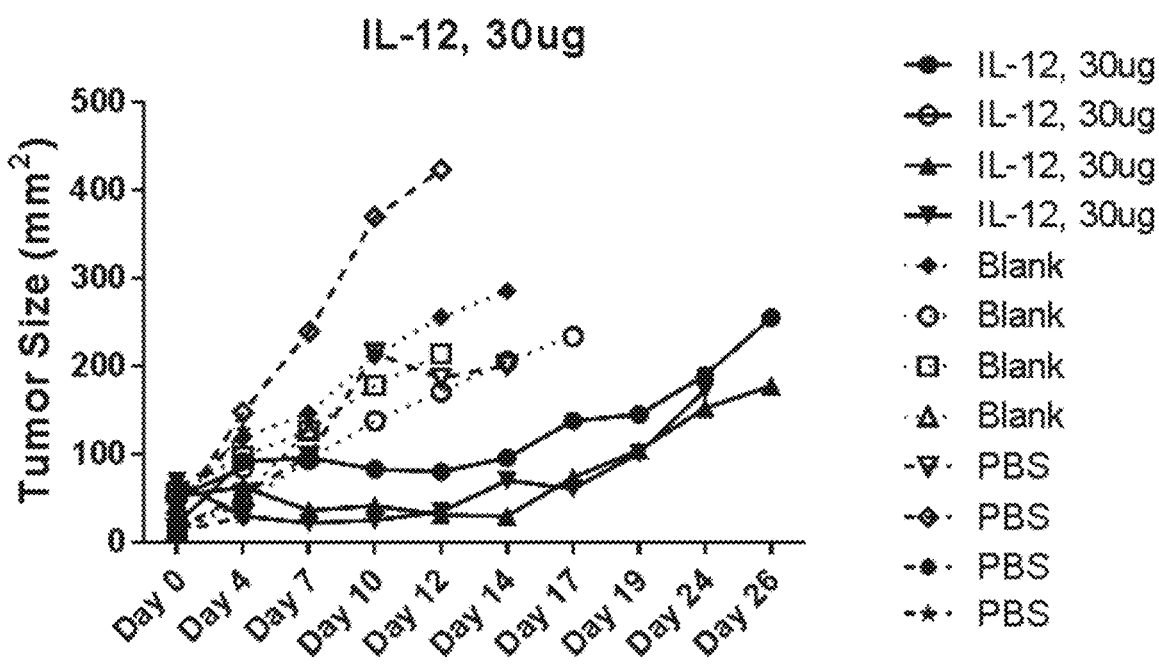
FIGS. 17A-17C are graphs showing the results for individual mice for Example 5 (IL-12).
Figure 17B:
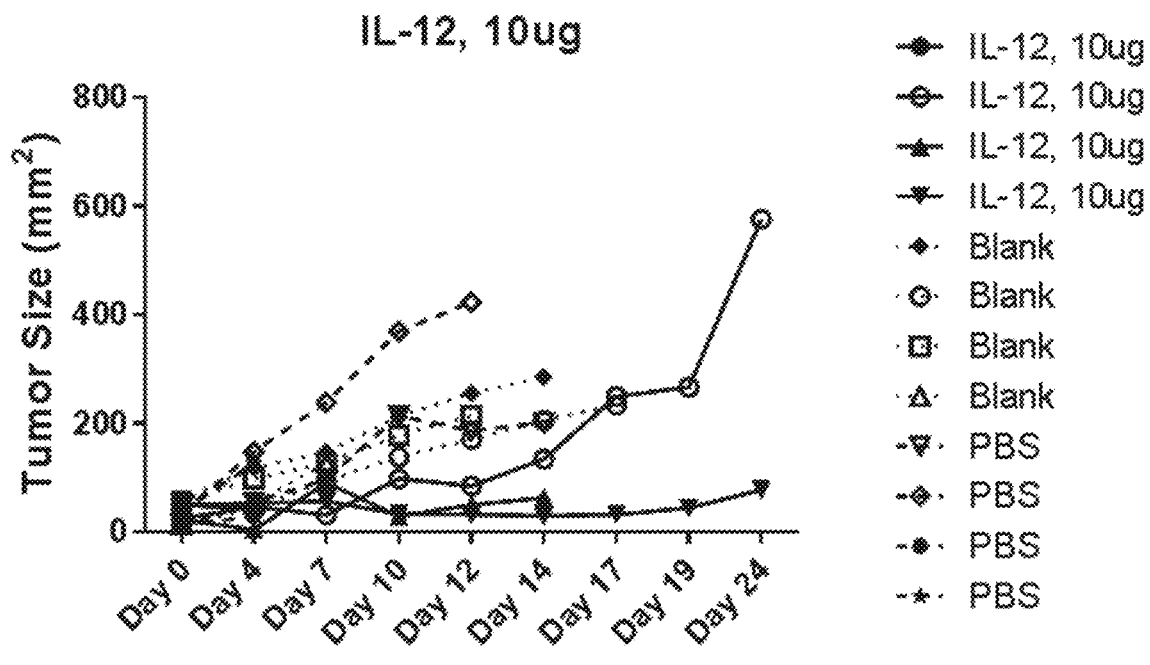
Figure 17C:
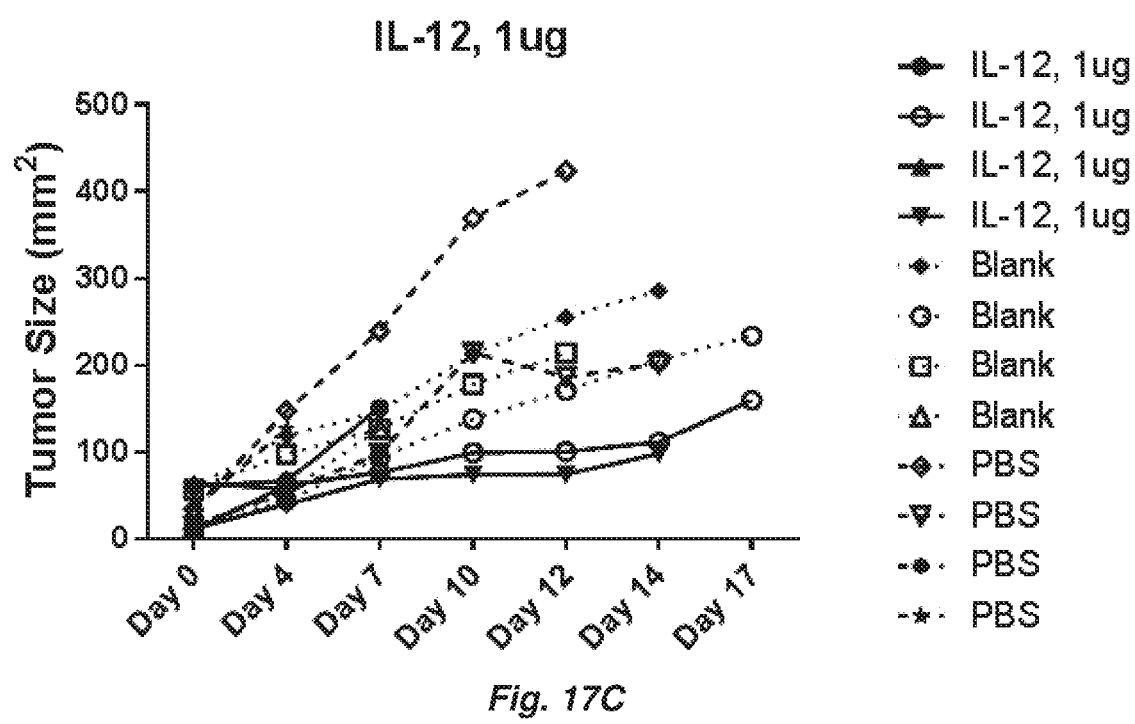

As depicted in FIG. 13, IL-12 in mid- to high-doses prolong survival in mice. One mouse from the IL-12, 30 µg group died early (D4), which is believed to be due to the cancer overpowering the mouse before treatment had a chance to work. There is minimal difference across the IL-2 groups and controls.

As shown in FIGS. 14 and 15A-15C, no significant difference was observed in tumor size across all groups, for both the primary and contralateral sites. It is noted that the drops in average tumor size were due to mice dying, and therefore an artifact.

As shown in FIGS. 16 and 17A-17C, the highest dose (30 ug) yields minimal tumor growth for 3 out of 4 mice. As indicated above, one mouse died early on D4. The mid dose (10 ug) yields some effect but not as pronounced as the high dose; one mouse survived until D24 even though the size of the tumor grew up to 576 mm². The low dose shows the least difference between the experimental and control groups.

While several examples and embodiments of the methods are described hereinabove in detail, other examples and embodiments will be apparent to, and readily made by, those skilled in the art without departing from the scope and spirit of the invention. For example, it is to be understood that this disclosure contemplates that, to the extent possible, one or more features of any embodiment can be combined with one or more features of any other embodiment. Accordingly, the foregoing description is intended to be illustrative rather than restrictive.

The following clauses illustrate various aspects of the invention.

Clause 1: A composition comprising a complex or coacervate of a polycationic polymer, a polyanionic polymer, and a cytokine selected from an interferon and/or an interleukin.

Clause 2: The composition of clause 1, wherein the polyanionic is a heparin or heparan sulfate.

Clause 3: The composition of clause 1, wherein the polycationic polymer is a polymer composition comprising at least one moiety selected from the following:
(a) [—OC(O)—CH(NHY)—CH$_2$—C(O)O—CH$_2$—CH(O—R1)-CH$_2$—O—CH$_2$—CH$_2$—O—CH$_2$—CH(O—R2)-CH$_2$-]$_n$,
(b) [—OC(O)—CH$_2$—CH(NHY)—C(O)O—CH$_2$—CH(O—R1)-CH$_2$—O—CH$_2$—CH$_2$—O—CH$_2$—CH(O—R2)-CH$_2$-]$_n$,
(c) [—OC(O)—CH(NHY)—CH$_2$—CH$_2$—C(O)O—CH2-CH(O—R1)-CH$_2$—O—CH$_2$—CH$_2$—O—CH$_2$—CH(O—R2)-CH$_2$-]$_n$, and/or
(d) [—OC(O)—CH$_2$—CH$_2$—CH(NHY)—C(O)O—CH2-CH(O—R1)-CH$_2$—O—CH$_2$—CH$_2$—O—CH$_2$—CH(O—R2)-CH$_2$-]$_n$,
wherein Y is —C(O)—CH(NH$_3^+$)—(CH$_2$)$_3$—NH—C(NH$_2$)$_2^+$ or —C(O)—CH(NH$_3^+$)—(CH$_2$)$_4$—(NH$_3$)+, and R1 and R2 are the same or different and are independently selected from the group consisting of hydrogen, a carboxy-containing group, a C$_{1-6}$ alkyl group, an amine-containing group, a quaternary ammonium containing group, and a peptide.

Clause 4: The composition of clause 3, in which the polycationic polymer is a polymer composition comprising at least one moiety selected from formulae (a) or (b).

Clause 5: The composition of clause 3, in which the polycationic polymer is a polymer composition comprising at least one moiety selected from formulae (c) or (d).

Clause 6: The composition of any one of clauses 3-5, wherein the polycationic polymer has a polydispersity index of less than 3.0.

Clause 7: The composition of any one of clauses 3-5, wherein the polycationic polymer has a polydispersity index of less than 2.0.

Clause 8: The composition of any one of clauses 3-5, in which R1 and R2 are selected from the group consisting of Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12).

Clause 9: The composition of any one of clauses 3-5, in which the polycationic polymer is complexed with heparin or heparan sulfate.

Clause 10: The composition of any one of clauses 3-5, in which one or both of R1 and R2 are maleate or phosphate.

Clause 11: The composition of any one of clauses 3-5, wherein Y is —C(O)—CH(NH$_3^+$)—(CH$_2$)$_4$—(NH$_3$)$^+$.

Clause 12: The composition of any one of clauses 3-5, wherein Y is —C(O)—CH(NH$_3^+$)—(CH$_2$)$_3$—NH—C(NH$_2$)$_2^+$.

Clause 13: The composition of any one of clauses 3-5, in which R1 is hydrogen.

Clause 14: The composition of any one of clauses 3-5, in which one or both of R1 and R2 are charged.

Clause 15: The composition of any one of clauses 1-14, in which the ratio of the polycationic polymer to the polyanionic polymer in the composition results in a neutral charge.

Clause 16: The composition of any one of clauses 1-14, in which the ratio of the polycationic polymer to the polyanionic polymer in the composition results in a negative charge.

Clause 17: The composition of any one of clauses 1-14, in which the ratio of the polycationic polymer to the polyanionic polymer in the composition results in a positive charge.

Clause 18: The composition of any one of clauses 1-17, wherein the cytokine is one or more cytokines selected from the group consisting of an IL-2 (interleukin-2), an IL-12 (interleukin-12, e.g., IL-12 p70), and/or an IFN-γ (interferon gamma), in any combination.

Clause 19: The composition of any one of clauses 1-17, wherein the cytokine is an IL-12.

Clause 20: The composition of any one of clauses 1-17, wherein the cytokine is an immunomodulatory cytokine.

Clause 21: The composition of clause 20, wherein the cytokine is IL-10, and the composition further comprises an angiogenic growth factor.

Clause 22: The composition of clause 21, wherein the angiogenic growth factor is FGF2.

Clause 23: The composition of any one of clauses 1-22, embedded in a hydrogel.

Clause 24: A method of delivering an interferon and/or an interleukin to a patient in need thereof, comprising administering the composition of any of clauses 1-23 to the patient.

Clause 25: The method of clause 18, wherein the composition is delivered by enteral, parenteral, or topical routes, for example and without limitation by: intravenous (IV), local injection, intramuscular, intracerebral, subcutaneous, orally, inhalation, topically, enema, intravaginal, intrauterine, ocular, or otic routes.

Clause 26: A method of treating a cancer in a patient, comprising, delivering to the patient, e.g. by enteral, parenteral, or topical routes, for example and without limitation by: intravenous (IV), local injection, intramuscular, intracerebral, subcutaneous, orally, inhalation, topically, enema, intravaginal, intrauterine, ocular, or otic routes, the composition of any of clauses 1-20.

Clause 27: The method of clause 26, wherein the cytokine is IL-12.

Clause 28: The method of clause 27 or 28, wherein the cancer is melanoma.

Clause 29: A method of treating a myocardial infarct in a patient, comprising, delivering to the myocardium at or adjacent to the infarct a composition of any one of clauses 20-23.

Clause 30: The method of clause 29, wherein the composition comprises FGF2 and IL-10.

We claim:

1. A composition comprising a complex or coacervate of a polycationic polymer, a polyanionic polymer, and one or more cytokines selected from an IL-2 and an IL-12 in an amount effective to treat melanoma, wherein the coacervate releases the one or more cytokines in a controlled manner over a period of at least two weeks.

2. The composition of claim 1, wherein the polyanionic polymer is a heparin or heparan sulfate.

3. The composition of claim 1, wherein the polycationic polymer is a copolymer comprising a polyester backbone comprising a copolymer of ethylene glycol diglyceride and either aspartic acid or glutamic acid, and pendant arginine groups.

4. The composition of claim 3, wherein the polycationic polymer has a polydispersity index of less than 3.0.

5. The composition of claim 1, in which the ratio of the polycationic polymer to the polyanionic polymer in the composition results in a neutral charge.

6. The composition of claim 1, in which the ratio of the polycationic polymer to the polyanionic polymer in the composition results in a negative charge.

7. The composition of claim 1, in which the ratio of the polycationic polymer to the polyanionic polymer in the composition results in a positive charge.

8. The composition of claim 1, wherein the polycationic polymer is a copolymer comprising a polyester backbone comprising a copolymer of ethylene glycol diglyceride and either aspartic acid or glutamic acid, and pendant lysine groups.

9. The composition of claim 1, wherein the polycationic polymer is poly(ethylene arginylaspartate diglyceride).

10. The composition of claim 1, wherein the polycationic polymer is poly(ethylene lysinylaspartate diglyceride).

11. The composition of claim 1, wherein the cytokine is IL-2.

12. The composition of claim 1, wherein the cytokine is IL-12.

13. The composition of claim 1, embedded in a hydrogel.

14. A method of treating melanoma in a patient, comprising, delivering to the patient the composition of claim 1.

* * * * *

```
SEQUENCE LISTING

<160> NUMBER OF SEQ ID NOS: 12

<210> SEQ ID NO 1
<211> LENGTH: 5
<212> TYPE: PRT
<213> ORGANISM: Homo sapiens

<400> SEQUENCE: 1

Ile Lys Val Ala Val
1               5

<210> SEQ ID NO 2
<211> LENGTH: 4
<212> TYPE: PRT
<213> ORGANISM: Homo sapiens

<400> SEQUENCE: 2

Arg Gly Asp Ser
1

<210> SEQ ID NO 3
<211> LENGTH: 6
<212> TYPE: PRT
<213> ORGANISM: Homo sapiens

<400> SEQUENCE: 3

Lys Gln Ala Gly Asp Val
1               5

<210> SEQ ID NO 4
<211> LENGTH: 6
<212> TYPE: PRT
<213> ORGANISM: Homo sapiens

<400> SEQUENCE: 4

Val Ala Pro Gly Val Gly
1               5

<210> SEQ ID NO 5
<211> LENGTH: 6
<212> TYPE: PRT
<213> ORGANISM: Homo sapiens

<400> SEQUENCE: 5

Ala Pro Gly Val Gly Val
1               5
```

```
<210> SEQ ID NO 6
<211> LENGTH: 6
<212> TYPE: PRT
<213> ORGANISM: Homo sapiens

<400> SEQUENCE: 6

Pro Gly Val Gly Val Ala
1               5

<210> SEQ ID NO 7
<211> LENGTH: 5
<212> TYPE: PRT
<213> ORGANISM: Homo sapiens

<400> SEQUENCE: 7

Gly Val Gly Val Ala
1               5

<210> SEQ ID NO 8
<211> LENGTH: 4
<212> TYPE: PRT
<213> ORGANISM: Homo sapiens

<400> SEQUENCE: 8

Val Ala Pro Gly
1

<210> SEQ ID NO 9
<211> LENGTH: 6
<212> TYPE: PRT
<213> ORGANISM: Homo sapiens

<400> SEQUENCE: 9

Val Gly Val Ala Pro Gly
1               5

<210> SEQ ID NO 10
<211> LENGTH: 4
<212> TYPE: PRT
<213> ORGANISM: Homo sapiens

<400> SEQUENCE: 10

Val Gly Val Ala
1

<210> SEQ ID NO 11
<211> LENGTH: 5
<212> TYPE: PRT
<213> ORGANISM: Homo sapiens

<400> SEQUENCE: 11

Val Ala Pro Gly Val
1               5

<210> SEQ ID NO 12
<211> LENGTH: 6
<212> TYPE: PRT
<213> ORGANISM: Homo sapiens

<400> SEQUENCE: 12

Gly Val Ala Pro Gly Val
1               5
```